US007052889B2

(12) United States Patent
Jenuwein et al.

(10) Patent No.: US 7,052,889 B2
(45) Date of Patent: May 30, 2006

(54) MAMMALIAN SUV39H2 PROTEINS AND ISOLATED DNA MOLECULES ENCODING THEM

(75) Inventors: Thomas Jenuwein, Vienna (AT); Donal O'Carroll, Greystones (IR); Stephen Rea, Headford (IR)

(73) Assignee: Boehringer Ingelheim International GmbH (DE)

( * ) Notice: Subject to any disclaimer, the term of this patent is extended or adjusted under 35 U.S.C. 154(b) by 372 days.

(21) Appl. No.: 10/302,904

(22) Filed: Nov. 25, 2002

(65) Prior Publication Data

US 2003/0104599 A1    Jun. 5, 2003

Related U.S. Application Data

(62) Division of application No. 09/876,224, filed on Jun. 8, 2001, now abandoned.

(60) Provisional application No. 60/224,173, filed on Aug. 9, 2000.

(30) Foreign Application Priority Data

Jun. 9, 2000   (EP) .................................. 00112345
Jun. 9, 2000   (EP) .................................. 00112479

(51) Int. Cl.
  *C12N 9/10*   (2006.01)
  *C07H 21/04*  (2006.01)

(52) U.S. Cl. .............. 435/193; 435/252.33; 435/320.1; 435/471; 536/23.2; 536/23.1; 536/23.5

(58) Field of Classification Search ................ 435/193, 435/252.3, 252.33, 325, 320.1; 536/23.2, 536/23.5; 436/23.1
See application file for complete search history.

(56) References Cited

U.S. PATENT DOCUMENTS

| 5,972,608 | A  | 10/1999 | Peterson et al. ............... 435/6 |
| 6,555,329 | B1 | 4/2003  | Jenuwein et al. .............. 435/15 |
| 6,689,583 | B1 | 2/2004  | Jenuwein et al. ........... 435/69.1 |
| 2002/0039776 | A1 | 4/2002 | Jenuwein et al. ........... 435/193 |
| 2002/0164620 | A1 | 11/2002 | Peters et al. .................... 435/6 |
| 2003/0087368 | A1 | 5/2003  | Maupin-Furlow et al. . 435/69.1 |
| 2003/0157532 | A1 | 8/2003  | Jenuwein et al. ............... 435/6 |

FOREIGN PATENT DOCUMENTS

| DE | 195 16 776    | 11/1996 |
| WO | WO 95/15749   | 6/1995  |
| WO | WO 98/27994   | 7/1998  |
| WO | WO 98/49190   | 11/1998 |
| WO | 1 227 160 A1  | 7/2002  |

OTHER PUBLICATIONS

Marra et al. EST database, Accession No. AA066708, Feb. 6, 1997.*

(Continued)

*Primary Examiner*—Nashaat T. Nashed
(74) *Attorney, Agent, or Firm*—Sterne, Kessler, Goldstein & Fox P.L.L.C.

(57) ABSTRACT

Murine and human Suv39h2 polypeptide and DNA molecules encoding them. Suv39h2 is a novel member of the Suv3-9 gene family. Suv39h2 is a novel component of meiotic higher order chromatin. It has histone methyltransferase activity and is required, in combination with Suv39h1, for male gametogenesis. Suv39h2 can be used in screening methods to identify modulators of its methyltransferase activity, which are useful in cancer therapy and for male contraception.

20 Claims, 34 Drawing Sheets

OTHER PUBLICATIONS

Aagaard, L., et al., "Functional mammalian homologues of the *Drosophila* PEV-modifier Su(var)3- 9 encode centromere-associated proteins which complex with the heterochromatin component M31," *EMBO J.* 18:1923-1938, Oxford University Press (Apr., 1999).

Aagaard, L., et al., "Mitotic phosphorylation of SUV39H1, a novel component of active centromeres, coincides with transient accumulation at mammalian centromeres," *J. Cell Sci.* 113:817-829, Company of Biologists Ltd. (Mar. 2000).

Aasland, R. and Stewart, A.F., "The chromo shadow domain, a second chromo domain in heterochromatin- binding protein 1, HP1," *Nucl. Acids Res.* 23:3168-3174, Oxford University Press (1995).

Adams, R.R., et al., "INCENP binds the Aurora-related kinase AIRK2 and is required to target it to chromosomes, the central spindle and cleavage furrow," *Curr. Biol.* 10:1075-1078, Cell Press (Sep. 2000).

Ainsztein, A.M., et al., "INCENP centromere and spindle targeting: identification of essential conserved motifs and involvement of heterochromatin protein HP1," *J. Cell Biol.* 143:1763-1774, Rockefeller University Press (1998).

Allshire, R.C., et al., "Mutations derepressing silent centromeric domains in fission yeast disrupt chromosome segregation," *Genes Dev.* 9:218-33, Cold Spring Harbor Laboratory Press (1995).

Altschul, S.F., et al., "Gapped BLAST and PSI-BLAST: a new generation of protein database search programs," *Nucl. Acids Res.* 25:3389-3402, Oxford University Press (1997).

Ball, L.J., et al., "Structure of the chromatin binding (chromo) domain from mouse modifier protein 1," *EMBO J.* 16:2473-2481, Oxford University Press (1997).

Bannister, A.J., et al., "Selective recognition of methylated lysine 9 on histone H3 by the HP1 chromo domain," *Nature* 410:120-124, Macmillan Magazines Ltd. (Mar. 2001).

Bassett, D.E., Jr., et al., "Comparative genomics, genome cross-referencing and XREFdb," *Trends Genet.* 11:372-373, Elsevier Science Ltd. (1995).

Baudat, F., et al, "Chromosome synapsis defects and sexually dimorphic meiotic progression in mice lacking Spo11" *Mol. Cell.* 6:989-998, Cell Press (Nov. 2000).

Bernard, P., et al., "Fission yeast Bub1 is a mitotic centromere protein essential for the spindle checkpoint and the preservation of correct ploidy through mitosis," *J. Cell Biol.* 143:1775-1787, Rockefeller University Press (1998).

Boulianne, G.L., et al., "Production of functional chimaeric mouse/human antibody," *Nature* 312:643-646, Macmillan Magazines Ltd. (1984).

Bunick, D., et al., "Transcription of the testis-specific mouse protamine 2 gene in a homologous *in vitro* transcription system," *Proc. Natl. Acad. Sci.* USA, 87:891-895, National Academy of Sciences (1990).

Burgoyne, P.S., "Genetic homology and crossing over in the X and Y chromosomes of mammals," *Hum. Genet.* 61:85-90, Springer-Verlag (1982).

Calenda, A., et al., "The meiosis-specific *Xmr* gene product is homologous to the lymphocyte Xlr protein and is a component of the XY body," *Embo J.* 13:100-109, Oxford University Press (1994).

Cobb, J., et al., "Meiotic events at the centromeric heterochromatin: histone H3 phosphorylation, topoisomerase IIα localization and chromosome condensation," *Chromosoma* 108:412-425, Springer-Verlag (Dec. 1999).

Cortez, D. and Elledge, S.J., "Conducting the mitotic symphony," *Nature* 406:354-356, Macmillian Magazines Ltd. (Jul. 2000).

Csink, A. and Henikoff, S., "Genetic modification of heterochromatic association and nuclear organization in *Drosophila*," *Nature* 381:529-531, Macmillan Magazines Ltd. (1996).

Cutts, S.M., et al., "Defective chromosome segregation, microtubule bundling and nuclear bridging in inner centromere protein gene (*Incenp*)-disrupted mice, " *Hum. Mol. Genet.* 8:1145-1155, Oxford University Press (Jul. 1999).

Czvitkovich, S., et al., "Over-expression of the SUV39H1 histone methyltransferase induces altered proliferation and differentiation in transgenic mice," *Mech. Dev.* 107:141-153, Elsevier Science Ireland Ltd. (Sep. 2001).

Dernburg, A.F., et al., "Perturbation of nuclear architecture by long-distance chromosome interactions," *Cell* 85:745-759, Cell Press (1996).

Dernburg, A.F., et al., "Direct evidence of a role for heterochromatin in meiotic chromosome segregation," *Cell* 86:135-146, Cell Press (1996).

de Vries, S.S., et al., "Mouse MutS-like protein Msh5 is required for proper chromosome synapsis in male and female meiosis," *Genes Dev.* 13:523-531, Cold Spring Harbor Laboratory Press (Mar. 1999).

Dugaiczyk, A., et al., "Cloning and sequencing of a deoxyribonucleic acid copy of glyceraldehyde-3-phosphate dehydrogenase messenger ribonucleic acid isolated from chicken muscle," *Biochemistry* 22:1605-13, American Chemical Society (1983).

Ekwall, K., et al., "Transient inhibition of histone deacetylation alters the structural and functional imprint at fission yeast centromeres," *Cell* 91:1021-1032, Cell Press (1997).

Foon, K.A., and Gale, R.P. "Chronic Lymphoid Leukemias," in: *Blood: Principles and Practice of Hematology*, R.I. Handin, et al., eds., J.B. Lippincott Company, Philadelphia, PA, pp. 783-811 (1995).

Gentz, R., et al., "Bioassay for trans-activation using purified human immunodeficiency virus *tat*-encoded protein: trans-activation requires mRNA synthesis," *Proc. Natl. Acad. Sci. USA* 86:821-824, National Academy of Sciences (1989).

Graziano, R.F., et al., "Construction and characterization of a humanized anti-γ -Ig receptor type I (FcγRI) monoclonal antibody," *J. Immunol.* 155:4996-5002, American Association of Immunologists (1995).

Handel, M.A. and Hunt, P.A., "Sex-chromosome pairing and activity during mammalian meiosis," *Bioessays* 14:817-22, John Wiley and Sons, Inc. (1992).

Hawley, R.S., et al., "There are two mechanisms of achiasmate segregation in *Drosophila* females, one of which requires heterochromatic homology," *Dev. Genet.* 13:440-467, Wiley-Liss, Inc. (1992).

Henikoff, S., "Position-effect Variegation in *Drosophila*: Recent Progress," in *Epigenetic Mechanisms of Gene Regulation*, Russo, V.E.A., et al., eds., Cold Spring Harbor Laboratory Press, Plainview, New York (1997).

Hsu, J.Y., et al., "Mitotic phosphorylation of histone H3 is governed by Ipl1/aurora kinase and Glc7/PP1 phosphatase in budding yeast and nematodes," *Cell* 102:279-291, Cell Press (Aug. 2000).

Ivanova, A.V., et al., "The chromo and SET domains of the Clr4 protein are essential for silencing in fission yeast," *Nat. Genet.* 19:192-195, Macmillan Magazines Ltd. (1998).

Jenuwein, T., et al., SET domain proteins modulate chromatin domains in eu- and heterochromatin. *Cell. Mol. Life Sci.* 54:80-93, Birkhauser Verlag AG (1998).

Jenuwein, T., "Re-SET-ting heterochromatin by histone methyltransferases," *Trends Cell Biol.* 11:266-273, Elsevier Science Ltd. (Jun. 2001).

Jones, D.O., et al., "Mammalian chromodomain proteins: their role in genome organisation and expression," *Bioessays* 22:124-237, John Wiley and Sons, Inc. (Feb. 2000).

Kaitna, S., et al., "Incenp and an Aurora-like kinase form a complex essential for chromosome segregation and efficient completion of cytokinesis," *Curr. Biol.* 10:1172-1181, Cell Press (Oct. 2000).

Karpen, G. H., et al., "Centric heterochromatin and the efficiency of achiasmate disjunction in *Drosophila* female meiosis," *Science* 273:118-122, American Association for the Advancement of Science (1996).

Karpen, G.H. and Allshire, R.C., "The case for epigenetic effects on centromere identity and function," *Trends Genet.* 13:489-496, Elsevier Science Ltd. (1997).

Köhler, G. and Milstein, C., "Continuous cultures of fused cells secreting antibody of predefined specificity," *Nature* 256:495-497, Macmillan Magazines Ltd. (1975).

Koonin, E.V., et al., "The chromo superfamily: new members, duplication of the chromo domain and possible role in delivering transcription regulators to chromatin," *Nucl. Acids Res.* 23:4229-33, Oxford University Press (1995).

Kot, M.C. and Handel, M.A. "Spermatogenesis in XO, *Sxr* mice: Role of the Y Chromosome," *J. Exp. Zool.* 256:92-105, Wiley-Liss, Inc. (1990).

Lachner, M., et al., "Methylation of histone H3 lysine 9 creates a binding site for HP1 proteins," *Nature* 410:116-120, Macmillan Magazines Ltd. (Mar. 2001).

Laible, G., et al., "Mammalian homologues of the *Polycomb*-group gene *Enhancer of zeste* mediate gene silencing in *Drosophila* heterochromatin and at *S. cerevisiae* telomeres," *EMBO J.* 16:3219-32, Oxford University Press (1997).

Lamb, D.J. and Niederberger, C.S. "Animal Models that Mimic Human Male Reproductive Defects," *Urol. Clin. North Am.* 21:377-87, W.B. Saunders Co. (1994).

Lammers, J.H.M., et al., "The Gene Encoding a Major Component of the Lateral Elements of Synaptonemal Complexes of the Rat Is Related to X-Linked Lymphocyte-Regulated Genes," *Mol. Cell. Biol.* 14:1137-46, American Society for Microbiology (1994).

Lammers, J.H.M., et al., "A change in the phosphorylation pattern of the 30,000-33,000 $M_r$ synaptonemal complex proteins of the rat between early and mid-pachytene," *Chromosoma* 104:154-163, Springer-Verlag (1995).

Matsuda, Y., et al., "Genetic basis of X-Y chromosome dissociation and male sterility in interspecific hybrids," *Proc. Natl. Acad. Sci. USA* 88:4850-4854, National Academy of Sciences (1991).

Meistrich, M.L. and Brock, W.A., "Proteins of the meiotic cell nucleus," In *Meiosis*, Moens, P.B., ed., Academic Press, New York, N.Y., pp. 333-353 (1987).

Melcher, M., et al., "Structure-Function Analysis of SUV39H1 Reveals a Dominant Role in Heterochromatin Organization, Chromosome Segregation, and Mitotic Progression," *Mol. Cell. Biol.* 20:3728-3741, American Society for Microbiology (May 2000).

Messmer, S., et al., Analysis of the functional role of the *Polycomb* chromo domain in *Drosophila melanogaster*, *Genes Dev.* 6:1241-1254, Cold Spring Harbor Laboratory Press (1992).

Moens, P.B., "Histones H1 and H4 of surface-spread meiotic chromosomes," *Chromosoma* 104:169-174, Springer-Verlag (1995).

Motzkus, D., et al., "M31, a murine homolog of Drosophila HP1, is concentrated in the XY body during spermatogenesis," *Cytogenet. Cell Genet.* 86:83-88, S. Karger AG (Oct. 1999).

Nakayama, J., et al., "Role of Histone H3 Lysine 9 Methylation in Epigenetic Control of Heterochromatin Assembly," *Science* 292:110-113, American Association for the Advancement of Science (Apr. 2001).

Neuberger, M.S., et al., "Recombinant antibodies possessing novel effector functions," *Nature* 312:604-608, Macmillan Magazines Ltd. (1984).

O'Carroll, D., et al., "Isolation and Characterization of Suv39h2, a Second Histone H3 Methyltransferase Gene That Displays Testis-Specific Expression," *Mol. Cell. Biol.* 20:9423-9433, American Society for Microbiology (Dec. 2000).

Offenberg, H.H., et al., "Tissue distribution of two major components of synaptonemal complexes of the rat," *Chromosoma* 101:83-91, Springer-Verlag (1991).

Pandita, T.K., et al., "*Atm* Inactivation Results in Aberrant Telomere Clustering during Meiotic Prophase," *Mol. Cell. Biol.* 19:5096-5105, American Society for Microbiology (Jul. 1999).

Pardue, M.L. and Gall, J.G., "Chromosomal Localization of Mouse Satellite DNA," *Science* 168:1356-1358, American Association for the Advancement of Science (1970).

Paro, R. and Harte, P.J., "The Role of Polycomb Group and Thrithorax Group Chromatin Complexes in the Maintenance of Determined Cell States," in *Epigenetic Mechanisms of Gene Regulation*, Russo, V.E.A., et al., eds., Coldspring Harbor Laboratory Press, Plainview, N.Y., pp. 507-528 (1996).

Paro, R. and Hogness, D.S. "The Polycomb protein shares a homologous domain with a heterochromatin- associated protein of *Drosophila*," *Proc. Natl. Acad. Sci. USA* 88:263-267, National Academy of Sciences (1991).

Peters, A.H.F.M., et al., "A drying-down technique for the spreading of mammalian meiocytes from the male and female germline," *Chromosome Res.* 5:66-68, Rapid Science Publishers (1997).

Peters, A.H.F.M., et al., Meiosis in carriers of heteromorphic bivalents: sex differences and implications for male fertility. *Chromosome Res.* 5:313-324, Rapid Science Publishers (1997).

Platero, J.S., et al., "Functional analysis of the chromo domain of HP1," *EMBO J.* 14:3977-3986, Oxford University Press (1995).

Rea, S., et al., "Regulation of chromatin structure by site-specific histone H3 methyltransferases," *Nature* 406:593-599, Macmillan Magazines Ltd. (Aug. 2000).

Reuter, G. and Spierer, P., "Position Effect Variegation and Chromatin Proteins," *BioEssays* 14:605-612, Company of Biologists Ltd. (1992).

Rice, J.C. and Allis, C.D., "Histone methylation versus acetylation: new insights into epigenetic regulation," *Curr. Opin. Cell. Biol.* 13:263-273, Elsevier Science Ltd. (Jun. 2001).

Riechmann, L., et al., "Reshaping human antibodies for therapy," *Nature* 332:323-327, Macmillan Magazines Ltd. (1988).

Scherthan, H., et al., "Centromere and Telomere Movements during Early Meiotic Prophase of Mouse and Man are Associated with the Onset of Chromosome Pairing," *J. Cell Biol.* 134:1109-25, Rockefeller University Press (1996).

Solari, A.J. "The behavior of the XY pair in mammals," *Int. Rev. Cytol.* 38:273-317, Academic Press, Inc. (1974).

Stassen, M.J., et al., "The *Drosophila trithorax* proteins contain a novel variant of the nuclear receptor type DNA binding domain and an ancient conserved motif found in other chromosomal proteins," *Mech. Dev.* 52:209-223, Elsevier Science Ltd. Ireland (1995).

Strahl, B.D., et al., Methylation of histone H3 at lysine 4 is highly conserved and correlates with transcriptionally active nuclei in Tetrahymena, *Proc. Natl. Acad. Sci. USA* 96:14967-72, Nationally Academy of Sciences (Dec. 1999).

Tkachuk, D.C., et al., "Involvement of a Homolog of *Drosophila trithorax* by 11q23 Chromosomal Translocations in Acute Leukemias," *Cell* 71:691-700, Cell Press (1992).

Tschiersch, B., et al., "The protein encoded by the *Drosophila* position-effect variegation suppressor gene Su(var)3-9 combines domains of antagonistic regulators of homeotic gene complexes," *EMBO J.* 13:3822-3831, Oxford University Press (1994).

Turner, J.M.A., et al., "Analysis of male meiotic 'sex body' proteins during XY female meiosis provides new insights into their functions," *Chromosoma* 109:426-432, Springer-Verlag (Aug. 2000).

Wallrath, L.L., "Unfolding the mysteries of heterochromatin," *Curr. Opin. Genet. Dev.* 8:147-153, Elsevier Science Ltd. (1998).

Weinbauer, G.F., et al., "Quantitative Analysis of Spermatogenesis and Apoptosis in the Common Marmoset (*Callithrix jacchus*) Reveals High Rates of Spermatogonial Turnover and High Spermatogenic Efficiency," *Biol. Reprod.* 64:120-126, Society for the Study of Reproduction (Jan. 2001).

Wilson, I.A., et al., "The Structure of an Antigenic Determinant in a Protein," *Cell* 37: 767-778, Massachusetts Institute of Technology (1984).

Wreggett, K.A., et al., "A mammalian homologue of *Drosophila* heterochromatin protein 1 (HP1) is a component of constitutive heterochromatin," *Cytogenet. Cell Genet.* 66:99-103, S. Karger AG (1994).

Xu, Y., et al., "Targeted disruption of *ATM* leads to growth retardation, chromosomal fragmentation during meiosis, immune defects, and thymic lymphoma," *Genes Dev.* 10:2411-2422, Cold Spring Harbor Laboratory Press (1996).

Yoshida, K., et al., "The Mouse RecA-like Gene *Dmc1* is Required for Homologous Chromosome Synapsis during Meiosis," *Mol. Cell* 1:707-718, Cell Press (1998).

Yuan, L., et al., "The Murine *SCP3* Gene is Required for Synaptonemal Complex Assembly, Chromosome Synapsis, and Male Fertility," *Mol. Cell* 5:73-83, Cell Press (Jan. 2000).

Pending U.S. Appl. No. 09/876,221, filed Jun. 8, 2001, Jenuwien et al.

Pending U.S. Appl. No. 09/876,224, filed Jun. 8, 2001, Jenuwien et al.

Adams, et al., "*Pax-5* encodes the transcription factor BSAP and is expressed in B lymphocytes, the developing CNS, and adult testis," *Genes & Dev.* 6:1589-1607, Cold Spring Harbor Laboratory Press (1992).

Alkema, et al., "Transformation of axial skeleton due to overexpression of *bmi*-1 in transgenic mice," *Nature* 374:724-727, Nature Publishing Group (1995).

Ambrose, W.P., et al., "Detection System for Reaction-Rate Analysis in a Low-Volume Proteinase-Inhibition Assay," *Anal. Biochem.* 263:150-157, Academic Press (1998).

Baksa, K., et al., "Mutations in the Protein Phosphate 1 Gene at 87B Can Differentially Affect Suppression of Position-Effect Variegation and Mitosis in *Drosophila melanogaster*," *Genet.* 135:117-125, The Genetics Society of America (1993).

Barrett, A.J. and Kirschke, H., "Cathepsin B, Cathepsin H, and Cathepsin L," *Methods Enzym.* 80:535-561, Academic Press (1981).

Brown, A.M., et al., "Biotinylated and Cysteine-Modified Peptides as Useful Reagents for Studying the Inhibition of Cathespin G," *Anal. Biochem.* 217:139-147, Academic Press (1994).

Brunk, et al., "Drosophila genes *Posterior Sex Combs* and *Suppressor two of zeste* encode proteins with homology to the murine *bmi-1* oncogene," *Nature* 353:351-353, Nature Publishing Group (1991).

Buck, S.W, and Shore, D., "Action of a RAP1 carboxy-terminal silencing domain reveals an underlying competition between *HMR* and telomeres in yeast," *Genes & Dev.* 9:370-384, Cold Spring Harbor Laboratory Press (1995).

Buonomo, S.B.C., et al., "Disjunction of Homologous Chromosomes in Meiosis I Depends on Proteolytic Cleavage of the Meiotic Cohesion Rec8 by Separin," *Cell* 103:387-398, Cell Press (Oct. 2000).

Cai, J. et al., "Reconstitution of human replication factor C from its five subunits in baculovirus-infected insect cells," *Proc. Natl. Acad. Sci. USA* 93:12896-12901, National Academy of Sciences (1996).

Cerretani, M., et al., "A High-Throughput Radiometric Assay for Hepatitis C Virus NS3 Protease," *Anal. Biochem.* 266:192-197, Academic Press (Jan. 1999).

Chen, D., et al., "Regulation of Transcription by a Protein Methyltransferase," *Science* 284:2174-2177, American Association for the Advancement of Science (Jun. 1999).

Ciosk, R., et al., "An ESP1/PDS1 Complex Regulates Loss of Sister Chromatid Cohesion at the Metaphase to Anaphase Transition in Yeast," *Cell* 93:1067-1076, Cell Press (1998).

Clark, D.A., et al., "Protease Inhibitors Suppress In Vitro Growth of Human Small Cell Lung Cancer," *Peptides* 14:1021-1028, Pergamon Press (1993).

Cleard, F. et al., "SU (VAR) 3-7, a *Drosophila* heterochromatin-associated protein and companion of HP1 in the genomic silencing of positon-effect variegation," *The EMBO Journal* 16:5280-5288, Oxford University Press (1997).

Cohen-Fix, O. et al., "Anaphase initiation in *Saccharomyces cerevisiae* is controlled by the APC-dependent degradation of the anaphase inhibitor Pds1p," *Genes & Dev.* 10:3081-3093, Cold Spring Harbor Laboratory Press (1996).

DeCamillis, M., et al., "The *polyhomeotic* gene of *Drosophila* encodes a chromatin protein that shares polytene chromosome-binding sites with *Polycomb*," *Genes & Dev.* 6:223-232, Cold Spring Harbor Laboratory Press (1992).

De Rubertis, F. et al., "The histone deacetylase RPD3 counteracts genomic silencing in *Drosophila* and yeast," *Nature* 384:589-591, Nature Publishing Group (1996).

Dominguez, A. et al., "hpttg, a human homologue of rat *pttg*, is overexpressed in hematopoietic neoplasms. Evidence for a transcriptional activation function of hPTTG," *Oncogene* 17:2187-2193, Nature Publishing Group (1998).

Dougherty, W. et al., "Molecular Genetic Analysis of a Plant Virus Polyprotein Cleavage Site: A Model," *Virology* 171:356-364, Academic Press (1989).

Eissenberg, J.C., et al., "The Heterochromatin-Associated Protein HP-1 is an Essential Protein in Drosophila With Dosage-Dependent Effects on Position-Effect Variegation," *Genetics* 131:345-352, Genetics Society of America (1992).

Ekwall, K., et al., "Mutations in the fission yeast silencing factors *clr4+* and *rik1+* disrupt the localisation of the chromo domain protein Swi6p and impair centromere function," *J. Cell Sci.* 109: 2637-2648, The Company of Biologists Limited (1996).

Elbashir, S.M., et al., "Duplexes of 21-nucleotide RNAs mediate RNA interference in cultured mammalian cells," *Nature* 411:494-498, Nature Publishing Company (May 2001).

Epstein, C.B., and Cross, F.R. "*CLB5*: a novel B cyclin from budding yeast with a role in S phase," *Genes & Dev.* 6:1695-1706, Cold Spring Harbor Laboratory Press (1992).

Faleiro, L., et al., "Multiple species of CPP32 and Mch2 are the major active caspases present in apoptotic cells," *EMBO J.* 16:2271-2281, Oxford University Press (1997).

Friedman, L.S., et al., "The Search for BRCA1," *Cancer Res.* 54:6374-6382, American Association for Cancer Research (1994).

Friedman, L.S., et al., "22 Genes from Chromosome 17q21: Cloning, Sequencing, and Characterization of Mutations in Breast Cancer Families and Tumors," *Genomics* 25:256-263, Academic Press (1995).

Funabiki, H. et al., "Cut2 proteolysis required for sister-chromatid separation in fission yeast," *Nature* 381:438-441, Nature Publishing Group (1996).

Garzino, V., "Cell lineage-specific expression of *modulo*, a dose-dependent modifier of variegation in *Drosophila*," *EMBO J.* 11:4471-4479, Oxford University Press (1992).

Geraghty, M.T., et al., "The Isolation of cDNAs from OATL1 at Xp11.2 Using a 480-kb YAC," *Genomics* 16:440-446, Academic Press (1993).

Gershkovich, A.A. and Kholodovych, V.V., "Fluorogenic substrates for proteases based on intramolecular fluorescence energy transfer (IFETS)," *J. Biochem. Biophys. Methods* 33:135-162, Elsevier Science B.V. (1996).

Gibbons, R.J., et al., "Mutations in a Putative Global Transcriptional Regulator Cause X-Linked mental Retardation with α-Thalassemia (ATR-X Syndrome)," *Cell* 80:837-845, Cell Press (1995).

Gietz, R.D. and Sugino, A., "New yeast—*Escherichia coli* shuttle vectors constructed with in vitro mutagenized yeast genes lacking six-base pair restriction sites," *Gene* 74:527-534, Elsevier/North Holland (1988).

Gmachl, M., et al., "The RING-H2 finger protein APC11 and the E2 enzyme UBC4 are sufficient to ubiquitinate substrates of the anaphase-promoting complex," *Proc. Natl. Acad. Sci. USA* 97:8973-8978, National Academy of Sciences (Aug. 2000).

Gray, N.M., et al., "Discovery and Analysis of a Series of C2-Symmetric HIV-1 Proteinase Inhibitors Derived from Penicillin," *Anal. Biochem.* 216:89-96, Academic Press (1994).

Griffin, D.K., et al., "Sex Ratio in Normal and Disomic Sperm: Evidence That the Extra Chromosome 21 Preferentially Segregates with Y Chromosome," *Am. J. Hum. Genet.* 59:1108-1113, The University of Chicago Press (1996).

Grunstein, M., "Yeast Heterochromatin: Regulation of its Assembly and Inheritance by Histones," *Cell* 93:325-328, Cell Press (1998).

Gu, Y., et al., "The t(4;11) Chromosome Translocation of Human Acute Leukemias Fuses the *ALL-1* Gene, Related to *Drosophila trithorax*, to the *AF-4* Gene," *Cell* 71:701-708, Cell Press (1992).

Hauf, S., et al., "Cohesion Cleavage by Separase Required for Anaphase and Cytokinesis in Human Cells," *Science* 293:1320-1323, The American Association for the Advancement of Science (Aug. 2001).

Haupt, Y., et al., "Novel Zinc Finger Gene Implicated as *myc* Collaborator by Retrovirally Accelerated Lymphomagenesis in Eÿ-*myc* Transgenic Mice," *Cell* 65:753-763, Cell Press (1991).

Hayden, J.H. et al., "Kinetochores Capture Astral Microtubules During Chromosome Attachment to the Mitotic Spindle: Direct Visualization in Live Newt Lung Cells," *J. Cell Biol.* 111:1039-1045, Rockefeller University Press (1990).

Hendzel, M.J., et al., "Mitosis-specific phosphorylation of histone H3 initiates primarily within pericentromeric heterochromatin during G2 and spreads in an ordered fashion coincident with mitotic chromosome condensation," *Chromosoma* 106:348-360, Springer-Verlag (1997).

Hobert, O., et al., "Interaction of Vav with ENX-1, a Putative Transcriptional Regulator of Homeobox Gene Expression," *Mol. Cell. Biol.* 16:3066-3073, American Society for Microbiology (Jun. 1996).

Jacobson, S. and Pillus, L., "Modifying chromatin and concepts of cancer," *Curr. Opin. Genet. Dev.* 9:175-184, Current Biology Publications (Apr. 1999).

Jolley, M.E., "Fluorescence Polarization Assays for the Detection of Proteases and Their Inhibitors," *J. Biomol. Scr.* 1:33-38, Mary Ann Liebert, Inc. (1996).

Jones, R.S., and Gelbart, W.M., "The *Drosophila* Polycomb-Group Gene *Enhancer of zeste* Contains a Region with Sequence Similarity to *trithoras*," *Mol. Cell. Biol.* 13:6357-6366, American Society for Microbiology (1993).

Kerrebrock, A.W. et al., "Mei-s332, a Drosophila Protein Required for Sister-Chromatoid Cohesion, Can Localize to Meitic Centromere Regions," *Cell* 83:247-256, Cell Press (1995).

Klein, F. et al., "A Central Role for Cohesins in Sister Chromatid Cohesion, Formation of Axial Elements, and Recombination during Yeast Meiosis," *Cell* 98:97-103, Cell Press (Jul. 1999).

Klein, R.R. and Houtz, R.L., "Cloning and developmental expression of pea ribulose-1, 5-bisphosphate carbosylase/oxygenase large subunit N-methyltransferase," *Plant Mol. Biol.* 27:249-261, Kluwer Academic Publishers (1995).

Kramer, E.R. et al., "Activation of the human anaphase-promoting complex by proteins of the CDC20/Fizzy family." *Curr. Biol.* 8:1207-1210, Current Biology Ltd. (1998).

Larsson, J., et al., "Mutations in the *Drosophila melanogaster* Gene Encoding S-adenosylmethionine Suppress Position-Effect Variegation," *Genetics* 143:887-896, The Genetics Society of America (1996).

Lee, I.A., et al., "Cloning and Expression of Human cDNA Encoding Human Homologue of Pituitary Tumor Transforming Gene," *Biochem. Mol. Biol. Intl.* 47:891-897, Taylor & Francis (May 1999).

Lengauer, C., et al., "Genetic instability in colorectal cancers," *Nature* 386:623-627, Nature Publishing Group (1997).

Levine, L.M., et al., "Measurement of Specific Protease Activity Utilizing Fluorescence Polarization," *Anal. Biochem.* 247:83-88, Academic Press (1997).

Lewis, J.D. and Tollervey, D., "Like Attracts Like: Getting RNA Processing Together in the Nucleus," *Science* 288:1385-1389, The American Association for the Advancement of Science (May 2000).

Liang, C. and Stillman, B., "Persistent initiation of DNA replication and chromatin-bound MCM proteins during the cell cycle in *cdc6* mutants," *Genes & Dev.* 11:3375-3386, Cold Spring Harbor Laboratory Press (1997).

Lim H.H. et al., "Cdc20 is essential for the cyclosome-mediated proteolysis of both Pds1 and Clb2 during M phase in budding yeast," *Curr. Biol.* 8:231-234, Current Biology Ltd. (1998).

Locke, J., et al., "Dosage-Dependent Modifiers of Position Effect Variegation in Drosphila and a Mass Action Model That Explains Their Effect," *Genetics* 120:181-198, Genetics Society of America (1988).

Losada, A. et al., "Identification of *Xenopus* SMC protein complexes required for sister chromatid cohesion," *Genes & Dev.* 12:1986-1997, Cold Spring Harbor Laboratory Press (1998).

Matayoshi, E.D., et al., "Novel Fluorogenic Substrates for Assaying Retroviral Proteases by Resonance Energy Transfer," *Science* 247:954-958, The American Association for the Advancement of Science (1990).

Martzen, M.R., et al., "A Biochemical Genomics Approach for Identifying Genes by the Activity of Their Products," *Science* 286:1153-1155, Nature Publishing Group (Nov. 1999).

McGrew, J.T. et al., "Requirement for *ESP1* in the Nuclear Division of *Saccharomyces cerevisiae*," *Mol. Biol. Cell* 3:1443-1454, American Society for Microbiology (1992).

McKay, M.J. et al., "Sequence Conservation of the *rad21 Schizosaccharomyces pombe* DNA Double-Strand Break Repair Gene in Human and Mouse," *Genomics* 36:305-315, Academic Press (1996).

Merdes, A. and De Mey, J., "The mechanism of kinetochore-spindle attachment and polewards movement analyzed in $PtK_2$ cells at the prophase-prometaphase transition," *Eur. J. Cell Biol.* 53:313-325, Wissenschaftliche Verlagsgesellschaft (1990).

Michaelis, C. et al., "Cohesions: Chromosomal Proteins that Prevent Premature Separation of Sister Chromatids," *Cell* 91:35-45, Cell Press (1997).

Milner, C.M., and Campbell, R.D., "The G9a gene in the human major histocompatibility complex encodes a novel protein containing ankyrin-like repeats," *Biochem. J.* 290:811-818, Biochemical Society/Portland Press (1993).

Miyazaki, W.Y. and Orr-Weaver, T.L., "Sister-Chromatid Cohesion in Mitosis and Meiosis," *Annu. Rev. Genet.* 28:167-187, Annual Reviews (1994).

Moore, D.P. et al., "The Cohesion Protein MEI-s332 Localizes to Condensed Meiotic and Mitotic Centromeres until Sister Chromatids Separate," *J. Cell. Biol.* 140:1003-1012, Rockefeller University Press (1998).

Murray, A.W., "Cell Cycle Extracts," *Methods Cell Biol.* 36:581-605, Academic Press (1991).

Murray, M.G., et al., "Inactivation of a yeast transactivator by the fused HIV-1 proteinase: a simple assay for inhibitors of the viral enzyme activity," *Gene* 134:123-128, Elsevier Science Publishers B.V. (1993).

Nagase, T. et al., "Prediction of the Coding Sequences of Unidentified Human Genes. V. The Coding Sequences of 40 New Genes (KIAA0161-KIAA0200) Deduced by Analysis of cDNA Clones from Human Cell Line KG-1," *DNA Res.* 3:17-24, Kazusa DNA Research Institute and Universal Academy Press (1996).

Nasmyth, K., et al., "Splitting the Chromosome: Cutting the Ties That Bind Sister Chromatids," *Science* 288:1379-1384, The American Association for the Advancement of Science (May 2000).

Nicholson, D.W. et al., "Identification and inhibition of the ICE/CED-3 protease necessary for mammalian apoptosis," *Nature* 376:37-43, Nature Publishing Group (1995).

Orlando V., and Paro, R., "Mapping Polycomb-Repressed Domains in the Bithorax Complex Using in Vivo Formaldehyde Cross-Linked Chromatin," *Cell* 75:1187-1198, Cell Press (1993).

Park, I.K., et al., "Interrelationship Between Nuclear Histone Binding and Cell Proliferation," *Int. J. Biochem.* 20:183-187, Pergamon Journals Ltd. (1988).

Pehrson, J.R. and Fried, V.A., "MacroH2A, a Core Histone Containing a Large Nonhistone Region," *Science* 257:1398-1400, American Association for the Advancement of Science (1992).

Peters, J. -M., "SCF and APC: the Yin and Yang of cell cycle regulated proteolysis," *Curr. Opin. Cell Biol.* 10:759-768, Current Biology Publications (1998).

Rastelli, L., et al., "Related chromosome binding sites for *zeste*, suppressors of *zeste* and *Polycomb* group proteins in *Drosophila* and their dependence on *Enhancer of zeste* function," *EMBO J.* 12:1513-1522, Oxford University Press (Apr. 1993).

Rieder, C.L. and Salmon, E.D., "The vertebrate cell kinetochore and its roles during mitosis," *Trends in Cell Biol.* 8:310-318, Elsevier Science Publishers (1998).

Sarubbi, E., et al., "A high throughput assay for inhibitors of HIV-1 protease. Screening of micobial metabolites," *FEBS* 279:265-269, Elsevier Science Publishers B.V. (1991).

Sassone-Corsi, P., et al., "Requirement for Rsk-2 for Epidermal Growth Factor-Activated Phosphorylation of Histone H3," *Science* 285:886-891, American Association for the Advancement of Science (Aug. 1999).

Schotta, G. and Reuter, G., "Controlled expression of tagged proteins in *Drosophila* using a new modular P-element vector system," *Mol. Gen. Genet.* 262:916-920, Springer-Verlag (Jan. 2000).

Singh, J., et al., "Lead Development: Validation and Application of High Throughput Screening for Determination of Pharmacokinetic Parameters for Enzyme Inhibitors," *Bioorg. Med. Chem.* 4:639-643, Pergamon Press (1996).

Smouse, D., and Perrimon, N., "Genetic Dissection of a Complex Neurological Mutant, *polyhomeotic*, in *Drosophila*," *Dev. Biol.* 139:169-185, Academic Press (1990).

Stebbins, J. and Debouck, C., "A Microtiter Colorimetric Assay for the HIV-1 Protease," *Anal. Biochem.* 248:246-250, Academic Press (1997).

Strahl, B.D. and Allis, C.D., "The language of covalent histone modifications," *Nature* 403:41-45, Nature Publishing Group (Jan. 2000).

Sullivan, K.F., et al., "Human CENP-A Contains a Histone H3 Related Histone Fold Domain That is Required for Targeting to the Centromere," *J. Cell Biol.* 127:581-592, The Rockefeller University Press (1994).

Tachibana, M., et al., "SET Domain-containing Protein, G9a, Is a Novel Lysine-preferring Mammalian Histone Methyltransferase with Hyperactivity and Specific Selectivity to Lysines 9 and 27 of Histone H3," *J. Biol. Chem.* 276:25309-25317, The American Society for Biochemistry and Molecular Biology, Inc. (Jul. 2001).

Taliani, M., "A Continuous Assay of Hepatitis C Virus Protease Based on Resonance Energy Transfer Depsipeptide Substrates," *Anal. Biochem.* 240:60-67, Academic Press (1996).

Turner, B.M., "Histone acetylation as an epigenetic determinant of long-term transcriptional competence," *Cell. Mol. Life Sci.* 54:21-31, Birkhauser Verlag (1998).

Uhlmann, F., et al., "Cleavage of Cohesion by the CD Clan Protease Separin Triggers Anaphase in Yeast," *Cell* 103:375-386, Cell Press (Oct. 2000).

Uhlmann, F., et al., "Sister-chromatid separation at anaphase onset is promoted by cleavage of the cohesion subunit Scc1," *Nature* 400:37-42, Nature Publishing Company (Jul. 1999).

Uhlmann, F. and Nasmyth, K., "Cohesion between sister chromatids must be established during DNA replication," *Curr. Biol.* 8:1095-1101, Cell Press (1998).

Vigil, P. and Bustos-Obregon, E., "Alkylating Agents and Mouse Spermatogenesis: Effects of a Single Dose of Cyclophosphamide," *Andrologia* 17:276-282, Grosse-Verlag (1985).

Waizenegger, I.C., "Two Distinct Pathways Remove Mammalian Cohesion from Chromosome Arms in Prophase and from Centromeres in Anaphase," *Cell* 103:399-410, Cell Press (Oct. 2000).

Wei, Y., et al., "Phosphorylation of Histone H3 is Required for Proper Chromosome Condensation and Segregation," *Cell* 97:99-109, Cell Press (Apr. 1999).

Working, P.K., "Male Reproductive Toxicology: Comparison of the Human to Animal Models," *Environ. Health Perspect.* 77:37-44, U.S. Department of Health and Human Services (1988).

Xu, X., et al., "Centrosome Amplification and a Defective $G_2$-M Cell Cycle Checkpoint Induce Genetic Instability in BRCA1 Exon 11 Isoform-Deficient Cells," *Mol. Cell* 3:389-395, Cell Press (Mar. 1999).

Zhang, X., et al., "Pituitary Tumor Transforming Gene (PTTG) Expression in Pituitary Adenomas," *J. Clin. Endocrin. Metab.* 84:761-767, The Endocrine Society (Feb. 1999).

Zheng, Q., et al., "Expression, Purification, and Characterization of Recombinant Ribulose-1, 5-Bisphosphate Carboxylase/Oxygenase Large Subunit $N^\epsilon$-Methyltransferase," *Protein Express. Purif.* 14:104-112, Academic Press (1998).

Zimmerman, M., et al., "Sensitive Assays for Trypsin, Elastase, and Chymotrypsin Using New Fluorogenic Substrates," *Anal. Biochem.* 78:47-51, Academic Press (1977).

Zou, H. et al., "Identification of a Vertebrate Sister-Chromatid Separation Inhibitor Involved in Transformation and Tumorigenesis," *Science* 285:418-422, American Association for Advancements of Science (Jul. 1999).

GenBank Report for Accession No. D79987, from Nagase T., et al. (last updated Jan. 2004).

GenBank Report for Accession No. L08238, from Geraghty, M.T. (last updated 1995).

GenBank Report for Accession No. U18003, from Ostermeyer, E.A. (last updated 1998).

GenBank Report for Accession No. AAC29137, from Ying, Z. et al. (last updated Dec. 1999).

GenBank Report for Accession No.AAD39289, from Federspiel, N.A. et al. (last updated Oct. 2002).

GenBank Report for Accession No. D31891, from Nomura, N. (last updated Jan. 2004).

GenBank Report for Accession No. U52965, from Hobert, O. (last updated 1996).

International Search Report for International Patent Application No. PCT/EP00/01183, mailed Jun. 29, 2000.

Dialog File 351, Accession No. 1996-518672, WPI English language abstract of DE 19516776 (Document AM1).

Co-Pending U.S. Appl. No 10/773,302, Jenuwein et al., filed Feb. 9, 2004 (Not Published).

U.S. Appl. No. 09/500,991, Uhlmann et al., filed on Feb. 15, 2000 (Not Published).

U.S. Appl. No. 09/589,892, Jenuwein et al., filed on Jun. 9, 2000 (Not Published).

* cited by examiner

FIG. 1A

```
    *
  1 tgaccgcgcagtttgaatgaaagctccgcaagATGGCGACGGCCAGGGCCAAGGCAGG    60  (SEQ ID NO:1)
                                   M  A  T  A  R  A  K  A  R      9  (SEQ ID NO:2)
 61 GGCAGTGAGGCAGGAGCGCGGGTGTCACCGGCTGTCCAGTCCCGCCCCCGAGGCCAAGGCC 120  (SEQ ID NO:1)
     G  S  E  A  G  A  R  C  H  A  P  G  P  P  P  P  K  A         29  (SEQ ID NO:2)
121 AGGCGAACGGCGAGACGCGCGGCGGAGACCCTGACGGCGCGAGCTCGCGGCCGTCT       180  (SEQ ID NO:1)
     R  T  A  R  A  E  T  L  T  A  R  S  R  P  S                  49  (SEQ ID NO:2)
181 GCGGGGCGAGAGGCGCGGCTCCCCAGCAGCGTGGTCCGGAGCGTGGGCGCGGTC        240  (SEQ ID NO:1)
     A  G  E  R  A  G  S  Q  R  A  W  S  G  A  P  R  A  A  V     69  (SEQ ID NO:2)
241 TTTGGCGACGAGTGTGCAGAGGTGCACGCCTTATTCAAGGCCTGGTGTGCCTTGCCTAGTT 300  (SEQ ID NO:1)
     F  G  D  E  C  A  R  G  A  L  F  K  A  W  C  V  P  C  L  V   89  (SEQ ID NO:2)
301 TCACTTGATATACTCTCCAGAGGAATTATGAGGTGCGCAAGAAAGCTCACATGTAAATCGATTGGA 360  (SEQ ID NO:1)
     S  L  D  T  L  Q  E  L  C  R  R  E  K  L  T  C  K  S  I  G  109 (SEQ ID NO:2)
361 ATCACCAAAAGGAATCTAAACAATTATGAGGTGGAGTACTTGTGTGACTACAAGGTAGCA 420  (SEQ ID NO:1)
     I  T  K  R  N  L  N  N  Y  E  V  E  Y  L  C  D  Y  K  V  A  129 (SEQ ID NO:2)
421 AAGGGTGTGGAATATTATCTTGTAAAATGGAAAGGATGGCCAGATTCTACAAACACCTGG 480  (SEQ ID NO:1)
     K  G  V  E  Y  Y  L  V  K  W  K  G  W  P  D  S  T  N  T  W  149 (SEQ ID NO:2)
481 GAGCCCTTGAGAAACCTCAGGTGTCCACAGCTCCTGCGGCAGTTCTCTGATGACAAGAAG 540  (SEQ ID NO:1)
     E  P  L  R  N  L  R  C  P  Q  L  L  R  Q  F  S  D  D  K  K  169 (SEQ ID NO:2)
```

| | | |
|---|---|---|
| 541 | ACTTACTTAGCTTCAGGAAAGGAAATGCAAGGCTGTCAATTCAAAATCCTTGCAACCTGCA<br>T Y L A Q E R K C K A V N S K S L Q P A | 600 (SEQ ID NO:1)<br>189 (SEQ ID NO:2) |
| 601 | ATTGCTGAGTATATTGTACAGAAAGCTAAGCAAAGAATAGCTCTGCAGAGATGGCAAGAT<br>I A E Y I V Q K A K Q R I A L Q R W Q D | 660 (SEQ ID NO:1)<br>209 (SEQ ID NO:2) |
| 661 | TACCTCAACAGAAGAAAAGAACCATAAGGGATGATATTTGTTGAAAACACTGTTGACTTG<br>Y L N R R K N H K G M I F V E N T V D L | 720 (SEQ ID NO:1)<br>229 (SEQ ID NO:2) |
| 721 | GAGGGCCCACCTTTAGACTTCTACTACATTAACGAGTACAGGCCCAGCTCCCGGGATCAGC<br>E G P P L D F Y Y I N E Y R P A P G I S | 780 (SEQ ID NO:1)<br>249 (SEQ ID NO:2) |
| 781 | ATAAACAGTGAAGCCACCTTTGGAT GTTCAT GTACAGACTGCTTCTTTGACAAGTGTTGT<br>I N S E A T F G (C) S (C) T D (C) F F D K (C) C | 840 (SEQ ID NO:1)<br>269 (SEQ ID NO:2) |
| 841 | CCTGCTGAAGCTGGAGTTGTGTTGGCTTATAATAAGAAGCAACAAATTAAAATCCAACCA<br>P A E A G V V L A Y N K K Q Q I K I Q P | 900 (SEQ ID NO:1)<br>289 (SEQ ID NO:2) |
| 901 | GGCACTCCCCATCTACGAATGCAACTCAAGGTGTCGATGTGGACCTGAATGTCCCAATAGG<br>G T P I Y E (C) N S R (C) R (C) G P E (C) P N R | 960 (SEQ ID NO:1)<br>309 (SEQ ID NO:2) |

```
961  ATTGTACAAAAGGCACACAATATTCACTGTGCATCTTTAAAACTAGCAATGGCTGTGGT        1020 (SEQ ID NO:1)
      I V Q K G T Q Y S L C I F K T  S N G C G                          329  (SEQ ID NO:2)
1021 TGGGGTGTAAAAACCCTTGTGAAGATTAAGAATGAGTTTGTCATGGAATATGTTGGA         1080 (SEQ ID NO:1)
      W G V K T L V K I K R M S F V M E Y V G                            349  (SEQ ID NO:2)
1081 GAGGTGATCACAAGTGAAGAGGCCCGAGAGAGGGGACAGTTCTATGACAACAAAGGATC       1140 (SEQ ID NO:1)
      E V I T S E E A E R R G Q F Y D N K G I                            369  (SEQ ID NO:2)
1141 ACCTACCTCTTTGACCTGGACTACGAGTCTGATGAGTTCACAGTGGATGCAGCTCGATAT      1200 (SEQ ID NO:1)
      T Y L F D L D Y E S D E F T V D A A R Y                            389  (SEQ ID NO:2)
1201 GGAAACGTATCCCATTTTGTGAATCATAGTCGGCTGCCCAGGATAGCACATTGTTCTCAGGTGTTAGTGTT 1260 (SEQ ID NO:1)
      G N V S H F V N H S C D P N L Q V F S V                            409  (SEQ ID NO:2)
1261 GGAAACGTATCCCATTTTGTGAATCATAGTCGGCTGCCCAGGATAGCACATTGTTCTCTACAAGAACCATA 1320 (SEQ ID NO:1)
      F I D N L D T R L P R I A L F S T R T I                            429  (SEQ ID NO:2)
1321 AACGCTGGAGAAGAGCTGACTTTTGACTATCAAATGAAAAGGGTTCTGGAGAAGCATCTTCA    1380 (SEQ ID NO:1)
      N A G E E L T F D Y Q M K G S G E A S S                            449  (SEQ ID NO:2)
1381 GACTCCATTGACCACAGCCCTGCCAAAAAAAGGGTCAGAACCCAATGTAAATGTGGACGCC    1440 (SEQ ID NO:1)
      D S I D H S P A K K R V R T Q C K C G A                            469  (SEQ ID NO:2)
1441 GAGACTTGCAGAGGTTACCTCAACTGAagtgtcgggaaacg                          1481 (SEQ ID NO:1)
      E T C R G Y L N                                                    477  (SEQ ID NO:2)
```

Fig. 8
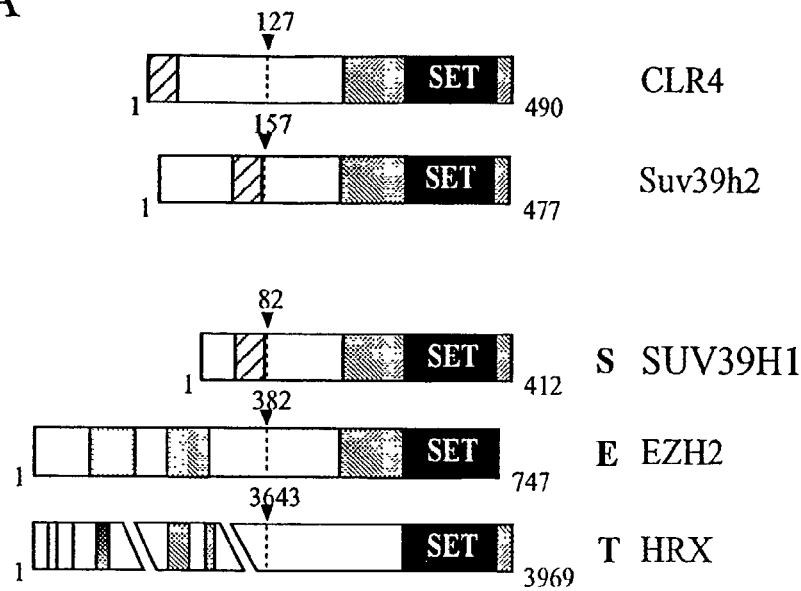
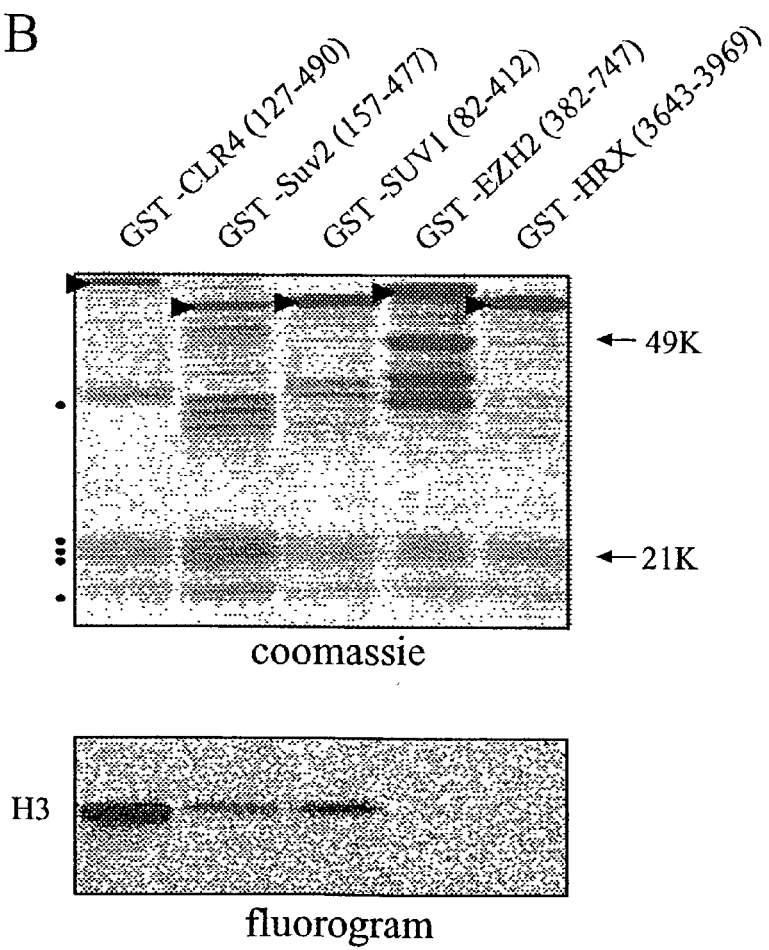

Northern analysis wt          null

Sp Li Ki Br  Sp Li Ki Br 2.9 kb —     Suv39h1

GAPDH

Fig. 9C
C
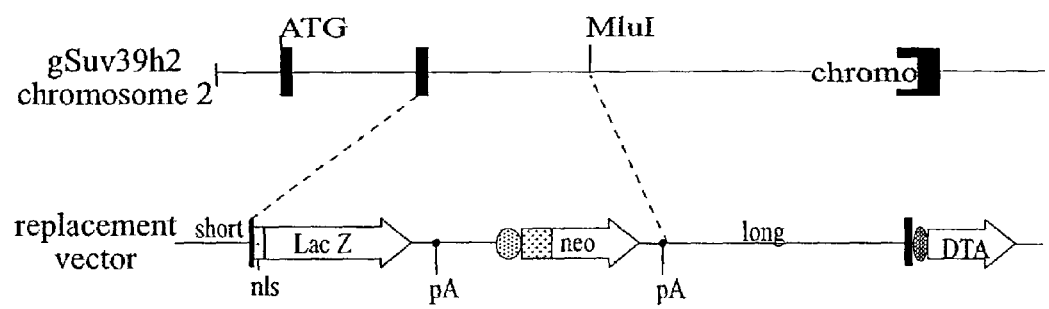
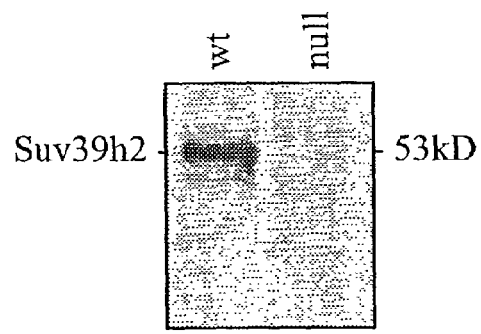
Western analysis
(testis extracts)

Fig. 10
A
wt double null
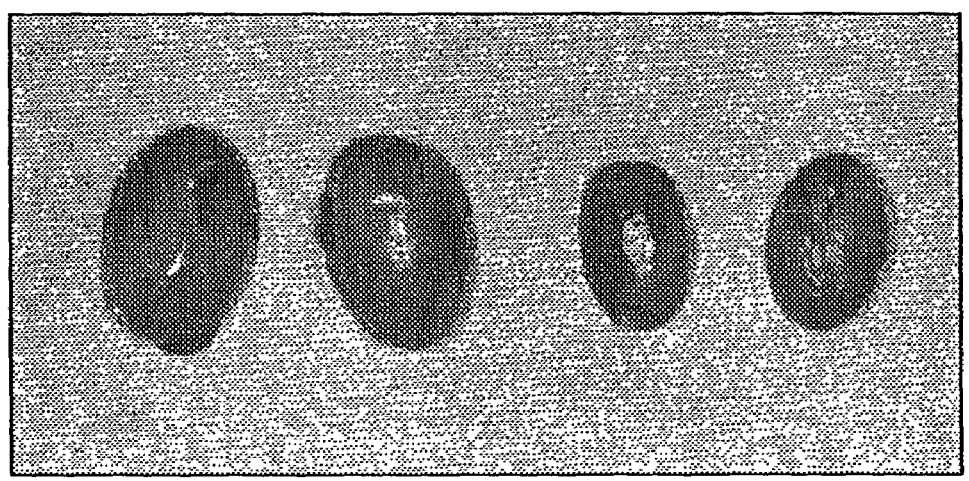
B
wt double null
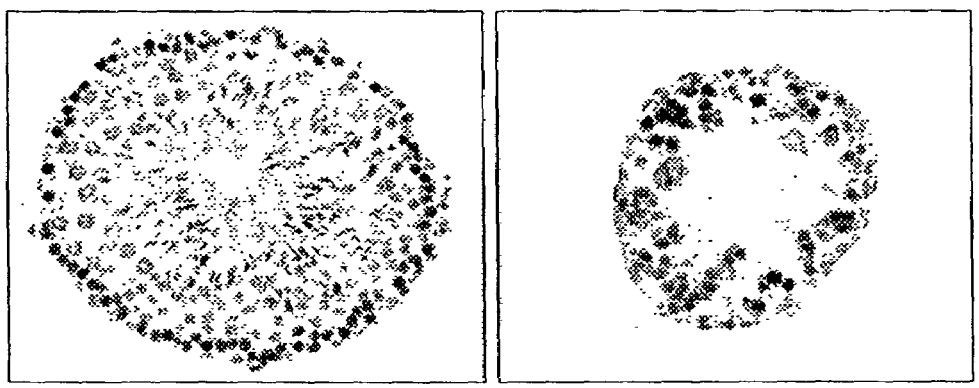

Fig. 11A
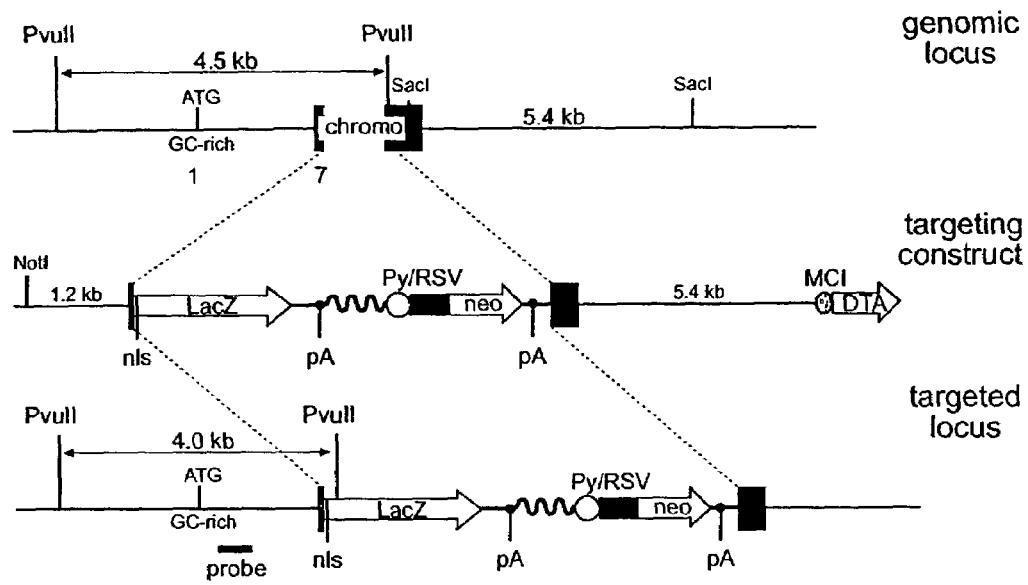
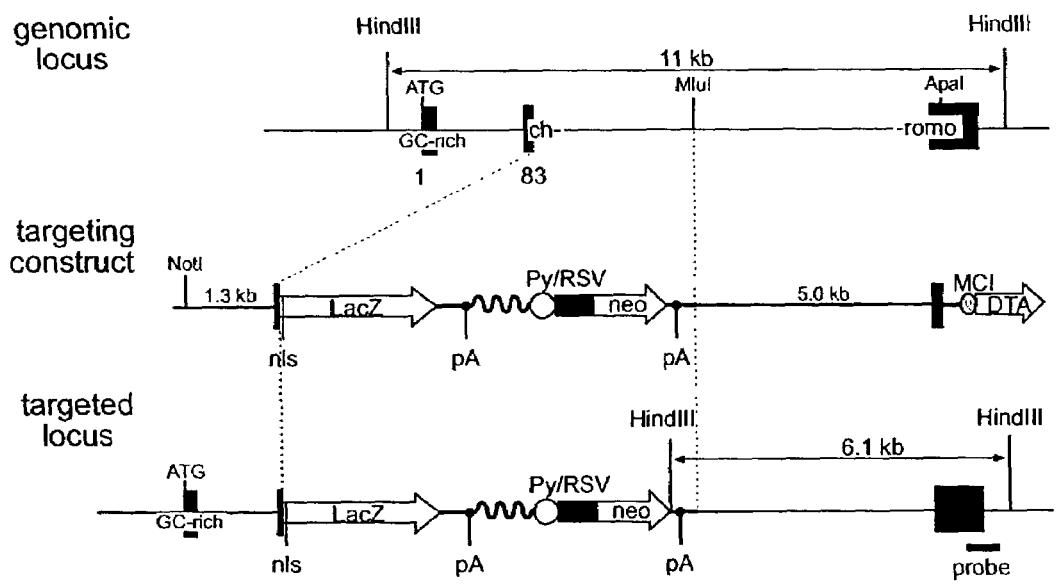

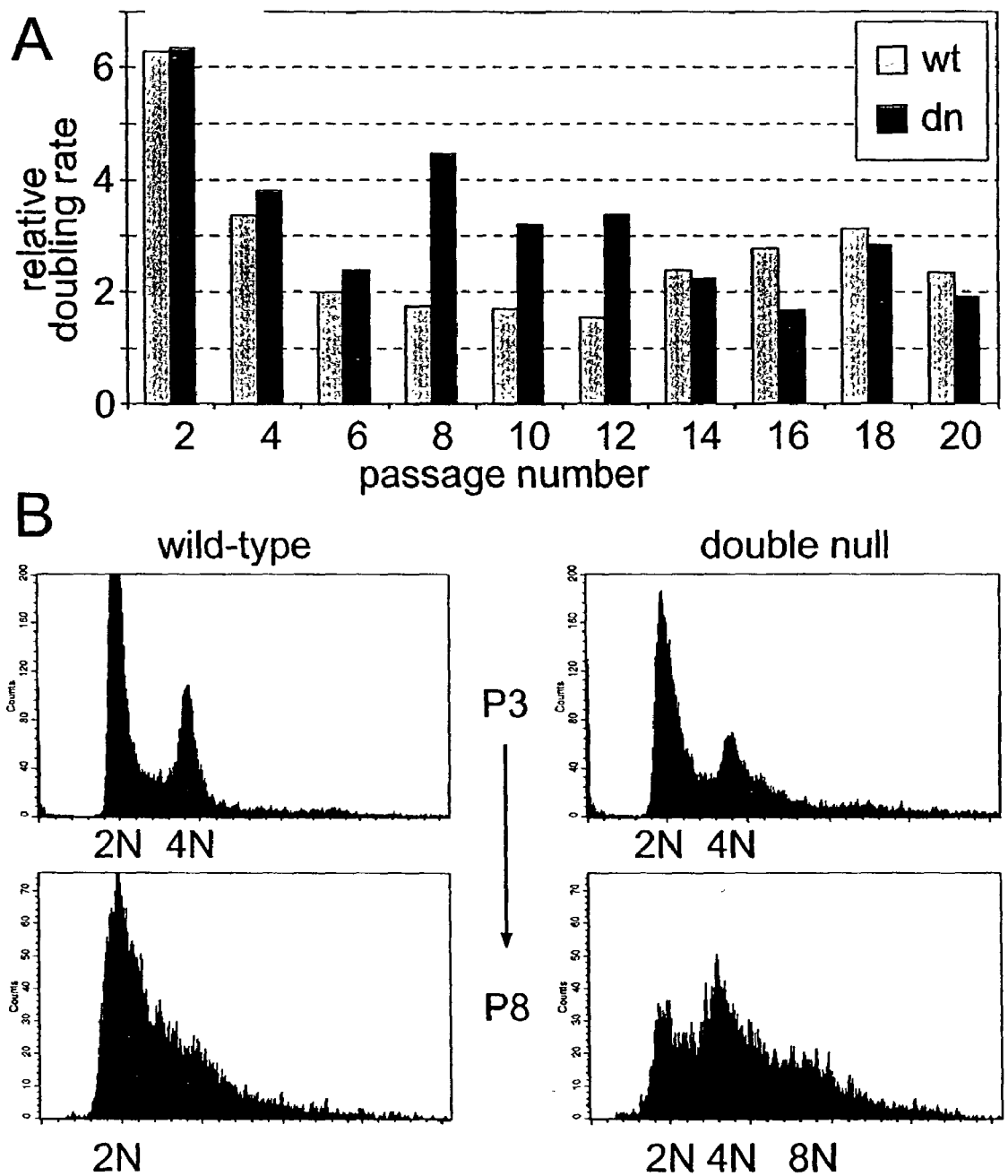
Fig. 12A,B

Fig. 13A,B
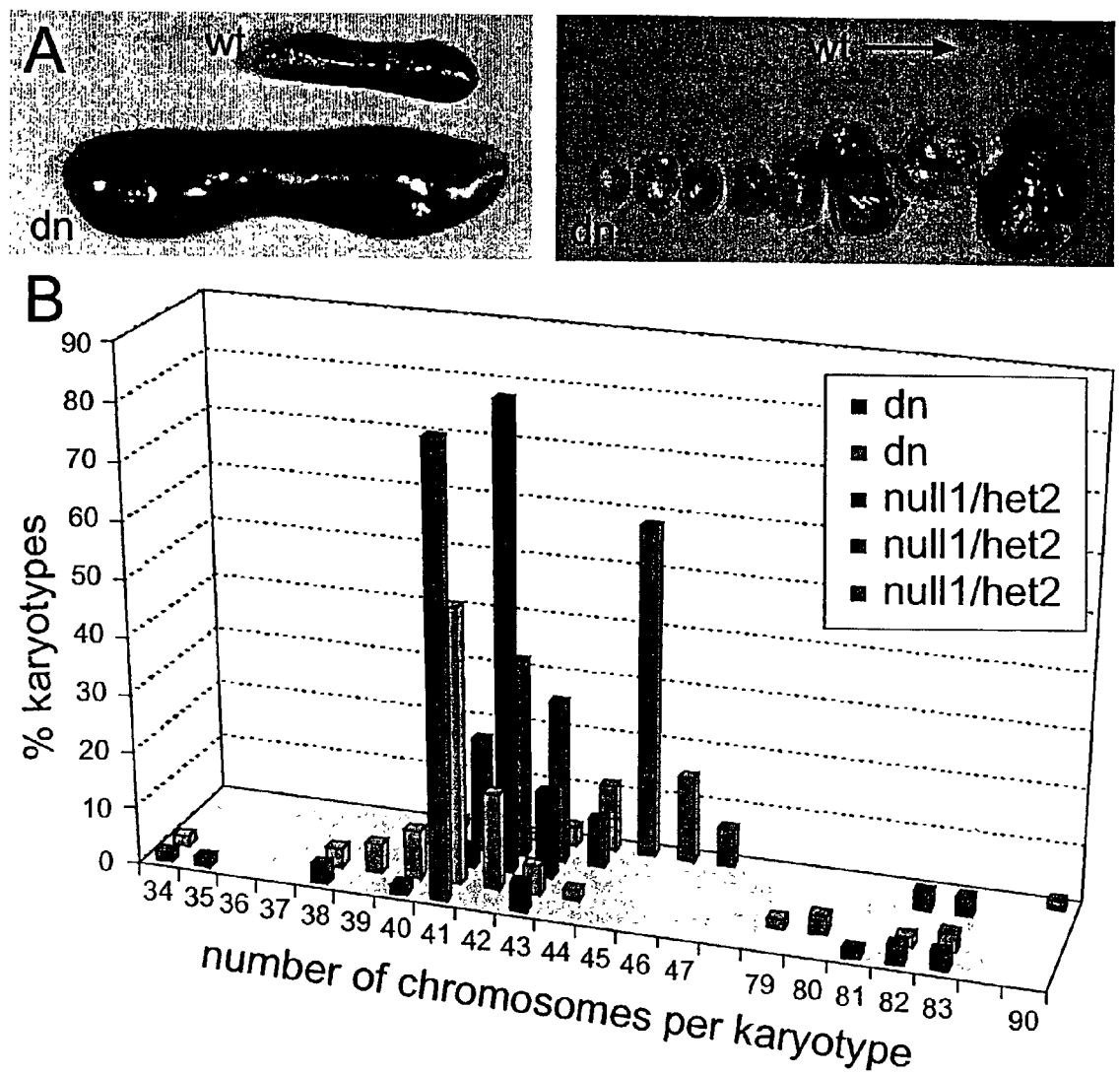

Fig. 16 A-C
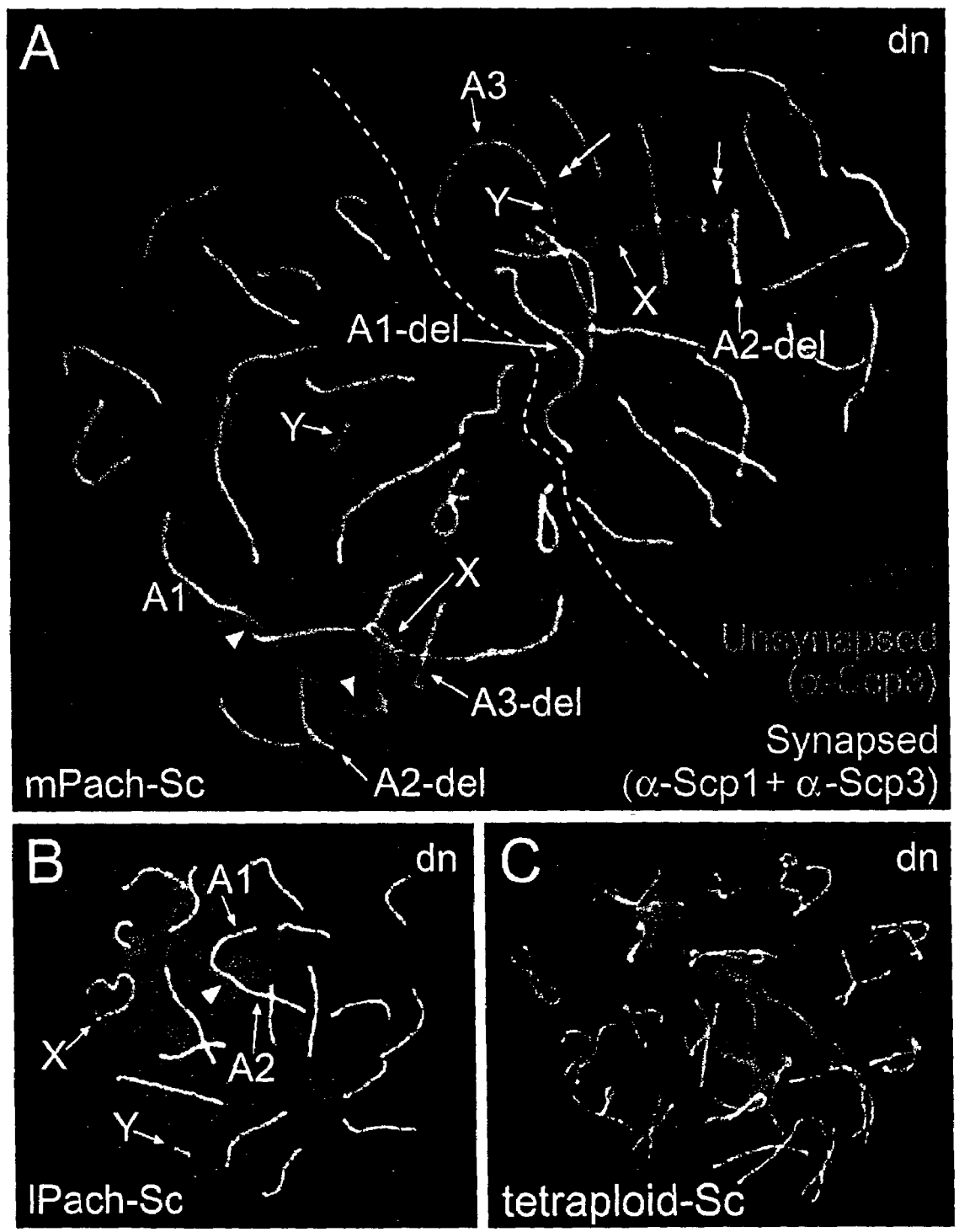

Fig. 16 D-I
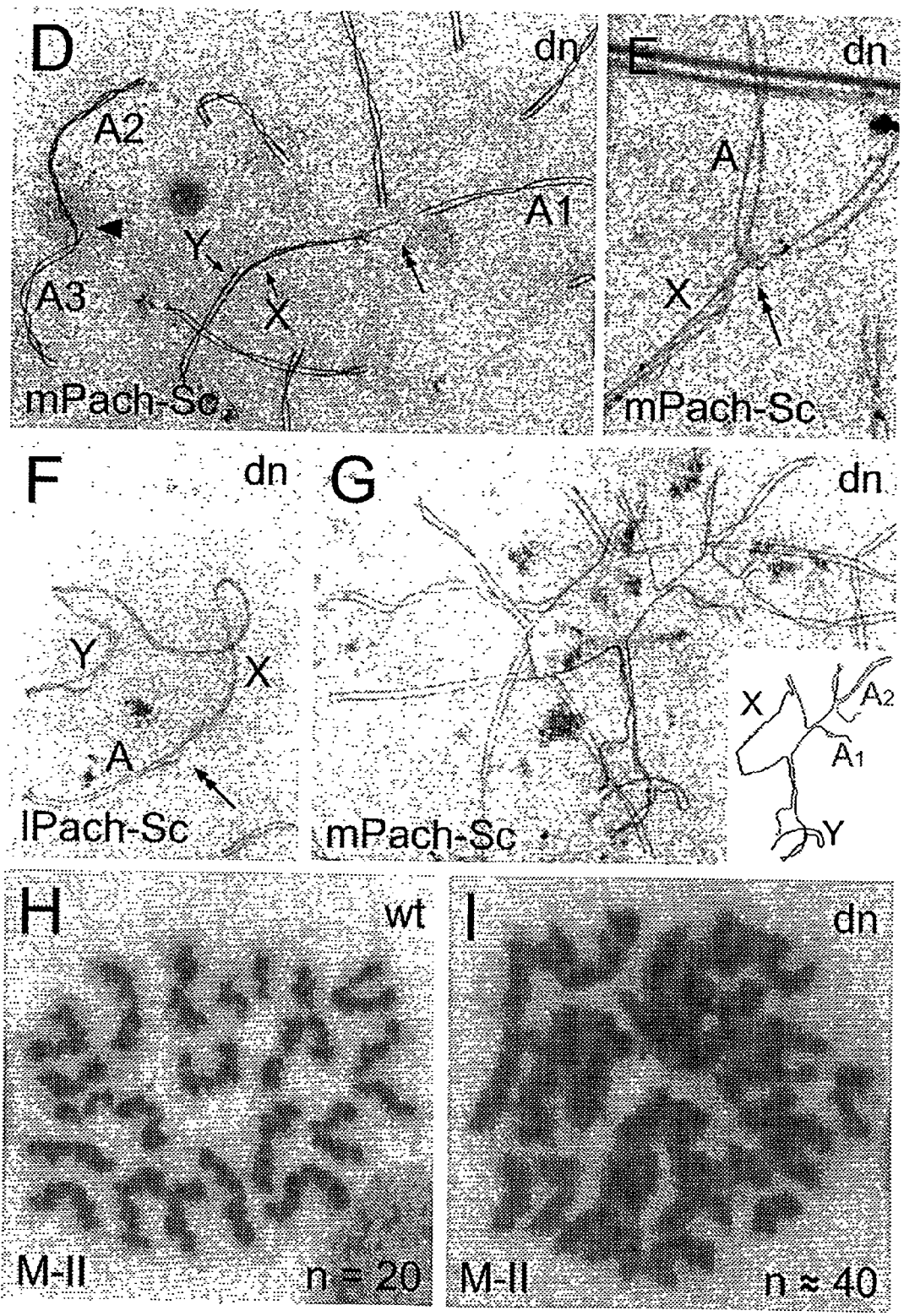

Fig. 16 J,K
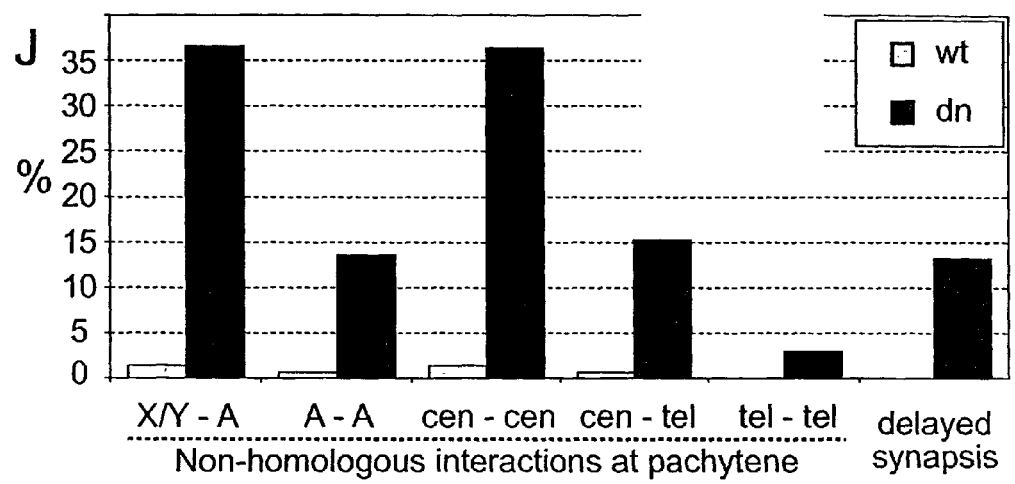
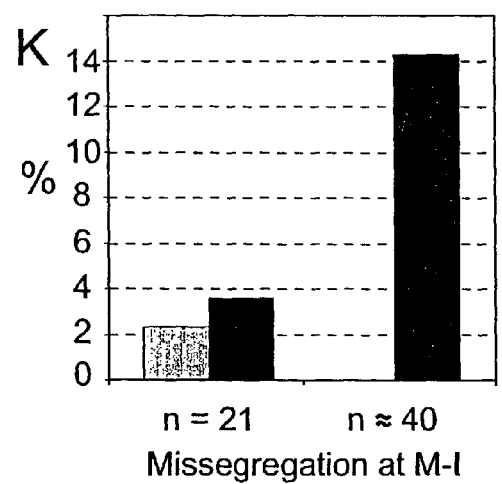

Fig. 17 A-D
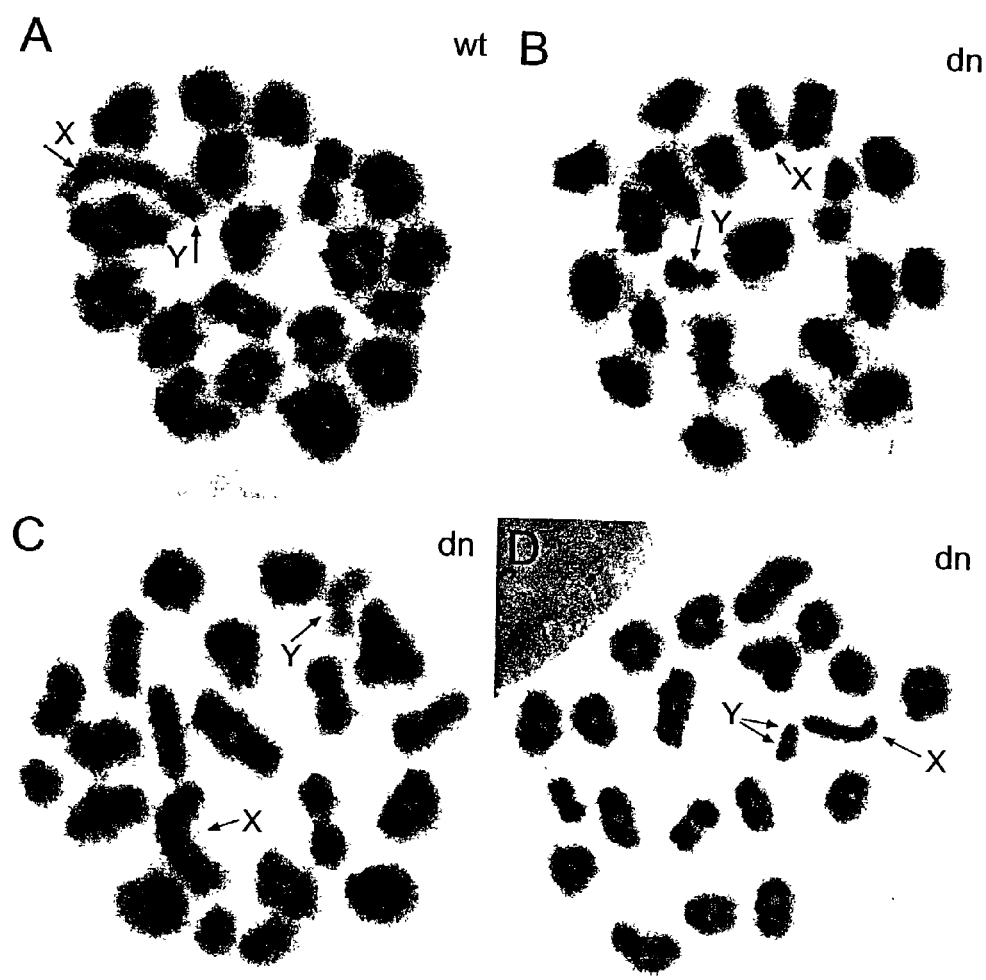

Fig. 17 E,F
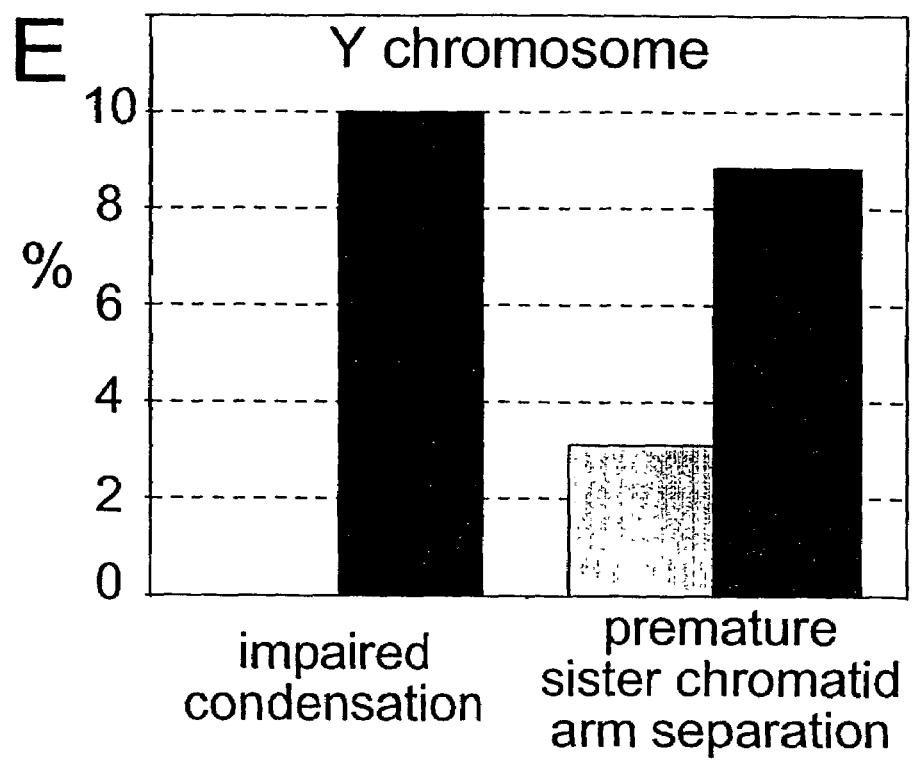
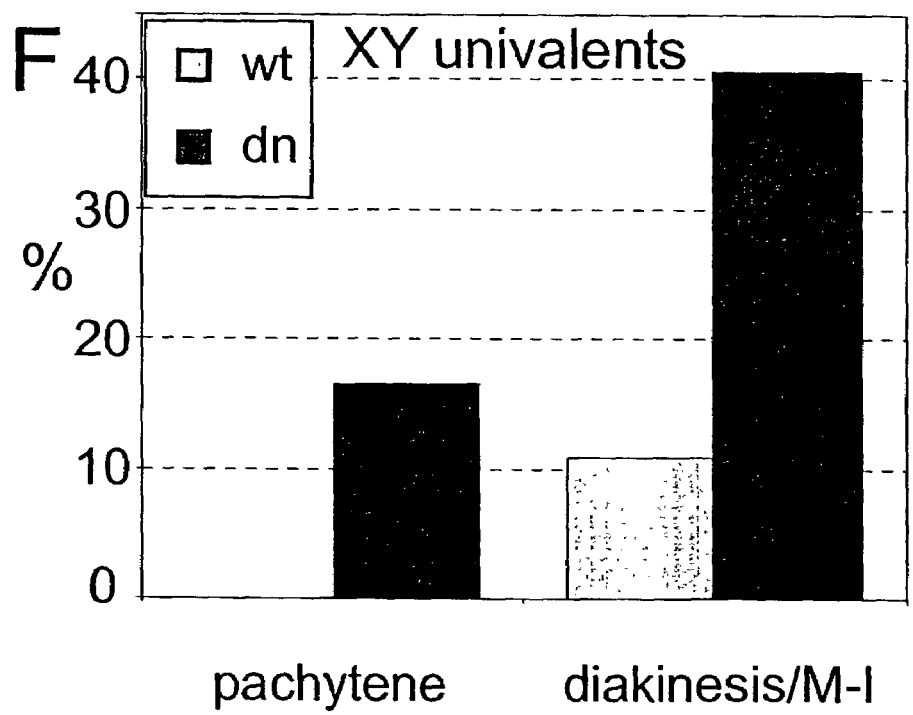

Fig. 18/1
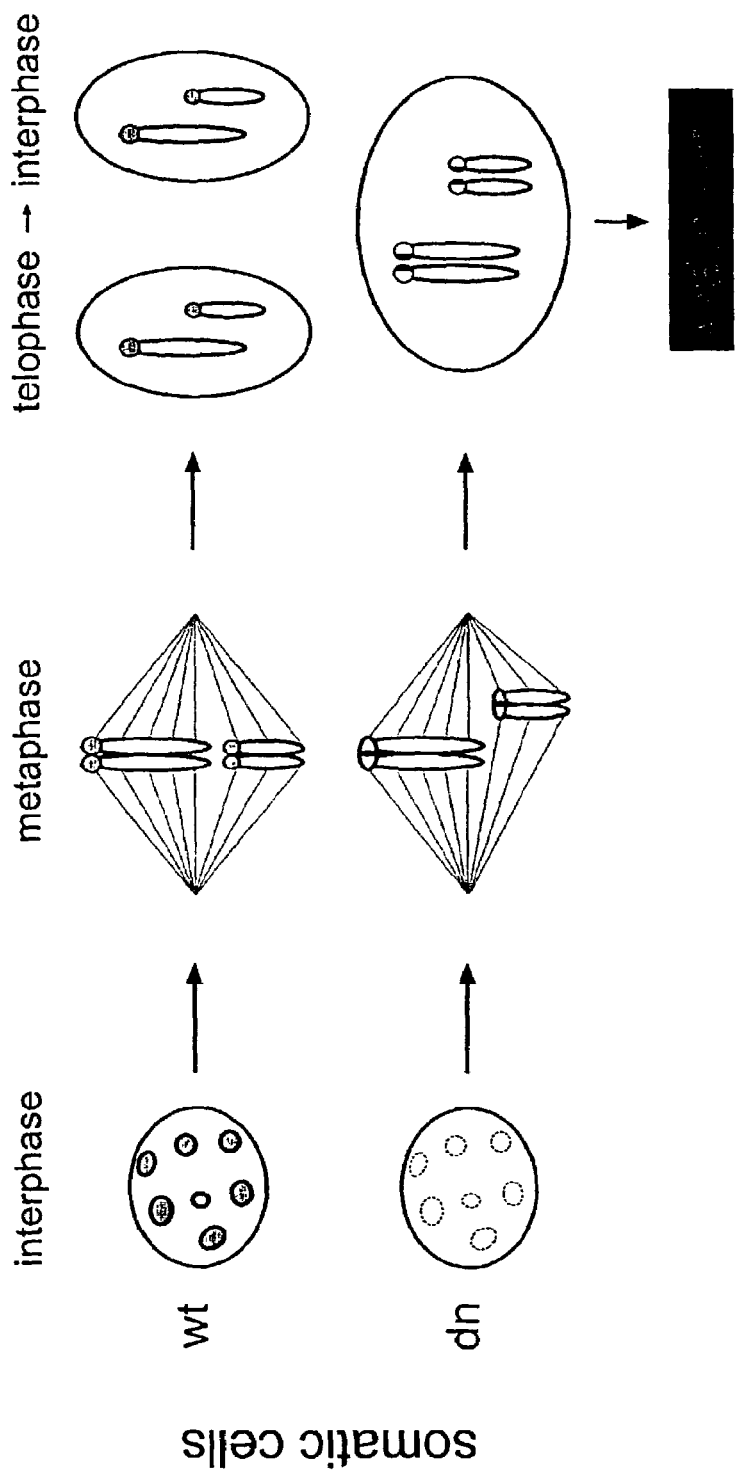

Fig. 18/2
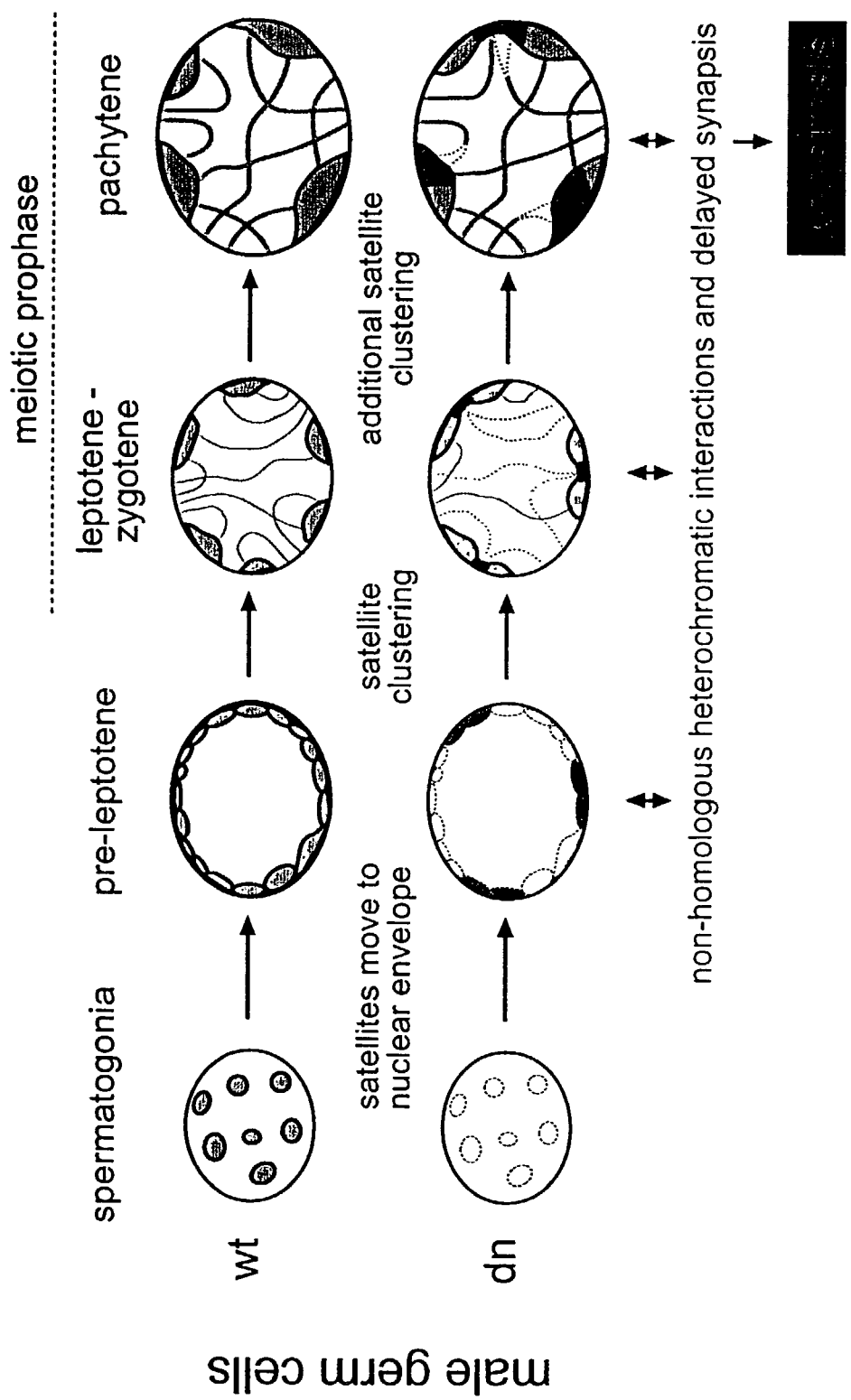

MAMMALIAN SUV39H2 PROTEINS AND ISOLATED DNA MOLECULES ENCODING THEM

CROSS REFERENCE TO RELATED APPLICATIONS

This application is a divisional of U.S. application Ser. No. 09/876,224, filed Jun. 8, 2001 now abandoned, which is herein incorporated by reference in its entirety; said U.S. application Ser. No. 09/876,224 claims priority benefit of U.S. Provisional Application No. 60/224,173, filed Aug. 9, 2000, which is herein incorporated by reference in its entirety.

BACKGROUND OF THE INVENTION

1. Field of the Invention

The invention relates to the isolation and functional characterisation of a novel mammalian Su(var)3-9 homologue, Suv39h2, and its use.

2. Related Art

In eukaryotes, control of gene expression and the functional organisation of chromosomes depends on higher-order chromatin (Paro and Harte, 1996; Karpen and Allshire, 1997). In addition to its role in somatic cells, higher-order chromatin is also involved in chromosomal dynamics during meiosis (Dernburg et al., 1996). Although condensation and pairing of meiotic chromosomes is evolutionarily highly conserved, meiosis in male mammals is exceptional because the heteromorphic X and Y chromosomes undergo facultative heterochromatinisation that is accompanied by transcriptional silencing (Handel and Hunt, 1992). This selective inactivation of the male sex chromosomes, which is cytologically defined by the appearance of the so-called XY body or sex vesicle (Solari, 1974), has been proposed to restrict promiscuous pairing or recombination between non-homologous chromosomes, thereby reducing the risk for aneuploidy (Handel and Hunt, 1992). In fact, failure to form this specialised chromatin structure in the XY body prevents successful spermatogenesis (Kot and Handel, 1990; Matsuda et al., 1991).

Su(var) genes were initially identified by genetic screens on centromeric position effects in *Drosophila melanogaster* (Reuter and Spierer, 1992) and *Schizosaccharomyces pombe* (Allshire et al., 1995). Since Su(var) genes suppress position effect variegation (PEV), their gene products have been implicated in the organisation of repressive chromatin domains (Henikoff, 1997). Indeed, isolated family members encode either chromosomal proteins or enzymes that can modify chromatin (Wallrath, 1998).

*Drosophila* Su(var)3-9 and its *S.pombe* clr4 homologue are the only modifying loci whose gene products combine the characteristic chromo and SET domains. Whereas the 60 amino acid chromo domain (Paro and Hogness, 1991; Aasland and Stewart, 1995; Koonin et al., 1995) represents a protein-specific interaction surface (Messmer et al., 1992; Platero et al., 1995) that resembles an ancient histone-like fold (Ball et al., 1997), the structure of the 130 amino acid SET domain (Jenuwein et al., 1998) is currently undefined. However, it has recently been shown that the SET domain of Suv39h1 harbours an intrinsic histone methyltransferase HMTase activity, which is specific for lysine 9 of histone H3 (Rea et al., 2000). These data suggest that Suv39h homologues exert their function through the organisation chromatin structure via histone H3 methylation.

The corresponding mouse (Suv39h1) and human (SUV39H1) Su(var)3-9 homologues have been identified and it has been demonstrated that SUV39H1 represents a functional mammalian homologue of Su(var)3-9 in transgenic flies (Aagaard et al., 1999). Immunolocalisation of endogenous Suv39h1 or SUV39H1 proteins in mammalian cells indicated enriched distribution at heterochromatic foci during interphase and transient accumulation at centromeric positions during mitosis (Aagaard et al., 2000). In addition, Suv39h1 or SUV39H1 associate with M31 (HP1β), one mammalian homologue of *Drosophila* HP1, indicating the existence of a mammalian SU(VAR) protein complex(es) (Aagaard et al., 1999). Moreover, deregulated SUV39H1 can induce ectopic heterochromatin and redistribute endogenous M31 (HP1β) (Melcher et al., 2000). These data defined Suv39h1 or SUV39H1 as novel heterochromatic HMTase proteins that are involved in the structural organisation of mammalian higher-order chromatin in somatic cells.

SUMMARY OF THE INVENTION

It was the object of the invention to identify other mammalian Su(var)3-9 homologues and to investigate their function through gene expression, protein immunolocalisation analysis and gene disruption techniques in the mouse.

To solve the problem underlying the present invention, the following approaches were taken.

To identify additional mammalian Su(var)3-9 homologues, sequence similarity searches (Bassett et al., 1995; Altschul et al., 1997) with the murine Suv39h1 or human SUV39H1 cDNAs (Aagaard et al., 1999) revealed the presence additional Su(var)3-9 homologue. In analogy to Suv39h1, this novel gene was designated Suv39h2 (for Su(var)3-9 homologue 2). The nucleotide sequence (~1.5 kb) and conceptional reading frame (477 amino acids) of the composite coding Suv39h2 cDNA is (SEQ ID NO:1) shown in FIG. 1A–1C.

Cross-species comparison of Suv39h2 with Suv39h1 or other representative members of the SU(VAR)3-9 protein family, like *Drosophila* SU(VAR)3-9 (Tschiersch et al., 1994), *S.pombe* CLR4 (Ivanova et al., 1998) and a putative open reading frame (ORF) in *C.elegans* (C15H11.5) indicate very similar sequence identities and phylogenetic relationships (FIG. 2).

To determine the size of Suv39h2 mRNAs, RNA blots containing total RNA from embryonic stem cells (ES-cells) and mouse embryos from various stages (day E10.5–day E17.5) of embryogenesis and postnatal (P1–P4) development were hybridized with a 980 bp cDNA probe comprising Suv39h2 coding sequences (amino acids 143–477) and a near full length Suv39h1 cDNA probe. Within this region, the Suv39h2 cDNA is approximately 60% identical to the Suv39h1 nucleotide sequence and does not cross-hybridize with Suv39h1 transcripts (see FIG. 3). This Suv39h2-specific cDNA probe detected a prominent mRNA of approximately 2.7 kb in most RNA preparations of the analyzed stages (FIG. 3, middle panel). The size of the great majority of Suv39h2 transcripts agrees with a 2.7 kb mRNA also found in several mouse and human cell lines, whereas only at day E10.5, smaller-sized (1.7 kb) transcripts were detected.

Expression analysis of both Suv39h1 and Suv39h2 revealed potential overlapping functions during embryogenesis. Northern blot and whole-mount RNA in situ analysis were used to determine the embryonic expression profiles of Suv39h1 and Suv39h2. Both genes are ubiquitously expressed during embryogenesis.

Expression analysis revealed potential distinct functions for both Suv39h1 and Suv39h2 in the adult mouse. In contrast to embryonic expression profiles, abundance of Suv39h2 and Suv39h1 transcripts greatly differs in adult tissues. Whereas Suv39h1 displays broad expression in a panel of RNA preparations comprising 14 adult tissues, expression of Suv39h2 remains largely restricted to testes, with mRNAs being present as 2.7 kb and 1.7 kb transcripts.

To characterize Suv39h2 expression at a biochemical level, a polyclonal rabbit antiserum that was raised against a recombinant glutathione S-transferase (GST) fusion protein comprising amino acids 157–477 of murine Suv39h2 was generated. The anti-Suv39h2 antibodies recognize an endogenous protein of approximately 53 kDa in both PMEFs and testis. The size of the endogenous Suv39h2 protein is in good agreement with the gene product predicted from the coding sequence of the Suv39h2 cDNA (SEQ ID NO:1) (see FIG. 1A–1C).

In order to elucidate a potential function for Suv39h2 in male gametogenesis, the subnuclear localisation endogenous Suv39h2 protein in nuclei of testis swab preparations was analyzed (see Materials and Methods) by indirect immunofluorescence with the anti-Suv39h2 antibodies. Suv39h2 is a component of meiotic heterochromatin and the XY body during mid pachytene.

To demonstrate the specific accumulation of Suv39h2 with the sex chromosomes, double immunofluorescence analyses for Suv39h2 and SCP3, for Suv39h2 and Xmr, and for Suv39h2 and H1t was performed. These analyses revealed specific association of Suv39h2 with sex chromosomes from mid-late pachytene to diplotene.

It has been shown in parallel experiments that the SET domain of Suv39h1 harbours an intrinsic HMTase activity. It was therefore analyzed whether other SU(VAR)3-9 family members, in particular Suv39h2, or other SET domain proteins exhibit HMTase activity. GST-fusion products of the extended SET domains of murine Suv39h2, S.pombe CLR4 (Ivanova et al., 1998), human EZH2 (Laible et al., 1997) and human HRX (Tkachuk et al., 1992) were generated that would correspond to GST-SUV39H1(82–412) and HMTase activity assayed. Interestingly, GST-Suv39h2 (157–477) and GST-CLR4(127–490) also displayed HMTase activity. These data identify Suv39h2 as a novel component of meiotic chromatin, the XY body and as a meiotic histone H3 MTase.

After having identified Suv39h1 and Suv39h2 as mammalian histone H3 lysine 9 specific histone methyltransferases (Suv39h HMTases), it was shown that these HMTases are heterochromatin-enriched enzymes which transiently accumulate at centromeres during mitosis (Aagaard et al., 1999; Aagaard et al., 2000). Moreover, it was shown that methylation of histone H3 at lysine 9 (H3-K9) creates a high-affinity binding site for HP1 proteins (Lachner et al., 2001; Bannister et al., 2001), thereby defining the SUV39H1-HP1 methylation system as a crucial regulatory mechanism for the assembly and propagation of heterochromatin (Jenuwein, 2001). Overexpression of human SUV39H1 induces ectopic heterochromatin and results in chromosome mis-segregation in mammalian cell lines (Melcher et al., 2000).

In addition to the essential mitotic functions described above, heterochromatin is also crucial for the dynamic reorganization of meiotic chromosomes. Meiosis is initiated by chromosomal movements from the nuclear lumen to the nuclear envelope, where chromosomes cluster via their pericentric satellite sequences (Hawley et al., 1992; Scherthan et al., 1996). At meiotic prophase, chromosomes condense, followed by homolog pairing and recombination (at pachytene) between maternal and paternal chromosomes. The onset of the meiotic divisions is preceded by desynapsis, further chromosome condensation and histone H3 phosphorylation at pericentric heterochromatin (Cobb et al., 1999). In particular for male germ cells, the haploid genome content is finally organized into one heterochromatic block in elongating spermatids. In Drosophila, heterochromatin and its associated satellite sequences have been proposed to assist in the initial meiotic chromosome movements and in homolog pairing by orienting chromosomes along a similar higher-order structure (Hawley et al., 1992; Karpen et al., 1996; Dernburg et al., 1996b). In germ cells of mammals, a pachytene checkpoint (de Vries et al., 1999) monitors misaligned and unpaired chromosomes and arrests cells in meiotic prophase, thereby preventing the production of aneuploid gametes.

It was a further object of the invention to analyse the role of Suv39h1 and Suv39h2 in embryonic development and in spermatogenesis in view of utilizing these proteins as drug targets for conditions involving fertility, in particular male fertility.

To investigate the in vivo significance of Suv39h function, in particular Suv39h2 function, in male gametogenesis, mouse strains deficient for both Suv39h1 and Suv39h2 were generated according to standard techniques. The targeting strategies are shown in FIG. 9A–9C, as well as demonstrating the production of null alleles for both Suv39h1 and Suv39h2. Mutation of either gene results in viable and fertile mice as a consequence of functional redundancy between both loci. Therefore, Suv39h1 and Suv39h2 deficient strains were intercrossed to produce Suv39h double deficient mice. Double mutant mice are born in sub-Mendelian ratios, approximately 20% of the expected double mutants are observed and are infertile.

Additional experiments have shown that the murine Suv39h histone methyltransferases (HMTases) regulate histone H3 lysine 9 methylation at pericentric heterochromatin, and that this modification is essential for chromosome stability during mitosis and meiosis. Combined disruption of the Suv39h1 and Suv39h2 HMTases in the mouse germ line results in severely impaired viability and complete spermatogenic failure. Pericentric H3 lysine 9 methylation in somatic and early meiotic cells is lost in the absence of the Suv39h HMTases. Suv39h double null (dn) primary mouse embryonic fibroblasts display increased chromosomal instabilities—a phenotype that is further reflected by the development of B-cell lymphomas in Suv39h mutant mice. Second, in early meiotic prophase of Suv39h dn spermatocytes, chromosomes engage in non-homologous interactions through their centromeric regions and are delayed in synapsis. A significant fraction of meiosis I cells contains mis-segregated chromosome bivalents, and the highly heterochromatic Y chromosome fails to pair with the X chromosome. Together, the data obtained in Examples 11–17 establish a role for H3 lysine 9 methylation by Suv39h in regulating a heterochromatic competence' that protects chromosome function and genome stability during mitosis and meiosis.

The findings of the invention identify the Suv39h1 and Suv39h2 genes as essential regulators of higher order mammalian chromatin in chromosomal dynamics during mitosis and meiosis/male gametogenesis. Thus, in a first aspect the Suv39h1 and Suv39h2 genes are targets for interfering with aberrant gene expression and genomic instability through chromosome mis-segregation and thus provide the basis new cancer therapies. In addition, the experiments of the present invention identify Suv39h2 as a novel target in the treatment of male infertility and as a target for reversible male contraception.

In a first aspect, the present invention relates to the murine Suv39h2 polypeptide with the amino acid sequence as set forth in SEQ ID NO:2 or with the amino acid sequence encoded by a polynucleotide which hybridises under stringent conditions to a polynucleotide having a nucleotide sequence as set forth in SEQ ID NO:1.

By "stringent hybridisation conditions" as used herein is meant overnight incubation at 42° C. in a solution comprising: 50% formamide, 5×SSC (1×SSC=150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C., or equivalent conditions.

In a further aspect, the present invention relates to an isolated DNA molecule comprising a polynucleotide with the nucleotide sequence as set forth in SEQ ID NO:1 encoding murine Suv39h2 polypeptide or an isolated DNA molecule encoding murine Suv39h2, comprising a polynucleotide which hybridises under stringent conditions to a polynucleotide having a nucleotide sequence as set forth in SEQ ID NO:1.

In a preferred embodiment, the invention relates to the human SUV39H2 polypeptide encoded by a polynucleotide containing the sequence of the human EST SEQ ID NO:3 and/or SEQ ID NO:4 and/or SEQ ID NO:5 and/or SEQ ID NO:6, or by a polynucleotide which hybridizes under stringent conditions to the said polynucleotides.

In a further aspect, the present invention relates to an isolated DNA molecule encoding the human SUV39H2 protein, comprising a polynucleotide containing the sequence of the human EST SEQ ID NO:3 and/or SEQ ID NO:4 and/or SEQ ID NO:5 and/or SEQ ID NO:6, or an isolated DNA molecule.

The sequence information in the ESTs partially define human SUV39H2. The corresponding human SUV39H2 cDNA can be readily isolated using sequence information in SEQ ID NOs:3–6.The ESTs or part of the ESTs can be used as a probe to screen a suitable phage cDNA library, such as a testis library. Otherwise the sequence information in the above mentioned ESTs could be used to design a PCR (RT-PCR or RACE amplification) based strategy to isolate SUV39H2.

In the following, if not otherwise stated, the term "Suv39h2" refers to both the murine and the human SUV39H2.

Homologues of the subject Suv39h2 proteins also include versions of the polypeptide which are resistant to post-translation modification or which alter an enzymatic activity of the protein. The Suv39h2 polypeptide can comprise a full length protein, such as represented in SEQ ID NO:2, or it can comprise a fragment or variant thereof.

Beside DNA molecules, the present invention relates to nucleic acid molecules in the form of RNA, such as mRNA. The DNA molecules include cDNA and genomic DNA obtained by cloning or produced synthetically. The DNA may be double-stranded or single-stranded. Single-stranded DNA or RNA may be the coding strand, also known as the sense (or plus) strand, or it may be the non-coding strand, also referred to as the antisense (or minus) strand.

By "isolated" nucleic acid molecule(s) is intended a nucleic acid molecule, DNA or RNA, which has been removed from its native environment. Recombinant DNA molecules contained in a vector are considered isolated for the purposes of the present invention. Further examples of isolated DNA molecules include recombinant DNA molecules maintained in heterologous host cells, and those DNA molecules purified (partially or substantially) from a solution whether produced by recombinant DNA or synthetic chemistry techniques. Isolated RNA molecules include in vivo or in vitro RNA transcripts of the DNA molecules of the present invention. However, it is intended that "isolated" as used herein does not include the Suv39h2 cDNA present in a cDNA library or in a preparation of purified or isolated genomic DNA containing the Suv39h2 gene or a portion thereof in admixture with one or more other cDNA molecules or DNA fragments.

The nucleic acid molecules of the present invention further include genetic constructs comprising one or more Suv39h2 DNA sequences operably linked to regulatory DNA sequences (which may be heterologous regulatory sequences), such as promoters or enhancers as described below, wherein upon expression of these DNA sequences in host cells, preferably in bacterial, fungal (including yeast), plant or animal (including insect or mammalian) cells, one or more Suv39h2 polypeptides are produced. In such constructs, the regulatory sequences may be operably linked to a Suv39h2 polynucleotide encoding mature Suv39h2 polypeptide or any of its variants, precursors, fragments or derivatives described herein, which may include one or more polynucleotides having a nucleic acid sequence that is complementary to substantially all or a portion of a nucleic acid molecule having a nucleic acid sequence as shown in SEQ ID NO:1, 3, 5 and 6. As used herein, the terms "a portion" or "a fragment" of a nucleic acid molecule or a polypeptide means a segment of a polynucleotide or a polypeptide comprising at least 15, and more preferably at least 20, contiguous nucleotides or amino acids of a reference polynucleotide or polypeptide (for example, the polynucleotide and polypeptide shown in SEQ ID NOs: 1, 2 or 3 and 4, respectively, unless otherwise specifically defined below.)

Besides the DNA molecules having a nucleotide sequence corresponding to that depicted SEQ ID NO:1, or containing a sequence of SEQ ID NO: 3 and/or 4 and/or 5 and/or 6; the invention also relates to DNA molecules which comprise a sequence substantially different from those described above but which, due to the degeneracy of the genetic code, still encode the Suv39h2 mouse or human polypeptides. Since the genetic code is well known in the art, it is routine for one of ordinary skill in the art to produce the degenerate variants described above without undue experimentation.

In addition, the invention relates to Suv39h2 polypeptides which have deviations from the sequence shown in SEQ ID NO:2 or from a polypeptide encoded by a polynucleotide containing a sequence of SEQ ID NO: 3 and/or 4 and/or 5 and/or 6, caused by the conservative exchange of amino acids, if they are Suv39h2 derivatives or fragments or peptides with the properties which are desirable for their use in therapy or in screening assays. The invention also relates to isolated DNA molecules encoding such derivatitives or fragments with a polynucleotide sequence varying in their sequence from SEQ ID NO:1, or isolated DNA molecules varying in their sequence from a polynucleotide containing a sequence of SEQ ID NO: 3 and/or 4 and/or 5 and/or 6.

Nucleic acid molecules of the present invention which encode a Suv39h2 polypeptide or a derivative or fragment thereof may include, but are not limited to, those encoding the amino acid sequence of the polypeptide by itself, together with additional, non-coding sequences, including for example introns and non-coding 5' and 3' sequences, such as the transcribed, untranslated regions (UTRs) or other 5' flanking sequences that may play a role in transcription (e.g., via providing ribosome- or transcription factor-binding sites), mRNA processing (e.g. splicing and polyadenylation signals) and stability of mRNA; the coding sequence for the Suv39h2 polypeptide operably linked to a regulatory DNA sequence, particularly a heterologous regulatory DNA sequence such as a promoter or enhancer; and the coding sequence for the Suv39h2 polypeptide linked to one or more coding sequences which code for amino acids that provide additional functionalities. Thus, the sequence encoding the polypeptide may be fused to a marker sequence, such as a sequence encoding a peptide which facilitates purification of the fused polypeptide. In certain embodiments of this aspect of the invention, the marker amino acid sequence may be a hexa-histidine peptide, such as the tag provided in a pQE vector (Qiagen, Inc.), among others, many of which are commercially available. As described for instance in Gentz et al., 1989. The "HA" tag is another peptide useful for purification which corresponds to an epitope derived from the influenza hemagglutinin protein, which has been described by Wilson et al., 1984. Yet another useful marker peptide for facilitation of purification of Suv39h2 is glutathione S-transferase (GST) encoded by the pGEX fusion vector (see, e.g., Winnacker, From Genes to Clones, New York: VCH Publishers, pp. 451–481 (1987)). As discussed below, other such fusion proteins include the Suv39h2 fused to immunoglobulin Fc at the N- or C-terminus.

A still further aspect of the present invention relates to antibodies and antibody preparations specifically reactive with an epitope of the Suv39h2 polypeptide.

Polyclonal antibodies are conventionally obtained by immunising animals, particularly rabbits, by injecting the antigen Suv39h2 or fragments thereof and subsequently purifying the immunoglobulin.

Monoclonal anti-Suv39h2 antibodies may be obtained by standard procedures following the principle described by Köhler and Milstein, 1975, by immunising animals, particularly mice, then immortalizing antibody-producing cells from the immunized animals, e.g. by fusion with myeloma cells, and screening the supernatant of the hybridomas obtained by immunological standard assays for monoclonal anti-Suv39h2 antibodies. For therapeutic or diagnostic use in humans, these animal antibodies may optionally be chimerised in the conventional way (Neuberger et al., 1984, Boulianne et al., 1984, or humanised (Riechmann et al., 1988, Graziano et al., 1995).

Suv39h2 specific antibodies can be used to understand higher order chromatin mediated chromosome dynamics and for screening human conditions for Suv39h2 mediated pathologies.

The invention also features transgenic non-human animals, e.g., mice, rats, rabbits, chickens, frogs or pigs, having a transgene, e.g., animals which include (and preferably express) a heterologous form of an Suv39h2 gene described herein, or which mis-express an endogenous Suv39h2 gene, e.g. an animal in which expression of one or more of the Suv39h genes are disrupted. Such animals can serve as a model for studying cellular and tissue disorders comprising mutated or mis-expressed Suv39h2 alleles or for drug screening.

Another aspect of the present invention provides a method of determining if a subject, e.g., a human patient, is at risk for a disorder characterized by unwanted cell proliferation or aberrant control of differentiation. The method includes detecting, in a tissue of the subject, the presence or absence of a genetic lesion characterized by a mutation or a mis-expression of the Suv39h2 gene. In preferred embodiments, detecting the genetic lesion includes asserting the existence of at least one of: a deletion of one or more nucleotides from a Suv39h gene; an addition of one or more nucleotides to the gene, a substitution of one or more nucleotides of the gene, a cross chromosomal rearrangement of the gene; an alteration in the level of a messenger RNA transcript of a gene; the presence of a non-wild type splicing pattern of a messenger RNA transcript of the gene; or a non-wild type level of the protein.

The expression and immunolocalisation studies conducted in the present invention identify Suv39h2 as a novel component of meiotic higher order chromatin and the XY body. It has also been shown that the Suv39h homologues Suv39h1 and suv39h2 possess histone methyltransferase (HMTse) activity and that Suv39h function, supplied by Suv39h2, presumably in cooperation with Suv39h1, is an absolute requirement for male gametogenesis. The experiments of the present invention identify the Suv39h homologues Suv39h2 and, optionally, Suv39h1, as targets for novel strategies for reversible inhibition of male gametogenesis. Due to their identification as K9 specific histone H3 MTases and as a requirement for male gametogenesis, Suv39h homologues are also useful in a method for identifying compounds that have the ability of modulating higher order chromatin dependent chromosome stability during mitosis and meiosis, in particualar, of modulating mammalian male gametogenesis. This method is characterized in that one or more Suv39h homologues are incubated, in the presence of the substrate(s) for the HMTase activity and in the presence of a methyl donor, with test compounds and that the modulating effect of the test compounds on the HMTase activity of the Suv39h homologue(s) is determined.

In a preferred embodiment, Suv39h2 is employed in a primary screen, most preferably in its recombinant form. In a next step, the compound identified in the primary screen to be a modulator, e.g. an inhibitor, of Suv39h2, is assayed in a secondary screen for its ability to modulating, e.g. inhibiting, a further Suv39h homologue that is required for male gametogenesis, in particular Suv39h1. This secondary screen is identical to the one described above for Suv39h2.

Suv39h homologues can be produced recombinantly according to standard methods by expression in suitable hosts, e.g. bacteria, yeast, insect or eucaryotic cells and purified, e.g. on glutathione-agarose columns if it has been tagged with GST.

For testing compounds for their effect on Suv39h activity, the assay comprises, as its essential features, incubating a histone H3 protein or histone H3 N-terminal fragment including K9, a methyl donor, e.g. methionine or S-adenosyl-L-methionine, with a preparation containing Suv39h2 and determining the HMTase of activity in the presence or absence of a test substance.

Useful substrates may be those equivalent to or mimicking the naturally occurring substrates, e.g. biochemically purified histone H3, recombinantly produced histone H3, or an histone H3 peptide that contains the K9 methylation site.

Preferably, the histone H3 fragment ARTKQTARKSTG-GKAPRKQL (SEQ ID NO:7) is employed.

Alternatively, a modified peptide may be used for which the MTase has increased affinity/activity. Such peptides can be designed by exchanging and/or adding and/or deleting amino acids and testing the substrate in serial experiments for MTase affinity/activity.

The methyl group of the methyl donor preferably carries a detectable label, e.g. a radioactive or a chromogenic label, which can be quantified upon transfer to the substrate.

Preferably, the methyl donor is radioactively labelled methionine or S-adenosyl-L-methionine.

Alternatively to using a labelled methyl donor, the substrate, upon methylation by the enzyme, is used to serve as an epitope which can be recognized by a specific antibody and hence be quantified by standard immunoassay techniques, e.g. ELISAs. Antibodies useful in this type of assay can be obtained by using the methylated substrate, preferably a small peptide, e.g. the peptide with the sequence shown in SEQ ID NO:7, as an antigen and obtaining polyclonal or monoclonal antibodies according to standard techniques. The generation and purification of a methyl-specific antibody against the histone H3 lysine 9 position is described in the Materials and Methods section. A suitable H3-K9 methyl antibody was also described by Nakayama et al., 2001.

In an alternative embodiment, the screening method of the invention utilizes the fact that the methylation of histone H3 at lysine 9 (H3-K9) creates a high-affinity binding site for HP1 proteins. In this embodiment, the substrate, upon methylation, is allowed to bind to HP1 and then incubated with a labelled anti-HP1 antibody. The difference in label intensity between the reaction in the absence or presence of the test compound is indicative for the compound's modulating effect on MTase activity.

HP1 is preferably used in recombinant form. Based on the information of the HP1 cDNA sequence (Jones et al., 2000[; Accession No. BC006821]), HP1 is produced recombinantly according to standard technology. The recombinant protein or fragments thereof are used to generate polyclonal or monoclonal antibodies that are employed in this assay format.

In a preferred embodiment, the method of the invention is performed on a high-throughput scale. For this embodiment, the major assay components, in particular Suv39h2, are employed in recombinant form.

For the high throughput format, the screening methods of the invention to identify MTase inhibitors, are carried out according to standard assay procedures. Such assays are based on the catalytic transfer, mediated by Suv39h2 or a Suv39h variant, of a methyl group from a donor to a substrate, e.g. a histone H3 peptide. To achieve this, the substrate, e.g. histone H3 or a variant or fragment thereof, is immobilised on a carrier, usually a microtiter plate, and incubated with recombinant Suv39h2 and a methyl donor.

The methyl group of the methyl donor carries a label, preferably a chromogenic or radioactive label.

Fluorescent or radioactive labels and the other reagents for carrying out the enzymatic reaction on a high-throughput scale are commercially available and can be employed according to the supplier's instructions (e.g. Molecular Probes, Wallac). Examples for suitable fluorescent labels are coumarin derivatives, e.g., 7-amino-4-methylcoumarin or 7-amino-4-trifluoromethylcoumarin. The radioactive label may be a $^{14}C$ or a $^3H$ atom. Upon transfer of the methyl group to the substrate by Suv39h, in the case of a chromogenic reagent, the methyl donor changes colour which can be quantified. In the case of using a radioactive methyl donor, the methyl group is transferred to the substrate and can be directly quantified.

The specific assay design depends on various parameters, e.g. on the size of the substrate used. In the the case of using a short peptide, the fluorescence quenching or the fluorescence resonance energy transfer methods are examples for suitable assay technologies, as described below.

The substrate may be tagged, e.g. with biotin, the reaction is then carried out in solution and then transferred to streptavidin coated microtiter plates, e.g. in the case of a radioactive methyl group, "flash" plates, the material of which contains the scintillant, or plates which are coated with scintillant. Thus the level of methylation of the substrate can be quantified in a suitable scintillation machine/reader. Alternatively, the assay can be carried out in the streptavidin coated "flash" plates with the biotinylated substrate already bound to the plates. This type of assay may also be conducted in the form of a so-called "homogenous assay" (an assay type which does not require intermediate transfer and washing steps) e.g. by using microbeads that are coated with scintillant and streptavidin, to which the biotinylated substrate is bound.

Similarly to biotin, other commonly used tags, e.g. Flag, Myc, HA, GST, that are suitable to immobilize the substrate to the plate that is coated with the tag-specific antibody, may be used in the above-described assays.

In a variant, this assay is conducted in the format ELISA type assay; in this case, a methyl-specific antibody is used to detect the amount of methylated substrate bound to the plate.

Alternatively, the plate is coated with an antibody against the methylated substrate to capture the methylated substrate; the substrate is also either tagged or chromogenically labeled and the amount of bound methylated tagged/labeled substrate can be quantified either by a tag-specific antibody or by measuring the level of chromogenic label. By way of example, the substrate is a linear or a branched peptide, e.g. [TARKST]$_4$-K$_2$-K-cys that is labeled with a chromogenic label, e.g. europium, and upon methylation by a Suv39h-like MTase becomes an epitope for a Lys9-methyl specific antibody (see materials and methods) immobilised on a carrier (e.g. microtiter plate). The non-captured substrate is washed away, the europium label is then cleaved and its fluorescence enhanced and the level of fluorescence is calculated by time resolved fluorescence. The level of fluorescence is directly related to the level of methylated substrate (FIG. 19A–19B).

An alternative embodiment is based on the principle that methylation of the peptide may alter its sensitivity to cleavage by a protease. Utilizing this principle, the fluorescence quenching (Resonance Energy Transfer "RET") assay may be employed to determine the amount of methylation of peptidic substrates. In a first step, a Suv39h peptidic substrate, which contains the methylation site and a recognition/cleavage site for a defined protease, that is sensitive to modification (in the particular case, methylation of the lysine) of the recognition/cleavage site, e.g. trypsin or LysC. The peptide carries a fluorescent donor near one end and an acceptor near the other end. In the uncleaved substrate, the fluorescence of the substrate is quenched by the persisting intramolecular RET between donor and acceptor. Upon cleavage of the (unmethylated) substrate by the protease, the cleavage products are released from RET quenching and a fluorescence signal is generated. Methylation of the substrate abolishes the ability of the protease to cleave the substrate. Thus, abolishment of the protease activity (which is proportional to methylation) is reflected by signal repression, in case of total protease inhibtion, total signal repression to the basal level.

An assay of this type may be carried out as follows: the solution of the labeled substrate (e.g. the peptide labeled with 4-[[4 '-(dimethylamino)phenyl]azo]benzoic acid (DABCYL) at the one end and with 5-[(2'-aminoethyl)

amino]naphtalenesulfonic acid (EDANS) at the other end or labeled with benzyloxycarbonyl at the one end and with 4-aminomethylcoumarin at the other end) in assay buffer is transferred into each well of black 96-well microtiter plates. After addition of the test substances in the defined concentration, the MTase and the methyldonor are added to the wells. After incubation under reaction conditions and for a period of time sufficient for the methylation reaction, e.g. for 40 min at room temperature, the protease, e.g. trypsin, is added and allowed to react under suitable conditions, finally, the fluorescence is measured in a fluorometer at the excitation wavelength, e.g. at 340 nm, and at the emission wavelength, e.g. at 485 nm.

In the case of using the FRET assay, the following commercially availabe labeling pairs are suitable for the method of the invention: Europium (Eu) and Allophycocyanin (APC), Eu and Cy5, Eu and PE (Wallac, Turku, Finland). If a test substance is a modulator of the MTase activity, there will be, depending on the detection system and depending on whether the test substance has an inhibiting or an activating effect, a decrease or an increase in the detectable signal as compared to a control sample in the absence of a test substance. In the high-throughput format, compounds with a modulating effect Suv39h MTase activity can be identified by screening test substances from compound libraries according to known assay principles, e.g. in an automated system on microtiter plates.

The compounds identified in the above methods as Suv39h2 modulators have the ability to modulate higher order chromatin dependent chromosome stability during mitosis and meiosis.

Compounds inhibiting Suv39h2 HMTase activity result in decreased genome stability and can be used in therapy for targeting dividing cells, in particular highly proliferative tumour cells. They are preferably administered in combination with other genome destabilising agents, e.g. mitose inhibitors like tubulin binders (taxanes, e.g. taxol, Paclitaxel; or epithelones). SUV39H2 inhibitors may also be used jointly with or before the application of conventional tumour therapies, e.g. radiotherapy or chemotherapy, in particular DNA damaging agents, in order to pre-sensitize the tumour cells. By destabilizing the cell's genome, the SUV39H inhibitors make the cell more susceptible to the parallel/subsequent treatment.

The SUV39H2 inhibitors will preferably be used in a combination therapy and applied in consecutive and transient treatments. Since the development of B-cell lymphomas in Suv39h double null mice only occurs with a late onset (i.e. after 9 months of age), transient treatments with SUV39H inhibitors should not induce an immediate increase in tumor risk but rather weaken overall genomic stabilities of highly proliferating cells.

Likewise, agents which enhance Suv39h2 HMTase activity can be used to stabilise the genome of inherently unstable cells, rendering them less prone to acquiring proliferation promoting mutations.

The efficacy of compounds identified as Suv39h2 modulators can be tested for in vivo efficacy in mammalian cells with Suv39h double null cells serving as a positive control. Compounds effective in cancer therapy should interfere with chromosome stability and segregation, which can be measured by karyotyping, e.g. by analysing the DNA content by FACS or standard cytological techniques. Substances whose potential for therapeutic use has been confirmed in such secondary screens can be further tested for their effect on tumour cells. To test the inhibition of tumour cell proliferation, primary human tumour cells are incubated with the compound identified in the screen and the inhibition of tumour cell proliferation is tested by conventional methods, e.g. bromo-desoxy-uridine or $^3$H thymidine incorporation. Compounds that exhibit an anti-proliferative effect in these assays may be further tested in tumour animal models and used for the therapy of tumours.

By modulating the histone H3 methyl transferase activity of Suv39h2 required for male gametogenesis, the compounds identified in the above methods also have the ability of modulating male gametogenesis. Thus, they may be used in the treatment of male infertility (using compounds that enhance SUV39H2 MTase activity) and for reversible male contraception (using compounds that inhibit SUV39H2 MTase activity).

The efficacy of compounds identified as Suv39h2 modulators can be tested for in vivo efficacy to modulate spermatogenesis in mammals. The compound can be administered to adult male mice and the fertility assayed.

Compounds intended for male fertility applications can also be tested in animal models described by Vigil et al., 1985, in animal models developed for experimental studies of human spermatogenesis, as described by Weinbauer et al., 2001, or in animal models that mimic human male reproductive defects, as described by Lamb and Niederberger (1994). Guidance for a valid application of animal data to the assessment of human reproductive disorders is given by Working, 1988.

Toxicity and therapeutic efficacy of the compounds identified as drug candidates by the method of the invention can be determined by standard pharmaceutical procedures, which include conducting cell culture and animal experiments to determine the $IC_{50}$, $LD_{50}$, the $ED_{50}$. The data obtained are used for determining the human dose range, which will also depend on the dosage form (tablets, capsules, aerosol sprays, ampules, etc.) and the administration route (oral, buccal, nasal, paterental, rectal or, in the case of temporary male contraceptive applications, local sustained release form applications, e.g. slow-releasing micropellets that are implanted into or adjacent to the gonads). A pharmaceutical composition containing the compound as the active ingredient can be formulated in conventional manner using one or more physiologically active carriers and excipients. Methods for making such formulations can be found in manuals, e.g. "Remington Pharmaceutical Sciences".

As Suv39h2 is required to maintain a stable karyotype, it can be considered as a tumour suppressor gene. If SUV39H mutations also prove to be a factor underlying cellular transformation events in humans, which is strongly indicated by the analysis of Suv39h double null mice in developing B-cell lymphomas, it can be expected that the re-introduction of a wild type Suv39h gene by gene therapy results in increased genomic stability delaying or inhibiting cancer progression.

In addition, the Suv39h loss of function studies demonstrate that Suv39h has an essential function in male gametogenesis. Loss of Suv39h function may underlie a subset of male sterility cases in humans. Re-introduction of Suv39h2 or Suv39h1 genes into developing gametes through gene therapy has the potential to rectify these defects.

For gene therapy, the Suv39h DNA molecule may be administered, preferably contained on a plasmid in recombinant form, directly or as part of a recombinant virus or bacterium. In principle, any method of gene therapy may be used for applying Suv39h recombinant DNA, both in vivo and ex vivo.

Examples of in vivo administration are the direct injection of "naked" DNA, either by intramuscular route or using a gene guns. Examples of recombinant organisms are vaccinia virus or adenovirus. Moreover, synthetic carriers for nucleic acids such as cationic lipids, microspheres, micropellets or liposomes may be used for in vivo administration of nucleic acid molecules coding for the Suv39h2 polypeptide.

BRIEF DESCRIPTION OF FIGURES

FIG. 1A–1C: The coding part (SEQ ID NO:1) and conceptional reading frame (SEQ ID NO:2) of the (SEQ ID NO:2) of the Suv39h2 cDNA. Markings are as follows: asterisks, in-frame stop codons; arrowheads, exon/intron boundaries of exons 1-3; dashed box, conserved chromo domain; gray underlaying, conserved SET domain; darker grey bars, conserved C-terminal tail; grey circle highlights, basic amino acids in the N-terminal extension; circles, cysteine residues that are also conserved in Suv39h1; underlining, putative nuclear localization signals.

FIG. 8A–8B: The mammalian Su(var)3-9 harbours an intrinsic HMTase activity.

FIG. 9A–9C: Targeting Suv39h1 and Suv39h2 in the mouse germline.

FIG. 10A–10B: Suv39h function is required for male gametogenesis.

FIG. 11A–11D: Generation and genotyping of Suv39h1- and Suv39h2-deficient mice.

FIG. 12A–12D: Chromosomal instabilities in Suv39h dn PMEFs.

FIG. 13A–13C: Development of B-cell lymphomas in Suv39h mutant mice.

FIG. 16A–16K: Illegitimate associations and delayed synapsis of Suv39h dn meiotic chromosomes.

FIG. 17A–17F: Aberrant function of the Y chromosome during meiosis of Suv39h dn spermatocytes.

FIG. 18A–18B: Model for a 'heterochromatic competence' in protecting chromosome stability.

DETAILED DESCRIPTION OF THE INVENTION

Materials and Methods

Molecular Cloning of Murine Suv39h2

Figure 2:
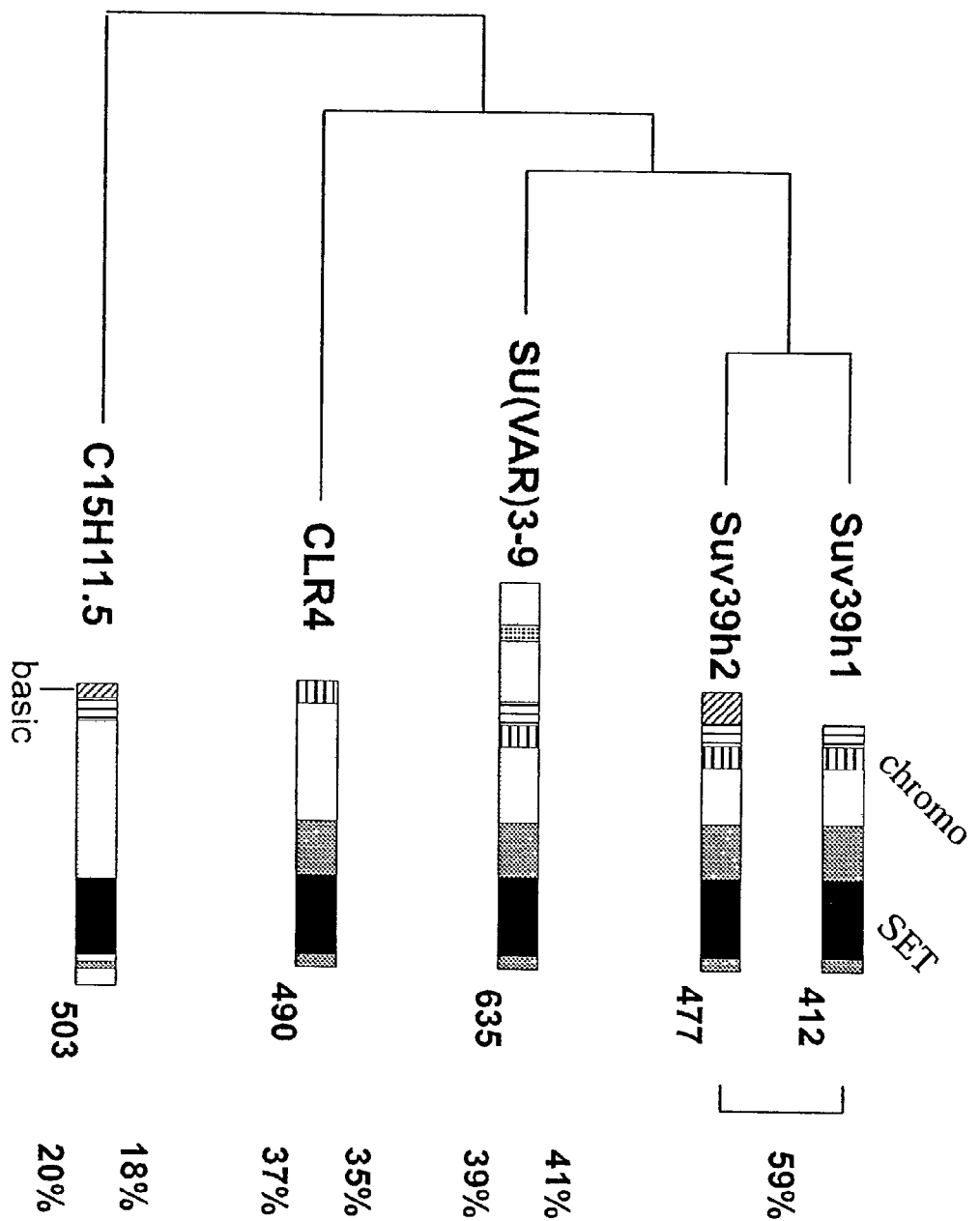
FIG. 2: Conserved domains of S.pombe, C.elegans, Drosophila and murine SU(VAR)3-9 related proteins.

A 210 bp EST DNA probe (encoding amino acids 219–289 of Suv39h2, see FIG. 1) was PCR-amplified from murine B-cell specific (J558L and S194) cDNA libraries using the Suv39h2-EST primers 5' GGGGAT-GATATTTGTTG-AAAACAC (SEQ ID NO:8) and 5' GGT-TGGATTTTAATTTGTTGCTTC (SEQ ID NO:9). This Suv39h2-EST DNA probe was screened against a day E11.5 mouse embryonic λgt11 cDNA library (Clontech) and a λ129/Sv genomic library (Stratagene), resulting in the isolation of six cDNA and three genomic clones. The longest cDNA (1 kb; λ4-Suv39h2) and genomic (14 kb) isolates were sequenced by primer walking on an automated sequencer (Applied Biosystems). Sequence analysis indicated that the cDNA encoded amino acids 132–477, and that the genomic sequence comprised exons 1–3, as predicted by GENE-finder. Missing 5' sequences of the Suv39h2 cDNA were extended by nested RACE amplification (Marathon cDNA amplification kit; Clontech) from the J558L and S194 cDNA libraries using the exon 3 specific primers 5' GCCCTCCAAGTCAACAGTG(SEQ ID NO:10) and 5' GTGTTGAGGTAATCTTGCCATC (SEQ ID NO:11). The RACE amplifications identified exon 2 (amino acids 83–131). Exon 1, including the starting ATG, was deduced from an EST which correctly spliced into exon 2 and whose sequence information was confirmed by comparison with genomic sequences.

RNA Isolation and Analysis

RNA isolation and analysis was done as described previously (Laible et al., 1997; Aagaard et al., 1999). Membranes were sequentially hybridized under stringent Church conditions (Sambrook et al., 1989) with a 1.6 kb EcoRI cDNA fragment comprising nearly full-length Suv39h1 or with a 980 bp cDNA PCR amplicon which codes for amino acid 143 to 477 of Suv3h2. To control for the quality of the RNA preparations, blots were rehybridised with a DNA probe that is specific for Gadph sequences (Dugaiczyk et al., 1983).

In-situ Analyses of Suv39h1 and Suv39h2 Expression with RNA Probes

To obtain Suv39h1 and Suv39h2-specific riboprobes, PCR-converted SalI/BamHI DNA fragments were subcloned into the polylinker of pGEM-3Zf (Promega) which allows in vitro transcription by SP6 and T7 RNA polymerases. Similar to an internal 395 bp DNA fragment encoding amino acids 113–237 of Suv39h1 (Aagaard et al., 1999), a 325 bp internal DNA fragment encoding amino acids 186–290 of Suv39h2 was used. Within this region, Suv39h1 and Suv39h2 nucleotide sequences are only approximately 53% identical and do not cross-hybridise. In-situ RNA probes were internally labelled with DIG-UTP (Boehringer Mannheim) by transcription with SP6 (antisense probe of EcoRI linearised plasmid) or T7 RNA polymerase (sense probe of BamHI linearised plasmid).

In-situ hybridizations of whole-mount embryos or of 5 μm sections of paraffin-embedded testis were performed at 65–70° C. O/N, washed under high stringency and processed for detection after incubation with anti-DIG alkaline phosphatase-conjugated antibodies and BM purple as the chromogenic substrate (Boehringer Mannheim).

Nuclear Extracts and Protein Blot Analysis

Isolation of nuclei from mouse testis was performed according to described protocols (Bunick et al., 1990; Motzkus et al., 1999). Approximately 30 μg of nuclear extracts from testis, the HeLa cell clones or from PMEFs were analyzed on protein blots with anti-myc, anti-M31 (HP1β) (Wreggett et al., 1994), anti-Suv39h1 and anti-Suv39h2 antibodies as recently reported (Aagaard et al., 1999).

Generation and Purification of Rabbit Polyclonal Anti-Suv39h2-Specific Antibodies Suv39h2 coding sequences comprising amino acids 157–477 were converted into a BamHI-EcoRI DNA fragment by PCR amplification and combined in-frame with N-terminal glutathione-S-transferase (GST) in the bacterial expression vector pGEX-2T (Pharmacia). Purification of recombinant protein and immunisation of rabbits with the GST-Suv39h2 antigen was done as described (Aagaard et al., 1999). An IgG fraction was prepared from the crude serum of rabbit #2218, batch-preabsorbed against GST-Suv39h1 glutathione-Sepharose beads (Aagaard et al., 1999), and anti-Suv39h2 antibodies were affinity-purified over a glutathione-Sepharose (Pharmacia) column that had been loaded with GST-Suv39h2. Following elution with 100 mM glycine pH 2.5, antibodies were neutralised with 1/10 vol. of 2 M Hepes pH 7.9. These affinity-purified anti-Suv39h2 antibodies (concentration~0.5 mg/ml) were used at 1:250 or 1:500 dilutions for protein blot analysis or at 1:10 to 1:20 dilutions for indirect immunofluorescence.

Immunofluorescence Analysis of Testis Suspension Cells

Testes were surgically removed from 3–6 months old C57B16/129 mice and minced with scalpel blades in cold MEM medium (Gibco) containing protease inhibitors (Roche Biochemicals). Structurally preserved suspension cells were prepared by cross-linking fixation as described (Pandita et al., 1999). Testis suspension cells were mixed with equal volumes of PBS-buffered (pH 7.2) 3.7% formaldehyde, 0.1 M sucrose, placed on silanised glass slides and allowed to dry down until they were coated by a thin layer of sucrose.

For indirect immunofluorescence (IF) of Suv39h epitopes, sucrose-embedded cells were briefly washed with PBS, extracted for 30 min. with 0.2% Triton X-100, PBS and incubated O/N at 4° C. with rabbit polyclonal anti-Suv39h1 (1:20; (Aagaard et al., 1999)) or rabbit polyclonal anti-Suv39h2 (1:20) antibodies that had been diluted in PTBG (PBS, 0.1% Tween 20, 0.2% BSA, 0.1% gelatin). Following three 3 min. washes in PTBG, samples were either incubated for 45 min. at 37° C. with secondary, CY3-conjugated goat anti-rabbit antibodies (Vector Laboratories) or with secondary goat anti-rabbit biotinylated antibodies (1; 500; Dianova) that were visualized after a third incubation by Avidin-FITC (1:1,000; Sigma). After three final washes in PBS, 0.1% Tween 20, preparations were mounted in Antifade solution (Vector Laboratories) containing 4',6'-diamidino-2-phenylindole (0.5 mg/ml) (DAPI; Sigma). Specificity of the staining was confirmed by control IF analyses in the absence of primary antibodies. Staging of individual mouse spermatogenic cells was determined by the development of SCP3-positive axial cores and the specific distribution of heterochromatin (Scherthan et al., 1996).

For double-labelling experiments, samples were first incubated with anti-Suv39h2 (1:10) antibodies, followed by sandwich detection with anti-rabbit biotinylated antibodies and Avidin-CY3 or Avidin-FITC. After a brief fixation with 1% formaldehyde in PBS, SCP3 or H1t epitopes were then detected with rabbit polyclonal anti-SCP3 (1:1,000; (Lammers et al., 1994)) or rabbit polyclonal anti-H1t (1:1,000; (Moens, 1995)) antibodies and visualised by secondary sheep anti-rabbit FITC-conjugated or sheep anti-rabbit CY3-conjugated (both Dianova) antibodies. Similarly, after triple-labelling for Suv39h2 with biotin and Avidin-CY3, samples were incubated with mouse monoclonal anti-Xmr (1:1,000; (Calenda et al., 1994)) antibodies that were detected with secondary goat anti-mouse FITC-conjugated antibodies (Dianova).

Processed samples were evaluated using a Zeiss Axiophot epifluorescence microscope equipped with 63× and 100× plan-neofluoar lenses and with single and double band pass filters for excitation of red, green and blue fluorescence (Chroma Technologies, Battleborough, Vt.). Digital black-and-white images were recorded with a cooled CCD camera (Hamamatsu), merged to RGB-images by the ISIS fluorescence image analysis system (MetaSystems) and processed in Adobe Photoshop 3.0.

Generation and Purification of GST-Fusion Proteins

The GST-Suv1(82–412) product expressed from the pGEX-2T vector (Pharmacia) as a glutathione-S-transferase (GST) fusion protein has been described (Aagaard et al., 1999). Additional GST constructs were generated by transferring BamHI-EcoRI PCR amplicons into pGEX-2T, encoding in-frame fusions for SUV39H1(82–412), Suv39h2 (157–477), CLR4(127–490) (Ivanova et al., 1998), EZH2 (382–747) (Laible et al., 1997) and HRX(3643-3969) (Tkachuk et al., 1992). All constructs were confirmed by sequencing.

Recombinant proteins were expressed in 11 cultures of $E.coli$ strain BL21 and solubilized in 10 ml RIPA buffer [(20 mM Tris pH 7.5, 500 mM NaCl, 5 mM EDTA, 1% NP-40, 0.5% sodium deoxycholate) containing a full set of protease inhibitors (Boehringer Mannheim) and lysozyme (5 mg/ml; Sigma)] by freeze-thawing in liquid $N_2$, followed by sonication. Soluble proteins were cleared by centrifugation, purified with 800 μl glutathione Sepharose beads (Pharmacia) and washed twice in RIPA buffer. Protein concentration was determined by Coomassie staining of SDS-PAGE gels. Matrix-bound fusion proteins were used immediately for in vitro HMTase assays or stored at 4° C.

In vitro Histone Methyltransferase (HMTase) Assay

In vitro HMTase reactions were modified based on described protocols (Strahl et al., 1999) and carried out in a volume of 50 μl of methylase activity buffer (MAB: 50 mM Tris pH 8.5, 20 mM KCl, 10 mM $MgCl_2$, 10 mM β-ME, 250 mM sucrose), containing 10 μg of free histones (mixture of H1, H3, H2B, H2A and H4; Boehringer Mannheim) as substrates and 300 nCi S-adenosyl-[methyl-$^{14}$C]-L-methionine (25 mCi/ml) (Amersham) as methyl donor. 10 μg of matrix-bound GST-fusion proteins were routinely used to assay for HMTase activity. After incubation for 60 min. at 37° C., reactions were stopped by boiling in SDS loading buffer, and proteins were separated by 15% or 18% SDS-PAGE and visualised by Coomassie staining and fluorography.

Generation of Suv39h1 and Suv39h2 Deficient Mice by Gene Targeting

Suv39h1 maps to the X-chromosome. The cloned partial Suv39h1 genomic locus was used to generate a targeting construct. A 1.2 kb Pfu PCR amplicon, generated with the primers gM3–9(SII) and gM3–9(RI), was used as a short arm of homology and cloned in frame with the nls-lacZ gene of the pGNA-T vector. This places the first 3 amino acids of exon 2 in frame with the nls-lacZ gene generating a fusion protein of the first 8 amino acids of Suv39h1 and lacZ from the targeted locus. A 5.4 kb SacI (filled in) fragment from Suv39h1 genomic subclone gSuv39h1 #18 was used as a long arm of homology.

Suv39h2 is autosomal and maps to chromosome 2. The cloned partial Suv39h2 genomic locus was used to generate a targeting construct. A 1.4 kb Pfu PCR amplicon, generated with the primers Suv2SII and Suv2RI, was used as a short arm of homology and cloned in frame with the nls-lacZ gene of the pGNA-T vector. This places the first 113 amino acids of exon 2 in frame with the nls-lacZ gene generating a fusion protein of the first 113 amino acids of Suv39h2 and lacZ from the targeted locus. A 4.9 kb MluI/ApaI (filled in) fragment from Suv39h2 genomic subclone gSuv39h2 #28 was used as long arm of homology to inactivate the locus.

These constructs were linearised with NotI, electroporated into R1 ES cells (Suv39h1) and E14.1 ES cells (Suv39h2), ES cells were put under G418 selection and G418 resistant colonies screened for homologous recombination by PCR and Southern blot analysis. Targeted feeder dependent ES cell clones were injected into blastocysts of C57BL/6 mice and reimplanted into pseudopregnant females to produce chimeric offspring. Germ-line transmission was obtained after a backcross between chimeric males and C57BL/6 females. Heterozygous mice were interbred to obtain Suv39h1and Suv39h2 deficient mice. Suv39h1 and Suv39h2 deficient mice were then interbred to generate Suv39h double deficient mice.

Targeting of the Suv39h1 and Suv39h2 Gene Loci in Embryonic Stem Cells

Partial genomic clones of the Suv39h1 locus (X chromosome) and of the Suv39h2 locus (chromosome 2) (O'Carroll et al., 2000) were used to generate short and long arms of homology, in a strategy to produce in-frame fusion proteins of the first 40 amino acids of Suv39h1 or of the first 113 amino acids of Suv39h2 with β-galactosidase (LacZ) modified with a nuclear localization signal (nls). For targeting, a 1.2 kb Pfu PCR amplicon and a 5.4 kb SacI DNA fragment were derived from the genomic subclone gSuv39h1 #18, and a 1.3 kb Pfu PCR amplicon and a 5.0 kb MluI/ApaI DNA fragment were prepared from the genomic subclone gSuv39h2 #28 (see FIG. 11A). The pGNA-derived targeting cassettes contained an RSV-neomycin (neo) gene for positive selection and two polyadenylation sites. The diphtheria toxin A (DTA) gene under the control of the MCI promoter was used to select against random integration and was inserted 3' of the long arms of homoloy. After linearisation with NotI, Suv39h1 and Suv39h2 targeting constructs were electroporated into feeder-dependent R1 and E14.1 (129/Sv) embryonic stem (ES) cells.

After selection, G418-resistant ES cell colonies were screened for homologous recombination by nested PCR using primers external to the short arms of Suv39h1 (PCR1: 5'-ATGGGGGCAGGGTTTTCGGGTAGAC, SEQ ID NO:12; PCR2: 5'-AAATGGTATTTGCAGGCCAC-TTCTTG, SEQ ID NO:13) or of Suv39h2 (PCR1: 5'-GAAAAGGTTGTTCTCCAGCTC, SEQ ID NO:14; PCR2: 5'-GGATGGGATGGTGG-AATGGTTTTTAT, SEQ ID NO:15) and primers within the lacZ gene (lacZ-PCR1: 5'-AACCCGTCGGATTCTCCGTGGGAAC, SEQ ID NO:16; lacZ-PCR2: 5'-CTCAGGAA-GATCGCACTC-CAGCC, SEQ ID NO:17).

Successful targeting was confirmed by Southern blot analysis of PvuII-digested ES cell DNA with a ≈500 bp external Suv39h1 intron probe, generated with the primers g24r (5'-GACTGC-CTAGTCTGGCACTGAACT, SEQ ID NO:18) and g13 (5'-GATCACTGCGTACATATAC-ACT-GAT, SEQ ID NO:19), or of HindIII-digested ES cell DNA with a ≈500 bp external Suv39h2 exon/intron probe, generated with the primers P1f (5'-TAGACTT-CTACTACAT-TAACG, SEQ ID NO:20) and P1r (5'-GATGTCAGTGGC-TATGAATG, SEQ ID NO:21). These DNA probes detect a 4.5 kb fragment from the wildtype Suv39h1 allele and a 4.0 kb fragment from the targeted allele, or 11 kb and 6.1 kb fragments from the Suv39h2 wildtype and targeted alleles (see FIG. 11B).

Generation and Genotyping of Suv39h1- and Suv39h2-Deficient Mice

Several independently targeted ES cell clones gave rise to chimaeric mice which passed the mutations through the germline. Suv39h1−/− and Suv39h2−/− mice were intercrossed to produce compound Suv39h mutant mice (e.g. Suv39h1−/−, Suv39h2+/−; null1/het2), which were then mated to generate Suv39h double null (dn) mice. All mice described in this study were maintained on a mixed genetic background of 129/Sv and C57Bl/6J origin.

Genotyping of mutant mice was done by Southern blot analysis as described above. Protein blot analysis of nuclear extracts from mouse testes with α-Suv39h1 and α-Suv39h2 antibodies was performed as described previously (O'Carroll et al., 2000).

Generation and Analysis of Suv39h Double Null Primary Mouse Embryonic Fibroblasts (PMEFs)

PMEFs were derived from day E12.5 Suv39h double null embryos obtained after intercrossing $Suv39h1^{-/-}/Suv39h2^{+/-}$ compound mutant mice. As controls, PMEFs were prepared from wild-type embryos of the same genetic background. For cell cycle profiles and growth curve analysis, passage 2 PMEFs were analyzed as described (Xu et al., 1999). Staining of PMEF interphase chromatin with α-phosH3 (Hendzel et al., 1997) antibodies was done in unpermeabilized cells as described (Melcher et al., 2000). For the biochemical analysis, total nuclear extracts were precalibrated by Ponceau staining, immuno-blotted with α-H3 (Upstate Biotechnology) and α-phosH3 (Hendzel et al., 1997) antibodies and visualised by peroxidase staining using Enhanced ChemiLuminescence (ECL) (Amersham).

Growth Curves and FACS Analyses of PMEFs

To analyze the proliferative potential of wild-type and mutant cells, PMEFs were seeded onto 10 cm² dishes. Over the next 30 passages, $3 \times 10^5$ cells were continually reseeded every third day onto a new 10 cm² dish (3T3 protocol), and their doubling rates determined. The DNA profiles of passage 3 and passage 8 PMEF cultures were obtained by FACS of ethanol-fixed and propidium-iodide stained cells, using chicken erythrocyte nuclei (Becton Dickinson) as an internal standard.

Bone Marrow Culture and FACS Analysis of B-cell Lymphoma Cells

Bone marrow cells from wt and Suv39h dn mice were cultivated for two weeks in StemPro-34 SFM medium (Life Technologies) supplemented with IL-3 (10 ng/ml), IL-6 (5 ng/ml), SCF (100 ng/ml), FLT 3 ligand (20 ng/ml), GM-CSF (1 ng/ml) (all from R&D Systems), 10 μM dexamethasone (Sigma) and IGF-1 (40 ng/ml) (Sigma). Cultures were grown at densities of ≈ $3 \times 10^6$ cells per ml, and purified from differentiated and dead cells by Ficoll-Paque gradient centrifugation (Pharmacia).

Primary lymphoma cells were obtained from spleen and lymph nodes using a 70 μm Nylon Cell Strainer (Becton Dickinson), and cultivated in Iscove's modified Dulbecco's medium (IMDM) supplemented with 5% heat-inactivated fetal calf serum, 2 mM glutamine and 1% penicillin-streptomycin (all Gibco-BRL). Single cells suspensions were grown O/N in medium additionally containing 50 μgM β-mercaptoethanol and 5% conditioned supernatant from rIL-7 producing J558L cells.

The identity of the tumor cells was determined by FACS analyses using antibodies (all from Pharmingen) that detect specific cell surface markers. All tumor cells were double positive for the B-cell markers B220-low (RA3-6B2) and CD19 (1D3), but negative for the T-cell markers CD3 (145-2C11), CD4 (RM4-5), CD8 (53-6.7), or for the granulocyte/macrophage markers Gr-1 (RB6–8C5), Mac-1 (M1/70) and for a marker of the eythroid lineage, Ter-119. The majority of the B-cell lymphoma cells were also double positive for CD43 (S7) and IgM (R6–60.2), while some clonal cultures displayed reactivity towards CD5 (53–7.3). These FACS profiles characterize the Suv39h-mediated tumors as being similar to chronic lymphoid leukemia in humans (Foon and Gale, 1995).

Chromosome Spreads and Karyotype Analyses

PMEF and tumor cell karyotypes were analyzed on colchicine-arrested and Giemsa-stained metaphase chromosome spreads as described previously (Czvitkovich et al., 2001).

Metaphase spreads of spermatogonia and spermatocytes were prepared from isolated seminiferous tubule fragments which had been hypotonically swollen with 1% sodium citrate for 10 min. at RT and fixed O/N at 4° C. with Carnoy's solution (75% methanol, 25% acetic acid). After incubation of seminiferous fragments in 60% acetic acid for 2 min., a single cell suspension was generated by repeated pipetting, transferred onto a pre-heated (60° C.) glass slide, and cells were spread by mechanical shearing with a glass hockey stick.

Generation and Purification of α-MethH3-K9 Antibodies

To generate methyl-specific antibodies against the histone H3 lysine 9 position, a hexameric peptide was generated, -TARK(Me)$_2$ST-cys (SEQ ID NO:22), containing a di-methylated lysine (Bachem) and a terminal cysteine. To increase the antigenicity and immunogenicity, a 'branched' peptide that consists of four -TARK(Me)$_2$ST-(SEQ ID NO:23) 'fingers' which are linked at their C-termini via lysine residues was also synthesized. The sequence of this 'branched' peptide is [TARK(Me)$_2$ST]$_4$-K$_2$-K-cys (SEQ ID NO:24). Peptides were coupled to KLH and rabbit polyclonal antisera were raised, indicating that the 'branched' peptide was much more immunogenic than the linear peptide.

Crude antisera from two positive rabbits (#2233 and #2236) were batch-absorbed against a 'branched', but unmodified control peptide, followed by affinity purification against the di-methylated 'branched' antigen that had been crosslinked to a Poros™ column (Lachner et al., 2001). Bound antibodies were eluted with 100 mM glycine pH 2.5 and neutralised with 1/10 vol. of 2 M Hepes pH 7.9. The methyl-specificity of the antibodies was confirmed on slot-blots presenting unmodified or K9-dimethylated histone H3 peptides and on protein blots containing nuclear extracts from wt or Suv39h dn PMEFs. The affinity-purified α-methH3-K9 antibodies (concentration≈0.6 mg/ml) can be used at a 1:1,000 dilution for protein blot analysis or at 1:1,000 to 1:5,000 dilutions for indirect immunofluorescence.

Immunofluorescence of Interphase Chromatin and Metaphase Chromosomes

Passage 6 PMEFs were fixed with 2% p-FA for 10 min. on ice, washed, incubated with blocking solution (PBS, 2.5% BSA, 10% goat serum and 0.1% Tween20) for 30 min at RT and stained O/N at 4° C. with the α-methH3-K9 antibodies. After several washes with PBS containing 0.2% BSA and 0.1% Tween20, the primary antibodies were detected with Alexa Fluor488-conjugated goat α-rabbit antibodies (Molecular Probes). DNA was counterstained with 4',6'-diamidino-2-phenylindole (DAPI), and samples were embedded in Vectashield (Vector Laboratories).

For preparation of metaphase chromosomes, bone marrow cells or primary tumor cells were arrested by colchicine treatment (0.5 mg/ml) (Sigma) for 2.5 hrs., followed by hypotonic swelling in 0.6% KCl or RBS buffer (10 mM TrisHCl pH 7.4; 10 mM NaCl; 5 mM MgCl$_2$) for 15 min. at 37° C. and centrifugation for 8 min. at 2000 rpm in a Cytospin (Shandon). Spreaded cells were immediately fixed with icecold 2% p-FA in PBS for 15 min., washed twice and stained with the α-methH3-K9 antibodies as described above.

Testes Histology

Testes were dissected from adult mice, fixed in Bouins fluid (75% saturated picric acid, 5% glacial acetic acid, 9.3% formaldehyde) and stained with haematoxylin/eosine. Staging of the seminiferous tubules was performed according to Oakberg (1956) and Russell et al. (1990). FISH analyses with mouse major satellite DNA probes were done as recently described (Scherthan et al., 1996), and Tunel assays were performed using the DeadEnd apoptosis detection system (Promega). In addition, testis cryosections (O'Carroll et al., 2000) were also analyzed by immunohistochemistry with α-Scp, α-Hp1β, α-phosH3 and α-meth H3-K9 antibodies.

Immunofluorescence of Germ Cells and Meiotic Chromosome Spreads

Chromosome spreads of spermatogenic cells were prepared according to Peters et al. (1997a) with some minor modifications. A single germ cell suspension was obtained in DMEM medium by mechanical disruption of isolated seminiferous tubules. After serveral washes and hypotonic swelling in hypobuffer (30 mM TrisHCl pH 8.2, 50 mM sucrose, 17 mM sodium citrate) for 10 min. at RT, cells were resuspended in 100 mM sucrose, 15 mM TrisHCl pH 8.2 and spreaded on precleaned slides covered by a thin film of 1% p-FA containing 5 mM borate pH 9.2 and 0.15% TritonX-100. Slides were dried slowly in a humid chamber for ≈2 hrs and stored at −80° C. Classification of meiotic sub-stages was performed according to the changing morphology of autosomes and sex chromosomes as described (Peters et al., 1997b).

Double-labelling immunofluorescence of these germ cell preparations was performed by sequential incubation with rabbit polyclonal α-methH3-K9 antibodies and with goat α-rabbit Alexa568-conjugated secondary antibodies. After a brief fixation in 1% p-FA, samples were incubated with rabbit polyclonal α-Scp3 antibodies (Lammers et al., 1995) that were visualized with goat α-rabbit Alexa488-conjugated secondary antibodies. In addition, co-stainings were also done with α-Scp3 and α-Scp1 (Offenberg et al., 1991) (see FIGS. 16A–C),and α-Scp3 and α-HP1β (Wreggett et al., 1994), and α-Scp3 and α-phosH3 (Hendzel et al., 1997) antibodies.

EM Analysis

Preparation and silver staining of SC complexes from spreaded germ cells (see above) was performed according to Peters et al. (1997a), and samples were analyzed on a Jeol 1200 EKII transmission electron microscope.

EXAMPLE 1

The Coding Part and Conceptional Reading Frame of the Suv39h2 cDNA

To identify additional mammalian Su(var)3-9 homologues, sequence similarity searches (Bassett et al., 1995; Altschul et al., 1997) with the murine Suv39h1 or human SUV39H1 cDNAs (Aagaard et al., 1999) revealed the presence of related, yet distinct expressed sequence tags (ESTs) in DDBJ/EMBL/GenBank databases. In particular, the mouse ESTs fall into two categories that are either homologous to Suv39h1/SUV39H1 or indicative of a second mammalian Su(var)3-9 homologue. Using oligonucleotides specific for this second class of Suv39h-ESTs, an internal (lacking the conserved chromo and SET domain sequences) DNA probe was PCR-amplified from murine cDNAs and screened against a mouse embryonic day 11.5 cDNA library (see Materials and Methods). Out of six positive isolates, the longest insert was subcloned and sequenced, revealing a nearly full-length open reading frame which comprises the chromo and the C-terminal SET domain. RACE-amplifications with cDNA templates from the murine B-cell specific cell lines J558L and S194 extended the missing 5' end, however, did not detect a starting ATG. To obtain more sequence information, a partial Suv39h2 genomic clone of approximately 14 kb was isolated (see Materials and Methods). Comparison of the available genomic, cDNA and EST sequences for the Suv39h1-related gene allowed the definition of exon 1 (see Materials and Methods) that contains a consensus ATG preceded by in-frame stop codons and which can correctly splice into exon 2. In analogy to Suv39h1, this novel gene was designated Suv39h2 (for Su(var)3-9 homologue 2). The nucleotide sequence (~1.5 kb) and conceptional reading frame (477 amino acids) of the composite coding Suv39h2 cDNA is shown in FIG. 1.

FIG. 1A–1C shows the ~1.5 kb nucleotide sequence (SEQ ID NO:1 and conceptional reading frame of the coding part (SEQ ID NO:2) of the Suv39h2 cDNA. Exon1, including the starting ATG preceded by in-frame stop codons (asterisks), has been derived from genomic Suv39h2 sequences and from an EST that correctly spliced into exon 2. From the available genomic sequences, exons 1–3 could be identified, and their respective exon/intron boundaries are indicated by arrowheads at nucleotide positions 278, 424 and 1083. The 477 amino acids Suv39h2 protein contains several conserved sequence motifs, including a chromo domain (dashed box), the SET domain (grey underlaying) and a C-terminal tail (darker grey bars). Basic amino acids in the N-terminal extension are highlighted by grey circles. In addition, cysteine residues that are also conserved in Suv39h1 are circled. Putative nuclear localisation signals are underlined (FIG. 1C).

EXAMPLE 2

Conserved Domains of S.pombe, C.elegans, Drosophila and Murine SU(VAR)3-9 Related Proteins Over the length of the 477 amino acids protein (SEQ ID NO:2), Suv39h2 is 59% identical to Suv39h1 (412 amino acids; (Aagaard et al., 1999)). Suv39h2 contains a highly basic (20.7%) N-terminal extension of 82 amino acids that is not present in Suv39h1, although a very basic N-terminus is also found in the C15H11.5 ORF. In addition to its obvious resemblance with protamines, the Suv39h2 N-terminus shows moderate sequence identity (23.2%) with the C-terminal half of the linker histone H1 that is not restricted to basic residues. With the exception of this extended N-terminus, Suv39h2 maintains all other conserved domains outlined previously for Suv39h1 (Aagaard et al., 1999). For example, both proteins display highest identity in the 130 amino acid SET domain core (75.2%) and at the conspicuous C-terminal tail (69.6%) with its three conserved cysteine residues. Highly identical is also the 60 amino acids chromo domain (62.7%), the SET-associated cysteine-rich region (54.9%) and the 'SU(VAR)3-9 specific' N-terminus (45.0%). In agreement with Suv39h1, Suv39h2 is also significantly shorter as compared to the 635 amino acids fly protein. Alignment of all five representative SU(VAR)3-9 related proteins revealed that among these conserved sequence motifs only the characteristic chromo and SET domains and the C-terminal tail are shared by all family members. By contrast, the SET-associated cysteines are absent in the C. elegans C15H11.5 ORF and less than half of the SET-adjacent, cysteine-rich region appears conserved. The highest variation is observed at the N-termini, with SU(VAR)3-9 containing a 155 amino acid extension including a putative GTP binding site (Tschiersch et al., 1994), CLR4 lacking any sequences preceding the chromo domain, and with Suv39h2 and the C15H11.5 ORF encoding very basic, yet distinct N-terminal extensions.

FIG. 2 illustrates the phylogenetic relationships of murine Suv39h1 (412 amino acids), murine Suv39h2 (477 amino acids) (SEQ ID NO:2), Drosophila SU(VAR)3-9 (635 amino acids), S.pombe CLR4 (490 amino acids) and a C.elegans ORF C15H11.5 (503 amino acids). Over the entire length of the protein, Suv39h1 shares 59% identity with Suv39h2, 41% identity with SU(VAR)3-9, 35% identity with CLR4 and 18% identity with C15H11.5. Similarly, Suv39h2 shares 59% identity with Suv39h1, 39% identity with SU(VAR)3-9, 37% identity with CLR4 and 22% identity with C15H11.5. Highly conserved sequence motifs are indicated, and comprise the chromo (box filled with vertical lines) and SET (black) domains, and the SET-associated cysteine-rich clusters (grey) which are only in part present in C15H11.5. In addition, an N-terminal region (box filled with horizontal lines) shared by the murine and fly proteins (Aagaard et al., 1999), a putative GTP-binding domain (dot filled box) (Tschiersch et al., 1994) in SU(VAR)3-9 and the basic N-termini (box filled with diagonal lines) in Suv39h2 and C15H11.5 are also highlighted.

EXAMPLE 3

Expression of Suv39h1 and Suv39h2 During Mouse Development

Figure 3:
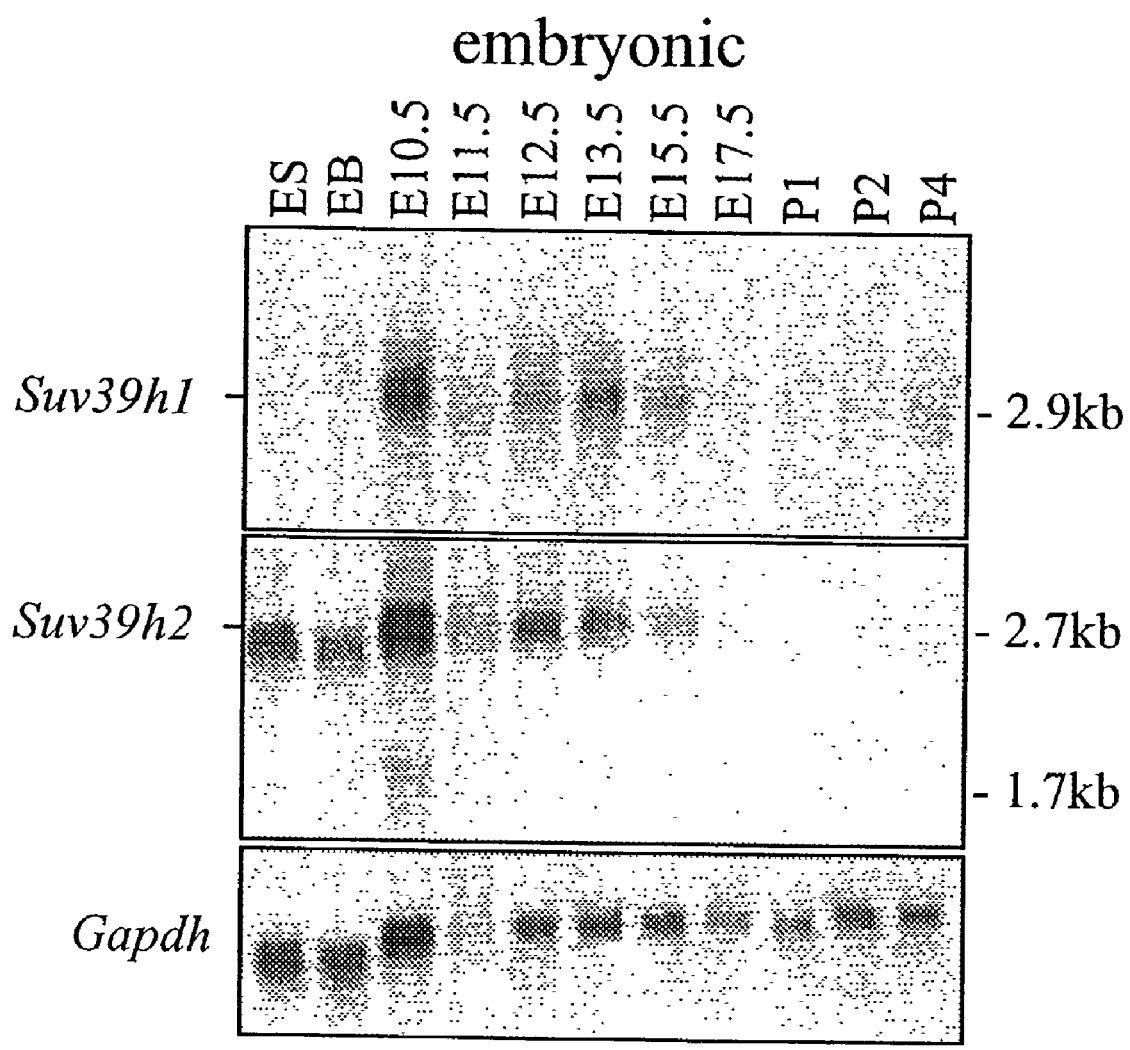
FIG. 3: Expression of Suv39h1 and Suv39h2 during mouse development.

Abundant Suv39h2-specific transcripts are present in ES-cells, in in vitro differentiated embryoid bodies (EB) and between day E10.5-day E15.5, with embryonic expression peaking around day E10.5. In contrast, Suv39h2 transcripts are substantially down-regulated at day E17.5 and are nearly absent during postnatal development. A very similar dynamic expression profile was also observed for Suv39h1, with the exception that the relative abundance of Suv39h1 transcripts in ES-cells and embryoid bodies is reduced as compared to Suv39h2 transcripts (FIG. 3, top panel). To investigate the spatial expression profiles of Suv39h2 and Suv39h1, whole-mount in-situ hybridisations with Suv39h2- and Suv39h1-specific riboprobes (see Materials and Methods) was performed on day E8.5 and day E9.5 mouse embryos. Whereas only residual staining is observed with a Suv39h2 control sense probe, the Suv39h2 antisense probe reveals a rather uniform expression throughout the entire embryos. Similarly, the Suv39h1 antisense probe detects a broad distribution of transcripts, consistent with the ubiquitous expression of Suv39h1 in previous in-situ hybridisations on sagittal sections of day E12.5 embryos (Aagaard et al., 1999). In addition to embryonic tissues, the mesenchyme-derived allantois is also prominently stained by the Suv39h1 antisense probe. Together with the RNA blot shown above, this comparative analysis indicates significant co-expression and potential overlapping functions during mouse development for Suv39h1 and Suv39h2.

FIG. 3 shows the RNA blot analysis to detect Suv39h1 and Suv39h2 transcripts in 15 µg of total RNA prepared from undifferentiated CCE embryonic stem cells (ES), embryoid bodies (EB) derived after retinoic acid-induced in vitro differentiation of CCE cells, and whole embryos at various stages of embryonic (E10.5-E17.5) and postnatal development (P1-P4). As a control for the quality of the RNA, the RNA blot was re-hybridized with a probe that is specific for Gapdh sequences.

EXAMPLE 4

Testis-specific Expression of Suv39h2

The abundance of Suv39h2 and Suv39h1 transcripts greatly differs in adult tissues. Whereas Suv39h1 displays broad expression in a panel of RNA preparations comprising 14 adult tissues, expression of Suv39h2 remains largely restricted to testes, with mRNAs being present as 2.7 kb and 1.7 kb transcripts. In addition to other tissues, Suv39h2 transcripts are also significantly down-regulated in ovaries. To analyse this testis-specific expression in more detail, in-situ hybridisations on sections of adult testes were performed. The Suv39h2 and Suv39h1 antisense probes revealed specific expression in the outermost cell layer of the seminiferous tubules, whereas the corresponding control sense probes proved negative. Suv39h2-specific transcripts appear at elevated levels as compared to Suv39h1. Higher magnification shows predominant staining of type B spermatogonia and pre-leptotene spermatocytes. Suv39h2-specific transcripts are also detected at reduced levels in several pachytene-stage cells and in mitotically inactive Sertoli cells. Together, these data indicate a prominent expression of Suv39h2 transcripts in male germ cells during the early stages of spermatogenesis and are suggestive of a function for Suv39h2 in male gametogenesis.

Figure 4:
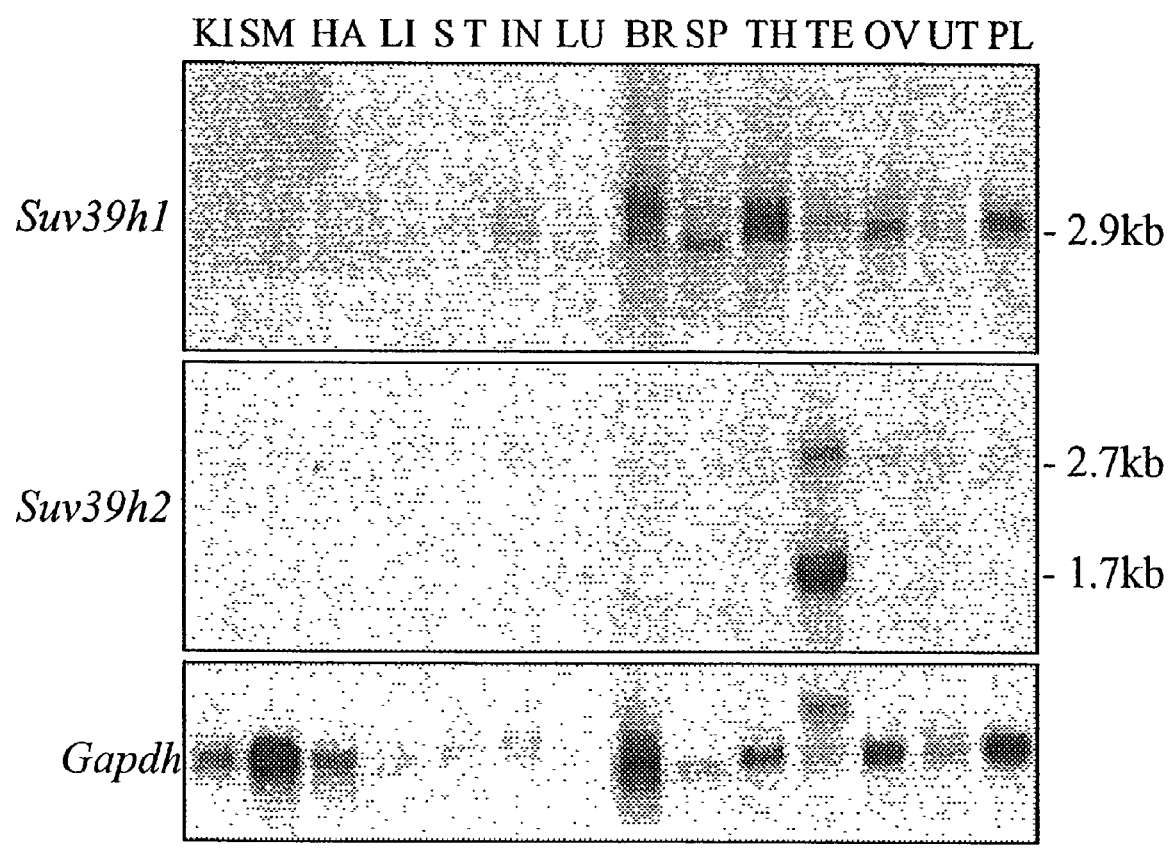
FIG. 4: Testis-specific expression of Suv39h2.

FIG. 4 shows the RNA blot analysis to detect Suv39h1 and Suv39h2 transcripts in 15 µg of total RNA prepared from adult 129/Sv tissues, including kidney (KI), skeletal muscle (SM), heart (HA), liver (LI), stomach (ST), intestine (IN), lung (LU), brain (BR), spleen (SP), thymus (TH), testis (TE), ovaries (OV), uterus (UT) and placenta (PL). As a loading control, the RNA blot was re-hybridized with a probe that is specific for Gapdh sequences.

EXAMPLE 5

Generation of Anti-sera Specific for Suv39h2

Figure 5:
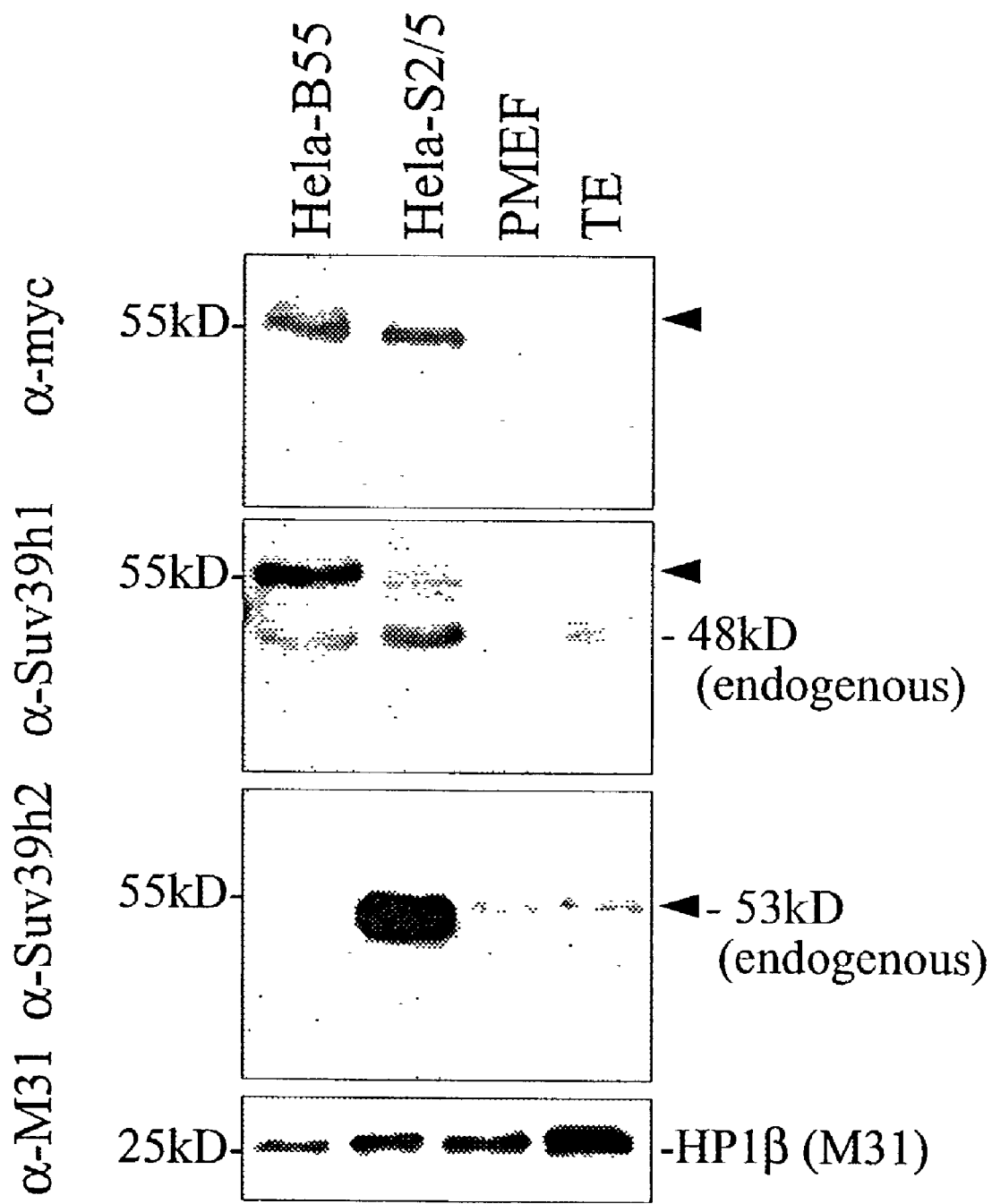
FIG. 5: Detection and size of the endogenous Suv39h2 protein.

To characterize Suv39h2 expression at a biochemical level, a polyclonal rabbit antiserum that was raised against a recombinant glutathione S-transferase (GST) fusion protein comprising amino acids 157–477 of murine Suv39h2 was generated. This serum was preabsorbed against the related GST-Suv39h1 antigen (Aagaard et al., 1999) and affinity-purified (see Materials and Methods). Western blot analysis of in-vitro translated Suv39h2 and human SUV39H1 (which is 95% identical to murine Suv39h1; (Aagaard et al., 1999)) indicated that the anti-Suv39h2 antiserum specifically recognized the Suv39h2 gene product but largely failed to detect the endogenous protein in a variety of mammalian cell lines. Therefore protein blots containing nuclear extracts from primary mouse embryonic fibroblasts (PMEFs) and from adult testis were probed with anti-Suv39h1 and anti-Suv39h2 antibodies. As a specificity and size control, nuclear extracts from HeLa cell lines that 'stably' overexpress $(myc)_3$-SUV39H1 (HeLa-B55; 40) or a corresponding $(myc)_3$-Suv39h2 construct which encodes amino acids 83–477 of the Suv39h2 cDNA (HeLa-S2/5) were included (see Materials and Methods). Immunoblotting with anti-Suv39h1 antibodies indicated the presence of ectopic $(myc)_3$-SUV39H1 (55 kDa) and of endogenous SUV39H1 (48 kDa) in HeLa-B55 nuclear extracts. However, endogenous Suv39h1 was undetectable in PMEFs and only low-abundant in testis (FIG. 5, middle panel). By contrast, the anti-Suv39h2 antibodies recognize an endogenous protein of approximately 53 kDa in both PMEFs and testis (FIG. 5, lower panel), which co-migrates with ectopic $(myc)_3$-Suv39h2(83–477) in HeLa-S2/5 nuclear extracts. It was concluded that Suv39h2 is more highly expressed in PMEFs and testis than Suv39h1, and that the size of the endogenous Suv39h2 protein is in good agreement with the gene product predicted from the coding sequence of the Suv39h2 cDNA (SEQ ID NO:1) (see FIG. 1A–1C).

In the experiment shown in FIG. 5, approximately 30 µg of nuclear extracts from HeLa-B55, HeLa-S2/5, primary mouse fibroblasts (PMEFs) and adult testis (TE) were immunoblotted with anti-myc, anti-Suv39h1, anti-Suv39h2 and anti-M31 (as a loading control) antibodies. HeLa-B55 overexpress $(myc)_3$-SUV39H1(3–412) and HeLa-S2/5 overexpress $(myc)_3$-Suv39h2(83–477). The size of these ectopic proteins is indicated by arrowheads. Endogenous Suv39h2 (53 kDa) co-migrates with $(myc)_3$-Suv39h2(83–477). The anti-Suv39h1 and anti-Suv39h2 antibodies are specific for their respective epitopes and do not cross-react.

EXAMPLE 6

Figure 6:
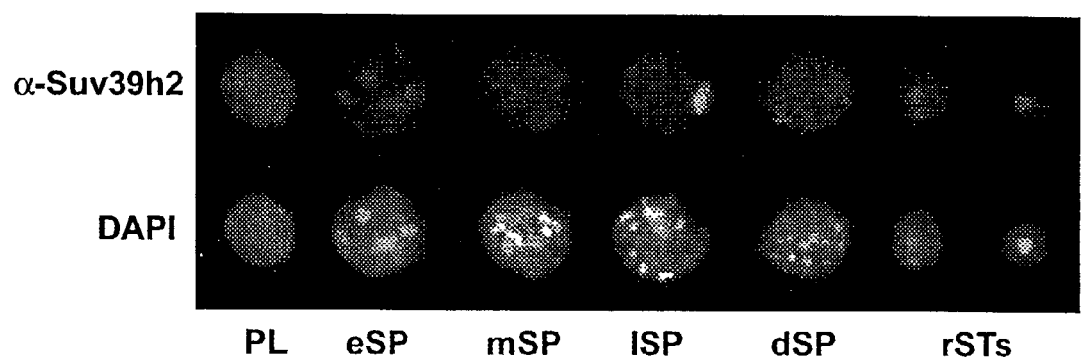
FIG. 6: Dynamic heterochromatin association of Suv39h2 during most stages of spermatogenesis.

Dynamic Heterochromatin Association of Suv39h2 during Most Stages of Spermatogenesis The subnuclear localization endogenous Suv39h2 protein in nuclei of testis swab preparations was analyzed (see Materials and Methods) by indirect immunofluorescence with the anti-Suv39h2 antibodies. Possible chromosomal associations in structurally preserved suspension cells that comprised early to late stages of spermatogenesis were examined. Endogenous Suv39h2 is found in a dispersed distribution in some pre-meiotic nuclei and as a granular stain in all pre-leptotene nuclei (FIG. 6, left nucleus). During the development of leptotene to diplotene spermatocytes, Suv39h2 staining is weakly but distinctly apparent at blocks of heterochromatin, as visualised by the bright DAPI counterstaining. Surprisingly, prominent Suv39h2 signals accumulate at the sex chromosomes present in the XY body during mid-pachytene (see below). After the meiotic divisions, Suv39h2 remains enriched at the condensing heterochromatic foci of haploid spermatids (FIG. 6, right nuclei), but is no longer detectable in mature sperm.

FIG. 6 shows the indirect immunofluorescence of testis suspension cells with anti-Suv39h2 antibodies. DNA was counterstained with DAPI (bottom panel). Staging of individual mouse spermatogenic cells was determined as described in Materials and Methods and comprised preleptotene spermatogonia (PL), early, middle and late spermatocytes (eSP, mSP, lSP), diplotene spermatocytes (dSP), and round spermatids (rST).

EXAMPLE 7

Suv39h2 Accumulates with Sex Chromosomes Present in the X-Y Body

Figure 7:
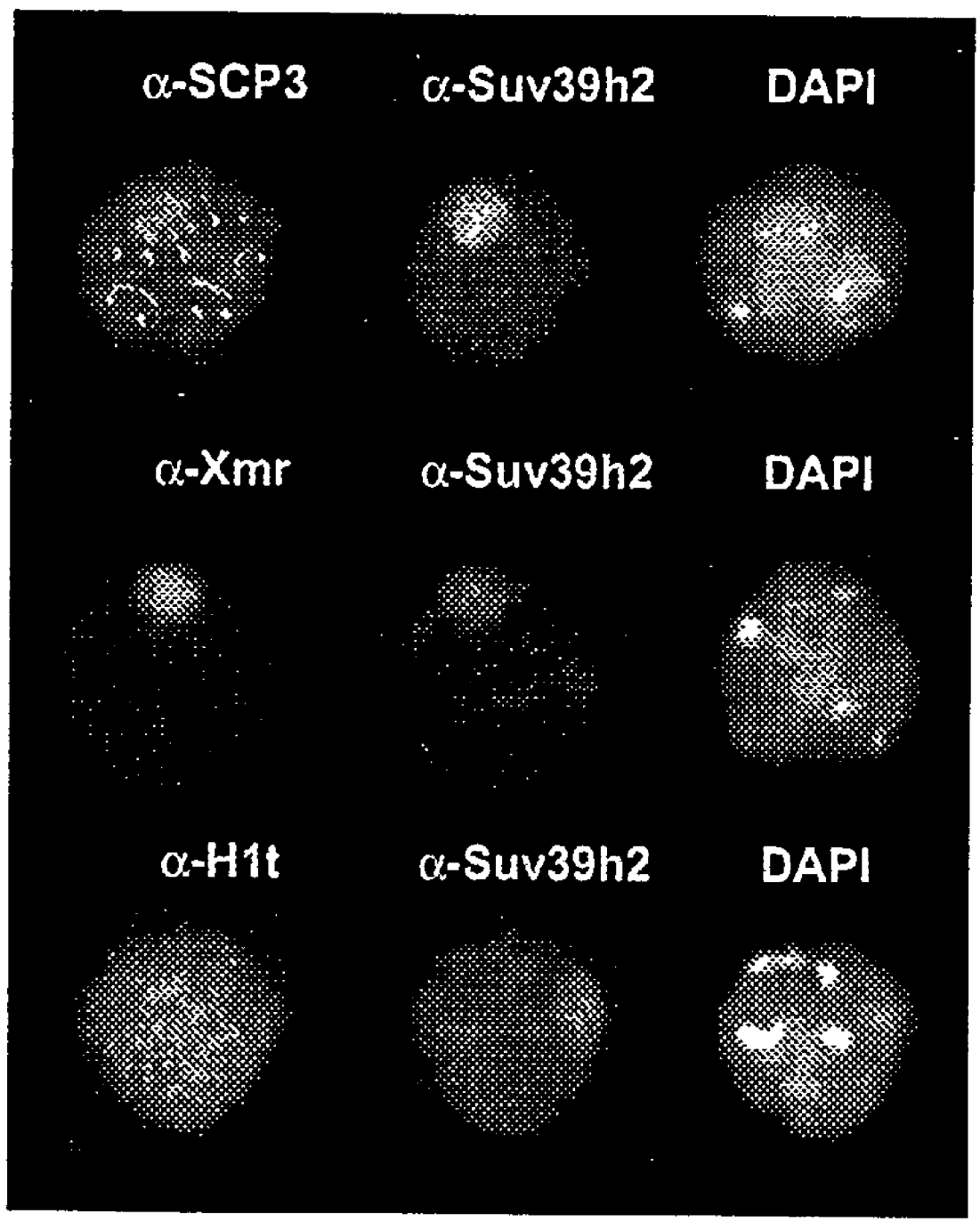
FIG. 7: Suv39h2 accumulates with sex chromosomes present in the X-Y body.

To demonstrate the specific accumulation of Suv39h2 with the sex chromosomes, double immunofluorescence analyses for Suv39h2 and SCP3, and for Suv39h2 and Xmr was performed. SCP3 stains the axial cores of the synaptonemal complex (SC) which is formed during homologue pairing of autosomes (Lammers et al., 1994). By contrast, the Xmr protein selectively associates with the axes and chromatin of sex chromosomes (Calenda et al., 1994), which are enclosed in the XY body during pachytene and whose pairing is delayed relative to the autosomes. The results of these co-localisations show that the concentration of the Suv39h2 signal overlaps with a diffuse SCP3 staining around the unpaired axes of the sex chromosomes but not with the SC of paired autosomes (FIG. 7, top panel). Moreover, Suv39h2 co-localizes with the XY body, as defined by Xmr staining and the presence of unpaired axial cores of the sex chromosomes (FIG. 7, middle panel). These data indicate that Suv39h2 specifically accumulates with chromatin of the sex chromosomes in late prophase of meiosis I. To more definitively determine the timing and differentiation stage at which Suv39h2 accumulates with the sex chromosomes, this analysis was extended by double immunofluorescence for Suv39h2 and the testis-specific histone H1 variant H1t (Meistrich, 1987). H1t appears in mid-pachynema and is detected until haploid spermatids reach the elongation stage. In developing spermatocytes, H1t therefore defines spermatocytes I from mid-pachytene to diplotene (Moens, 1995). Analysis of H1t-stained pachytene nuclei revealed the simultaneous presence of a Suv39h2-positive XY body (FIG. 7, bottom panel), indicating specific association of Suv39h2 with sex chromosomes from mid-late pachytene to diplotene.

FIG. 7: shows the results of double-labelling indirect immunofluorescence for Suv39h2 and either SCP3 (top panel), Xmr (middle panel), or histone H1t (bottom panel) in mid-pachytene to diplotene spermatocytes of adult testis suspensions. DNA was counterstained with DAPI (FIG. 7).

EXAMPLE 8

Suv39h2 Harbours HMTase Activity

The SET domains of SU(VAR)3-9 protein family shares significant sequence and secondary structure with six plant MTases (Rea et al., 2000). Because the SET domain is one of the most conserved protein motifs in chromatin regulators (Stassen et al., 1995; Jenuwein et al., 1998), it was analyzed whether SU(VAR)3-9 family members or other SET domain proteins contain HMTase activity. GST-fusion products of the extended SET domains of murine Suv39h2, S.pombe CLR4 (Ivanova et al., 1998), human EZH2 (Laible et al., 1997) and human HRX (Tkachuk et al., 1992) were generated that would correspond to GST-SUV39H1(82–412) and assayed for HMTase activity. The SU(VAR)3-9 family members assayed, SUV39H1, Suv39h2 and CLR4, displayed HMTase activity. By contrast, both GST-EZH2 (382–747) and GST-HRX(3643–3966) had undetectable HMTase activity towards free histones (FIG. 8B)

FIG. 8A shows a diagram representing the domain structures of CLR4, Suv39h2, SUV39H1, EZH2 and HRX proteins, with the arrowheads demarcating the N-terminal fusion to GST. Cysteine-rich regions are indicated by grey stippling.

In the experiment of FIG. 8B, approximately 10 µg of the indicated fusion proteins encoding S.pombe CLR4 [GST-CLR4(127–490)], murine Suv39h2 [GST-Suv2(157–477)], human EZH2 [GST-EZH2(382–747)], human HRX [GST-HRX(3643–3969)] and human SUV39H1 [GST-SUV1 (82–402)] were used in in vitro HMTase reactions with free histones as outlined in the materials and methods.

EXAMPLE 9

Targeting the Suv39h1 and Suv39h2 Loci in the Mouse Germline

Figure 9A:
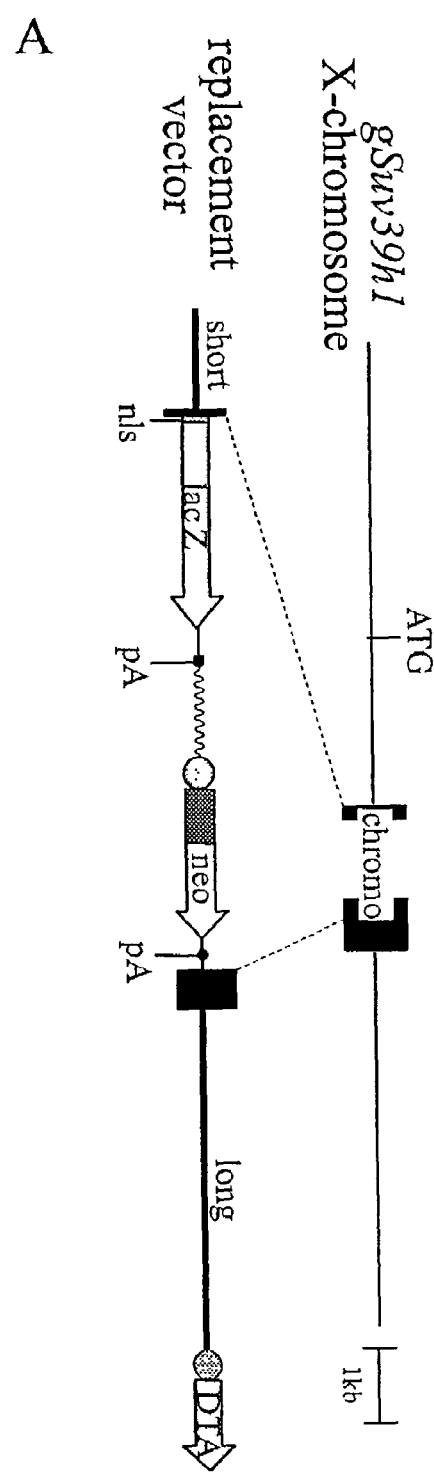

Murine Suv39h genes are encoded by 2 loci, Suv39h1 and Suv39h2.To investigate the in vivo significance of Suv39h function and Suv39h dependent K9 H3 methylation, mouse strains deficient for both Suv39h1 and Suv39h2 were generated according to standard techniques. The targeting strategies are shown in FIG. 9A–9B, as well as demonstrating the production of null alleles for both Suv39h1 and Suv39h2. Mutation of either gene results in viable and fertile mice as a consequence of functional redundancy between both loci. Therefore, Suv39h1 and Suv39h2 deficient strains were intercrossed to produce Suv39h double deficient mice. Double mutant mice are born in sub-Mendelian ratios, approximately 20% of the expected double mutants are observed.

FIG. 9A shows the conventional targeting strategy used to inactivate the X-linked Suv39h1 locus. FIG. 9B shows the Northern blot analysis of Suv39h1 from spleen (Sp), liver (Li), kidney (Kidney), and brain (Br) from wild-type and Suv39h1 null mice. FIG. 9C shows the conventional targeting strategy used to inactivate the autosomal Suv39h2 locus. (Bottom panel) Western blot analysis with anti-Suv39h2 antibodies on protein extracts derived from wild-type and Suv39h2 null testis.

EXAMPLE 10

Suv39h Function Is Required for Male Gametogenesis

In the experiments conducted, it was observed that surviving double mutants are growth retarded and display hypogonadism (FIG. 10A) accompanied by apoptotic spermatogonia. In the few surviving spermatids, the progressive clustering of centromeres that occurs during spermiogenesis is severelyimpaired. Histological analysis of double mutant testis reveals highly aberrant tubules devoid of mature sperm rendering Suv39h double deficient mice infertile (FIG. 10B).

FIG. 10A: shows testis isolated from a wild-type and a Suv39h double null mice. FIG. 10B shows the histological analysis of testis isolated from a wild-type and a Suv39h double null mouse. Shown are sections of seminiferous tubules, Suv39h double null tubules are devoid of mature sperm.

EXAMPLE 11 a) Generation of Suv39h Double Deficient Mice

Figure 11B:
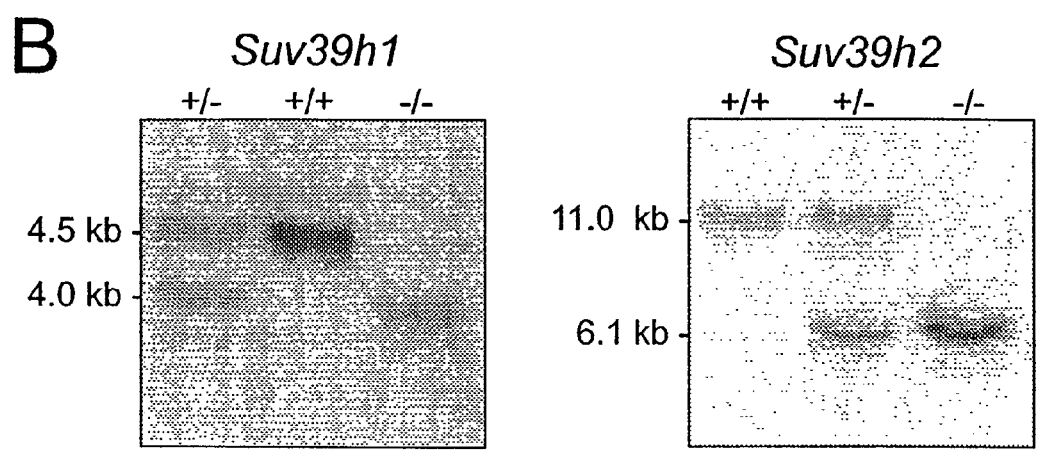
Figure 11C:
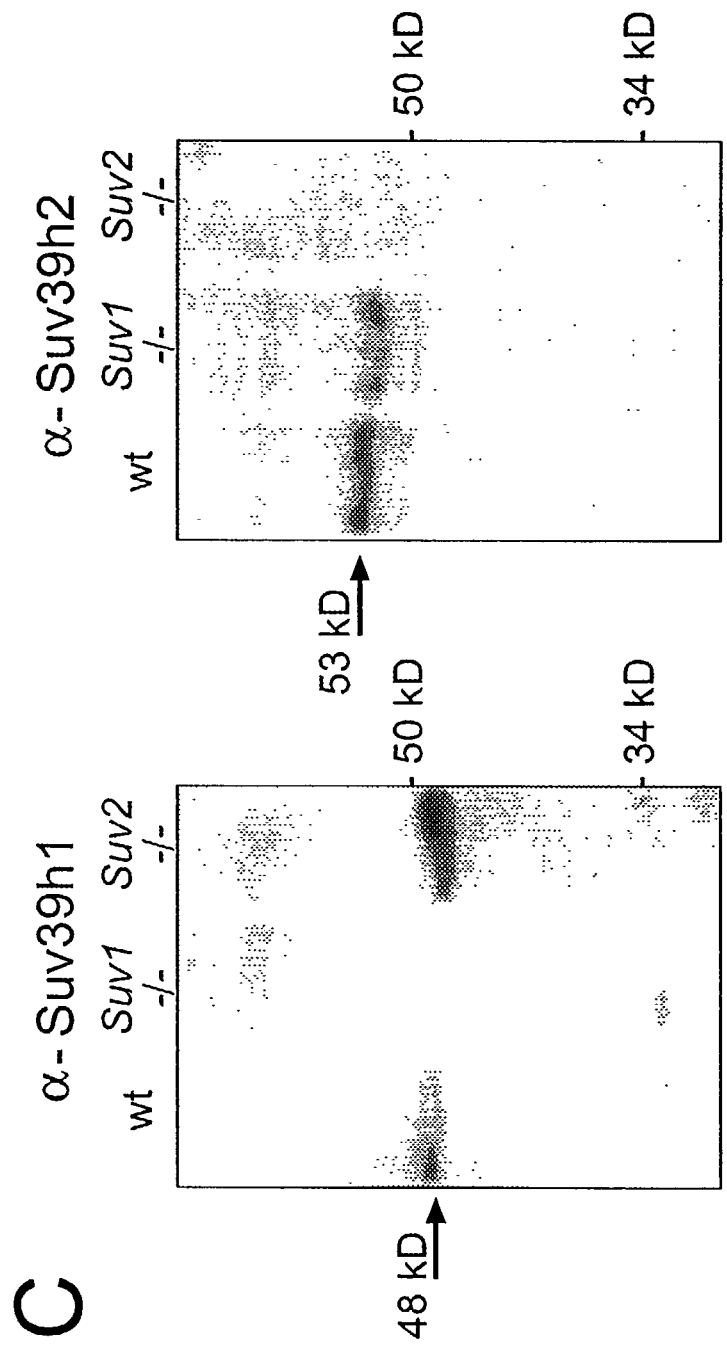

Murine Suv39h HMTases are encoded by two loci which have been mapped to centromere-proximal positions in the X chromosome (Suv39h1) or in chromosome 2 (Suv39h2) (O'Carroll et al., 2000). Both gene loci were independently disrupted by homologous recombination in embryonic stem (ES) cells using a conventional targeting approach that replaces parts of the evolutionarily conserved chromo domain with the bacterial LacZ gene and an RSV-neomycin selecion cassette (FIG. 11A). These targeting strategies produce in-frame fusion proteins of the first 40 amino acids of Suv39h1 or of the first 113 amino acids of Suv39h2 with lacZ, which maintain β-galactosidase activities. Successfully targeted ES cell clones were used to generate chimaeric mice that transmitted the mutated Suv39h1 or Suv39h2 alleles through the germ line (FIG. 11B). Protein blot analyses of testis nuclear extracts from wild-type, Suv39h1- and Suv39h2-deficient mice with α-Suv39h1 and α-Suv39h2 specific antibodies (Aagaard et al., 1999; O'Carroll et al., 2000) indicated the absence of the respective proteins, demonstrating that had been generated loss-of-function alleles for both genes (FIG. 11C).

b) Impaired Viability of Suv39h Double Null Mice

Figure 11D:
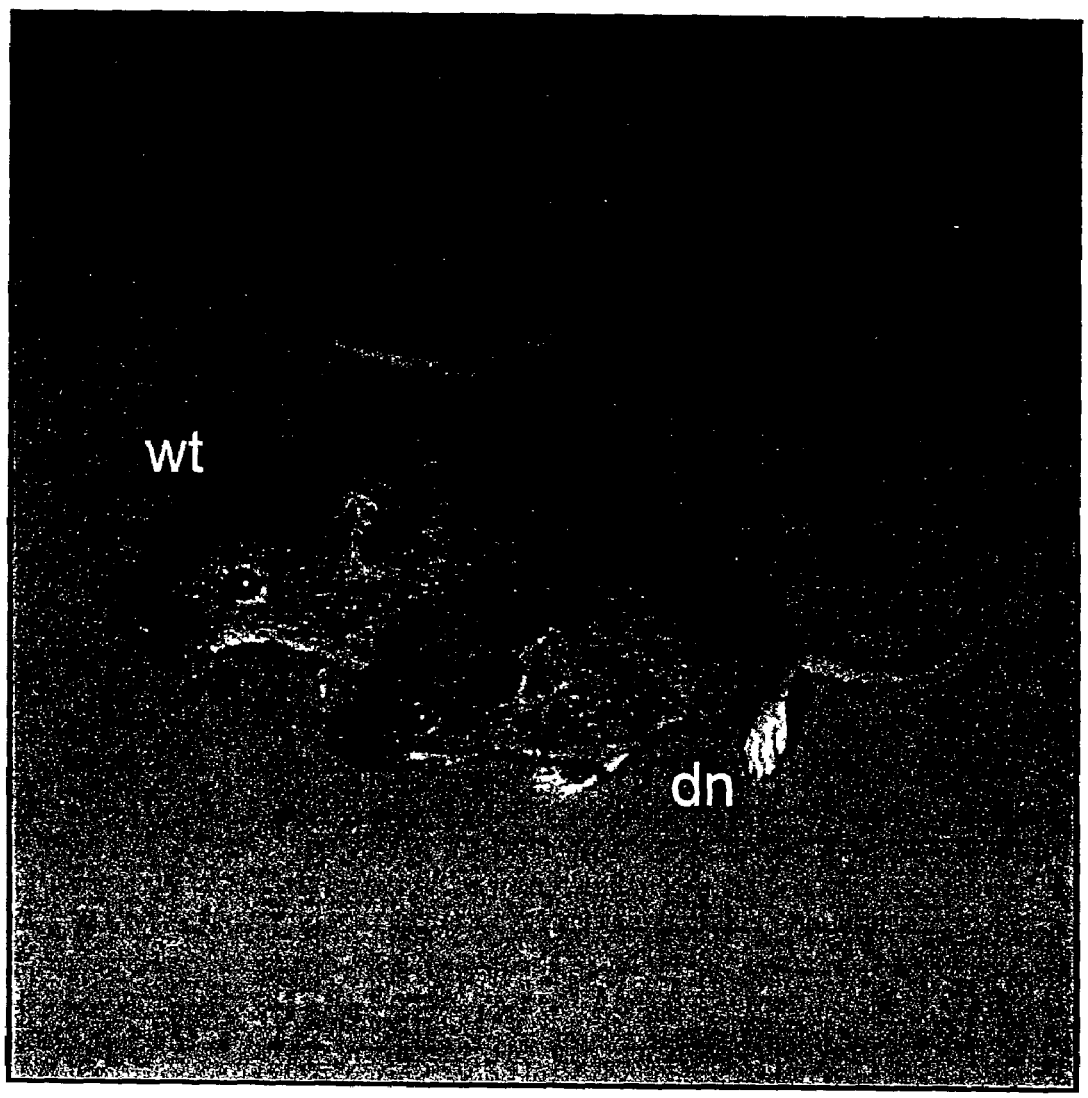

Mice deficient for either Suv39h1 or Suv39h2 display normal viability and fertility, and do not exhibit apparent phenotypes, suggesting that both genes may be functionally redundant during mouse development (O'Carroll et al., 2000). Therefore, Suv39h1−/− and Suv39h2−/− mice were intercrossed to generate compound Suv39h mutants that were then used to derive Suv39h double null (dn) mice. Suv39h dn mice obtained from several different intercrosses (Table I) are born at only sub-Mendelian ratios, are growth retarded (FIG. 11d) and are characterized by hypogonadism in males. For example, from a total of 197 mice, 46 mice would have been expected to be double null (Table I), but only 15 Suv39h dn mice (≈33%) were born. Analysis of mouse embryogenesis indicated normal development of Suv39h dn fetuses until day E12.5, whereas at later stages, Suv39h dn fetuses are smaller and display an increased rate of resorptions and prenatal lethality. Together, these results demonstrate that the Suv39h genes are required for normal viability, and for pre- and postnatal development.

FIG. 11A–11D shows the targeting and genotyping of Suv39h1- and Suv39h2-deficient mice as follows: (FIG. 11A) Diagrammatic representation of the Suv39h1 and Suv39h2 genomic loci, the replacement vectors and the targeted alleles. Exons are indicated by black boxes with numbers referring to the starting amino acid positions of the respective exons (O'Carroll et al., 2000). Also shown are the diagnostic restriction sites and the external probes used for Southern blot analyses. pA indicates polyadenylation signals. (FIG. 11B) Southern blot analyses of PvuII- or HindIII-digested DNA isolated from offspring of Suv39h1+/− or Suv39h2+/− heterozygous intercrosses. (FIG. 11C) Protein blot analyses of testis nuclear extracts from wild-type (wt), Suv39h1−/− (Suv1−/−) and Suv39h2−/− (Suv2−/−) mice with α-Suv39h1 and α-Suv39h2 antibodies. The size of the Suv39h1 or Suv39h2 proteins is indicated by arrows. (FIG. 11D) Suv39h double null (dn) mice are growth retarded at birth and during adulthood.

EXAMPLE 12

Chromosome Mis-segregation in Suv39h dn Embryonic Fibroblasts

To examine the Suv39h-dependent defects in more detail, primary mouse embryonic fibroblasts (PMEFs) were derived from day E12.5 fetuses. Comparative growth curves between wild-type (wt) and Suv39h dn PMEFs in a 3T3 protocol over the first 20 passages indicated that Suv39h dn PMEFs displayed a higher doubling rate until passage 12 (FIG. 12A). At later passages, the Suv39h dn PMEFs appear to have a slightly reduced proliferative potential than the immortalised wt PMEFs which survived the characteristic Hayflick crisis. It was shown recently (see Example 6) that Suv39h dn PMEFs contain a significant fraction of cells with aberrant nuclear morphologies, such as macro- and polynuclei, which are reminiscent of impaired mitosis and chromosome mis-segregation (Rea et al., 2000). Therefore the DNA content of passage 3 and passage 8 wt and Suv39h dn PMEFs was analyzed by FACS. Whereas wt PMEFs appear genomically stable at passage 3, Suv39h dn PMEFs already contain cells with a greater than 4N DNA content, as indicated by the aneuploid shoulder in the FACS profile (FIG. 12B, top panels). At passage 8, wt PMEFs are largely senesced. By contrast, Suv39h dn PMEFs continue to proliferate, although many cells display octaploid DNA contents (FIG. 12B, lower panels).

Figure 12C:
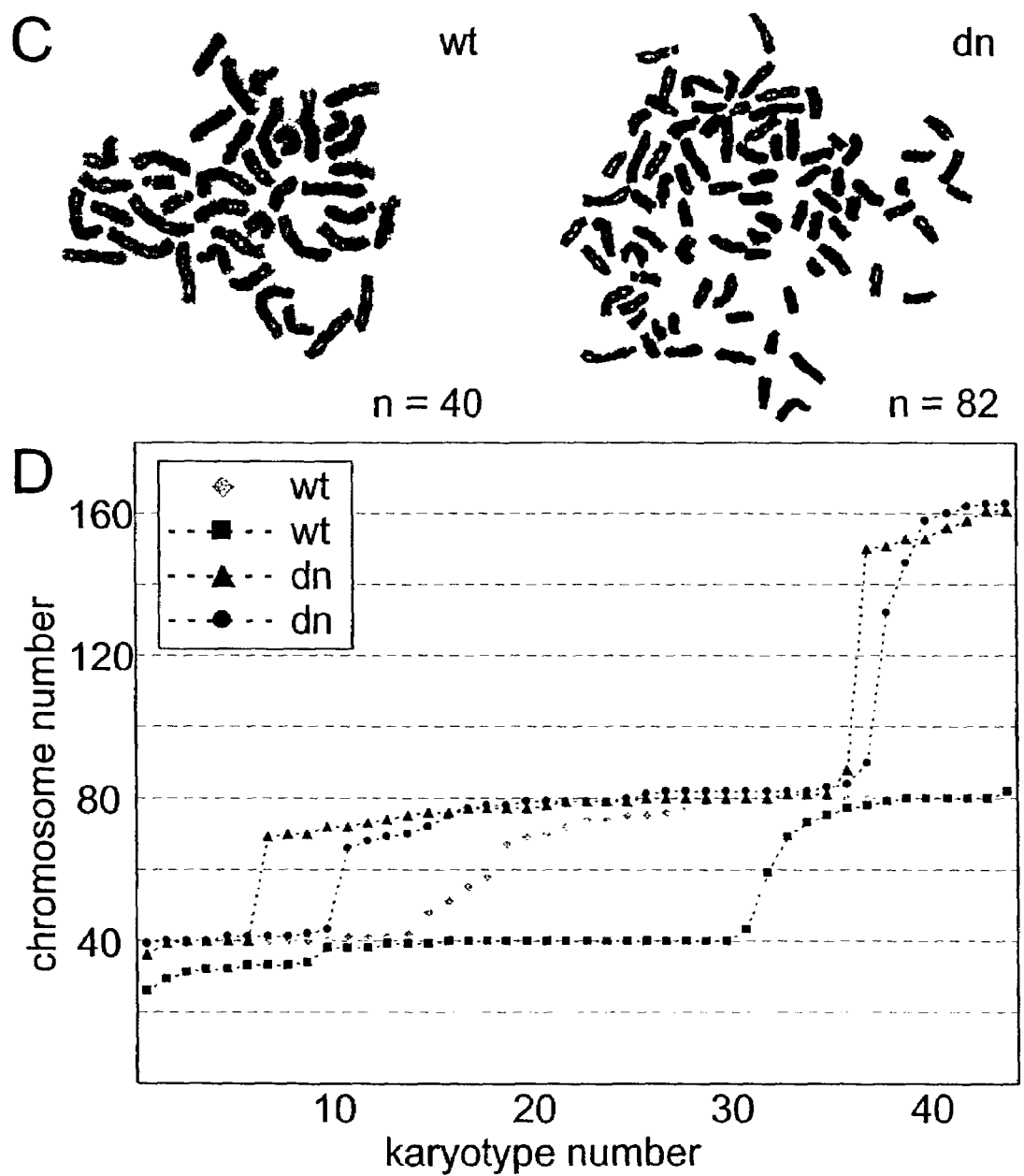

To further characterize these genomic instabilities, karyotype analyses with passage 8 PMEFs were performed (FIG. 12C). In particular, 45 karyotypes each for two independent wt and two Suv39h dn PMEF cultures were examined. As shown in FIG. 12D, a major fraction of the wt karyotypes are non-diploid, with chromosome numbers ranging from 25 to 82. Aneuploidies were significantly increased in Suv39h dn karyoptypes and comprised chromosome numbers from 38 to 162. Notably, whereas wt PMEFs contain a random array of aneuploid karyotypes, Suv39h dn PMEFs are largely hypo-tetraploid or hypo-octaploid. Chromosomes in Suv39h dn PMEFs appear of normal morphology and Robertsonian fusions were not observed. It was concluded that the absence of Suv39h function induces genomic instabilities, primarily by impairing segregation of the entire set of chromosomes.

FIG. 12 shows the chromosomal instabilities in Suv39h dn PMEFs as follows: (A) Relative doubling rates of wt and Suv39h dn PMEFs determined in a 3T3 protocol over the first 20 passages. (B) DNA contents of wt and Suv39h dn PMEF mass cultures at passage 3 and passage 8. (C) Metaphase spreads showing a diploid number (n=40) of chromosomes for wt and a hyper-tretraploid number (n=82) of chromosomes for Suv39h dn PMEFs. (D) Statistical karyotype analysis with two wt and two Suv39h dn PMEF cultures at passage 8. For each culture, 45 metaphases were evaluated.

EXAMPLE 13

Development of B-cell Lymphomas in Suv39h Mutant Mice

Next, Suv39h mutant mice were analyzed for the incidence of tumorigenesis. Because the majority of Suv39h dn mice are non-viable, distinct Suv39h genotypes that differ in their gene dosage for either Suv39h1 or Suv39h2 were examined. For example, it was expected that random X-inactivation of the X-linked Suv39h1 gene could increase the tumor risk in Suv39h1+/− mice, even in the presence of a functional copy of Suv39h2 which is significantly downregulated in most adult tissues (O'Carroll et al., 2000). Indeed, examination of 98 mice which are either heterozygous (het) or null for the Suv39h1 locus indicated an ≈28% penetrance of tumor formation with an onset between 9–15 months of age (Table II). These tumors are predominantly B-cell lymphomas (FIG. 13A) that resemble by FACS profiling (see Materials and Methods) slowly progressing non-Hodgin lymphomas in humans (Foon and Gale, 1995). The tumor incidence for late onset B-cell lymphomas was ≈33% in the few viable Suv39h dn mice (n=6). By contrast, Suv39h2+/− or Suv39h2−/− mice developed B-cell lymphomas at only ≦5% penetrance (n=21), and tumor formation in control wild-type mice was not observed.

Figure 13C:
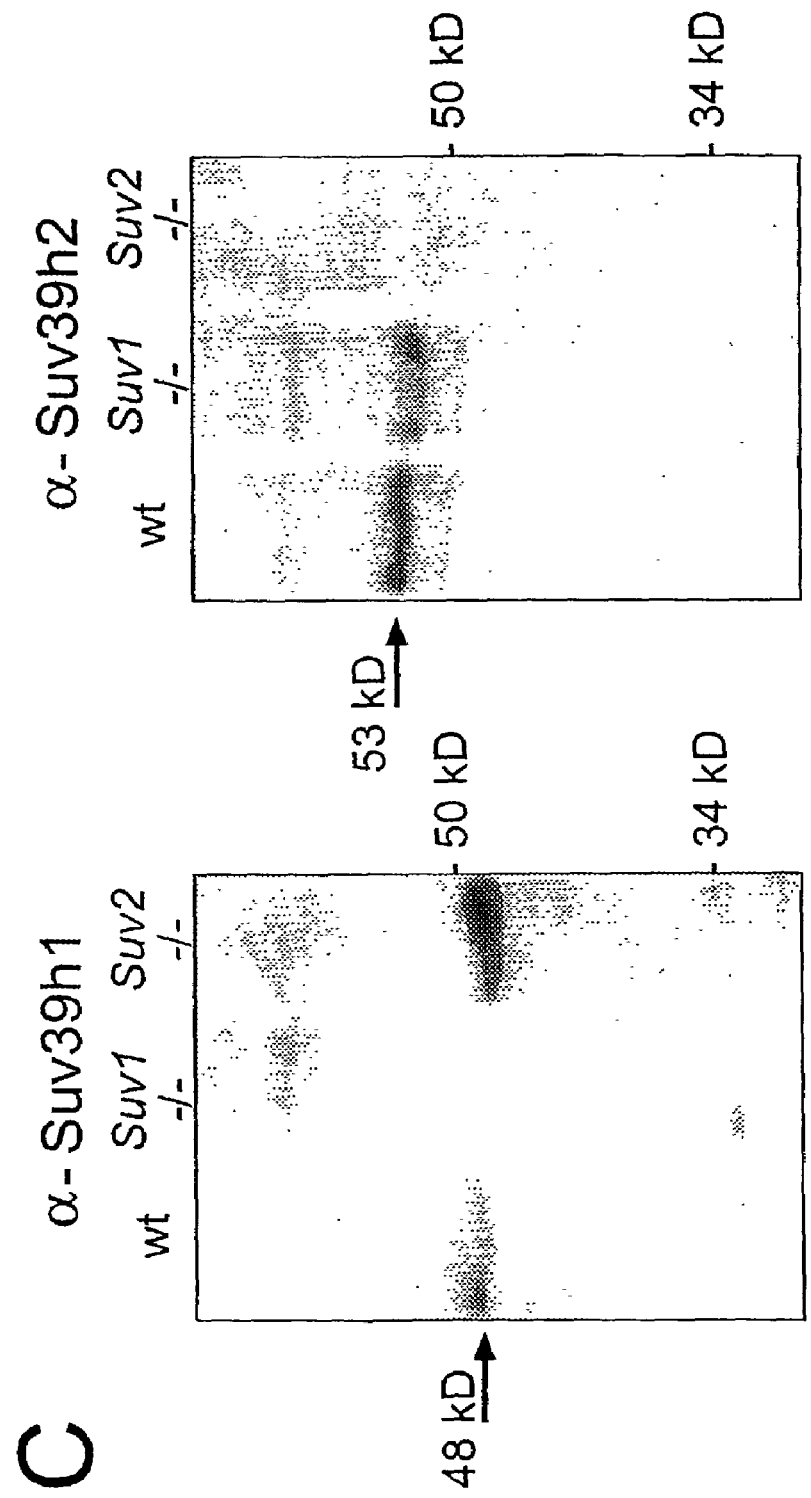

Primary cultures were derived from the lymph nodes of Suv39h dn and of Suv39h1−/−, Suv39h2+/− (null1/het2) tumor mice, and analyzed the karyotypes of the B-cell lymphoma cells. Consistent with the aneuploides described above for Suv39h dn PMEF mass cultures, these tumor cells were largely hyper-diploid but also comprised some hyper-tetraploid karotypes (FIG. 13B). Surprisingly, a fraction of Suv39h dn tumor karyotypes, examined in several independent B-cell lymphomas, is characterized by non-segregated chromosomes that remain attached through their acrocentric regions (FIG. 13C). These 'butterfly' chromosomes raise the intriguing possibility that the absence of Suv39h HMTase activities could impair the quality and function of pericentric heterochromatin by increasing more persistent interactions between metaphase chromosomes. Indeed, analysis of H3-K9 methylation with a newly developed antibody (see Example 11, below) indicates the absence of methH3-K9 staining at pericentric heterochromatin of tumor chromosomes derived from Suv39h null1/het2 B-cell lymphoma cells.

FIG. 13A–13C shows the development of B-cell lymphomas in Suv39h mutant mice as follows: (FIG. 13A) Spleen and lymph nodes of an 11-month old Suv39h dn tumor mouse and of a wild-type control mouse. (FIG. 13B) Karyotype analysis of four independent primary cultures derived from the lymph nodes of tumor-bearing Suv39h dn (null1/null2) and Suv39h1−/−, Suv39h+/− (null1/het2) mice. (FIG. 13C) Metaphase spread from a primary Suv39h dn B-cell lymphoma cell showing 'butterfly' chromosomes that remain associated through their acrocentric regions.

EXAMPLE 14

Absence of H3-K9 Methylation at Suv39h dn Heterochromatin

Figure 14A:
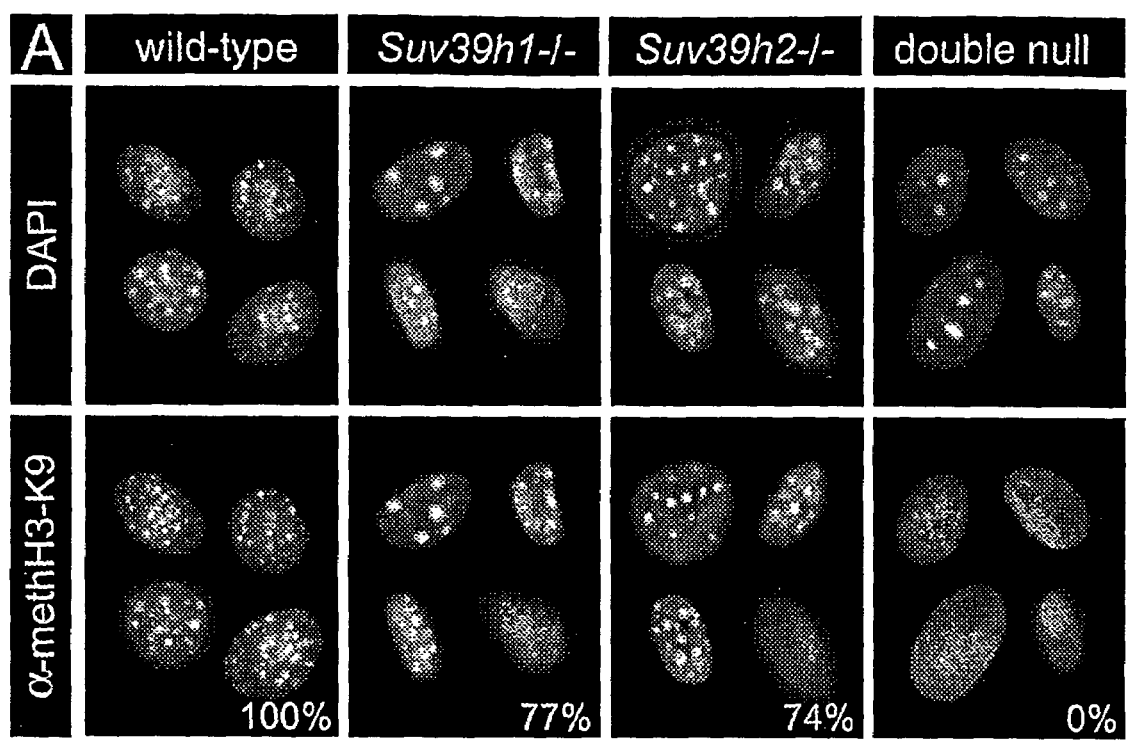
FIG. 14A–14B: Suv39h-dependent H3-K9 methylation at pericentric heterochromatin.

The above karyotype analyses on PMEF and tumor cells suggested a general mechanism through which segregation of the entire chromosome complement may be impaired by Suv39h-dependent defects in pericentric chromatin organization. To assess directly the role of the Suv39h HMTases in histone methylation and heterochromatin formation, a rabbit polyclonal antiserum was raised that specifically recognizes histone H3 when di-methylated at lysine 9 (α-methH3-K9). As shown in FIG. 14A, this antiserum detects a focal staining in wt PMEFs that significantly overlaps with DAPI-rich heterochromatin. In PMEFs derived from single Suv39h1- or Suv39h2-deficient mice, ≈75% of cells stain positive for heterochromatic foci with these α-methH3-K9 antibodies. Importantly, heterochromatic staining for methH3-K9 was abolished in Suv39h dn PMEFs (FIG. 14A, right row).

Mitotic chromosome spreads from bone marrow cells were also analyzed with the α-methH3-K9 antiserum. In wt spreads, pericentric heterochromatin was selectively visualised (see inserts in FIG. 14B), whereas only residual staining was detected in Suv39h dn spreads. Thus, consistent with the localization of SUV39H1 at active centromeres (Aagaard et al., 2000), these data demonstrate that both Suv39h enzymes are the major HMTases to methylate H3-K9 in pericentric heterochromatin of somatic cells. Moreover, these results also characterize the α-methH3-K9 antibodies as a novel cytological marker for heterochromatin and corroborate recent *S.pombe* studies, in which enrichment of H3-K9 methylation at MAT and CEN regions was shown to be dependent upon a functional Clr4 enzyme (Nakayama et al., 2001).

Figure 14B:
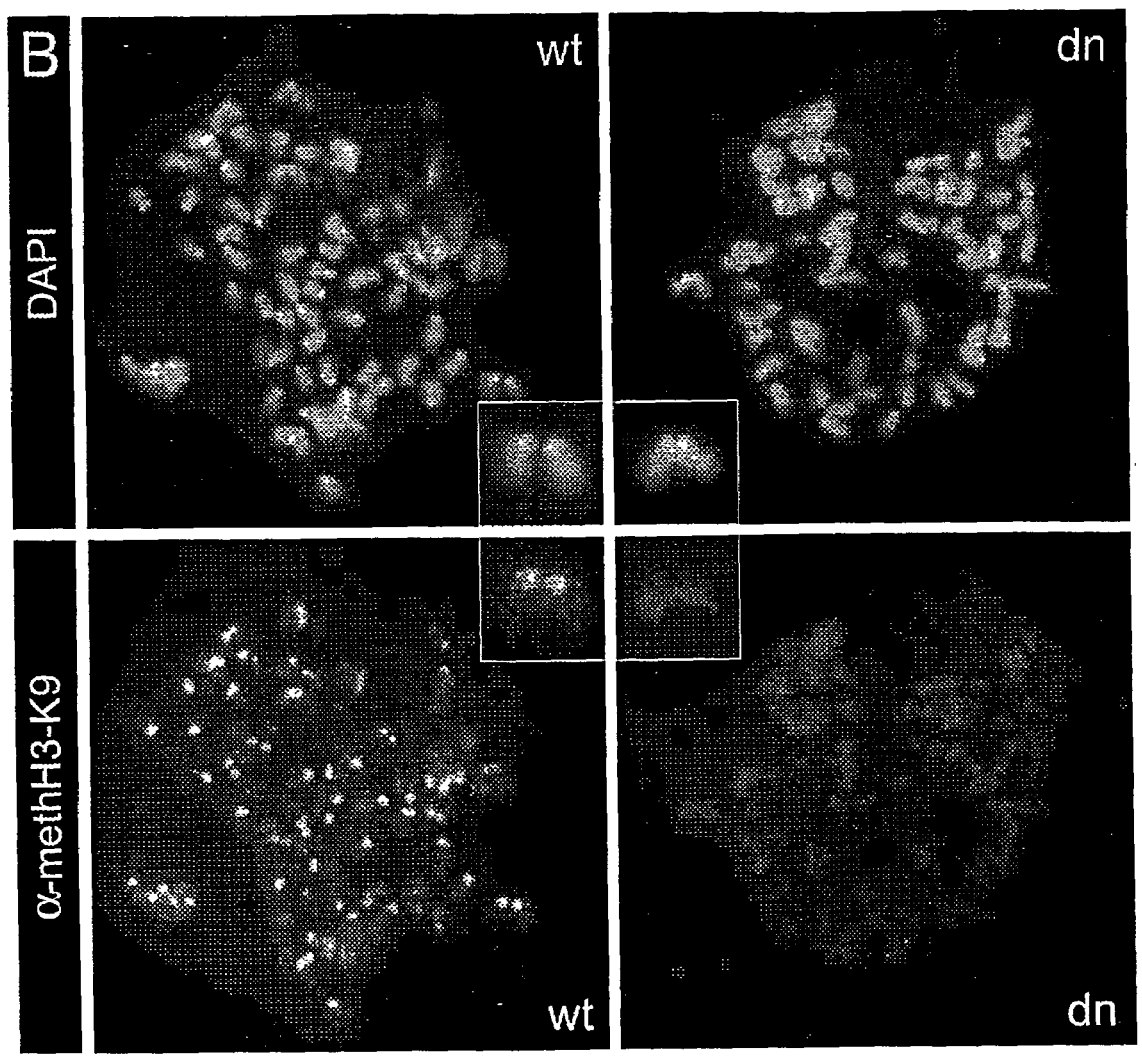

FIG. 14A–14B shows the Suv39h-dependent H3-K9 methylation at pericentric heterochromatin as follows: (FIG. 14A) DAPI and methH3-K9 staining on interphase chromatin of wild-type (wt), Suv39h1−/−, Suv39h2−/−, and Suv39h dn PMEFs. Percentages refer to interphase nuclei displaying H3-K9 methylation at heterochromatic foci. (FIG. 14B) DAPI and methH3-K9 staining on mitotic chromosomes prepared from in vitro cultured wt and Suv39h dn bone marrow cells.

EXAMPLE 15 a) Hypogonadism and Complete Spermatogenic Failure in Suv39h dn Mice

Figure 15A:
FIG. 15A–15B: Spermatogenic failure and H3-K9 methylation in germ cells of Suv39h dn mice.

The expression pattern of the Suv39h genes suggests an important role during spermatogenesis (O'Carroll et al., 2000). Indeed, Suv39h dn males (n=7) are infertile, do not contain mature sperm and their testis weights are 3–10 fold reduced as compared to that of wt males (FIG. 15A). To investigate the spermatogenic failure in more detail, histological sections were performed, demonstrating normally developed seminiferous tubules in wt testis which display the characteristic differentiation from the mitotically proliferating spermatogonia (Sg) to meiotic spermatocytes (Sc) and the post-meiotic haploid spermatids (St) (FIG. 15A). By contrast, spermatogenesis was severely impaired in Suv39h dn mice, with an apparent differentiation arrest at the transition between early to late spermatocytes, resulting in highly vacuolarized seminiferous tubules (FIG. 15A).

FISH analyses with mouse major satellite DNA probes and TUNEL assays were used to characterize the Suv39h-dependent spermatogenic defects further. Whereas mitotic proliferation of spermatogonia appeared normal, a 3 to 10 fold increase in the percentage of pre-leptotene spermatocytes was observed. These pre-leptotene spermatocytes often were enlarged. These results suggest that the entry into meiotic prophase is delayed in the absence of Suv39h function. Despite this delay, further progression through meiotic prophase until mid-pachytene appeared normal. Between mid- to late pachytene, however, most spermatocytes undergo apoptosis, resulting in stage V–VI tubules (see FIG. 15A) that largely lack late pachytene spermatocytes and which do not contain haploid spermatids. It was concluded that the absence of Suv39h gene function induces delayed entry into meiotic prophase and triggers pronounced apoptosis of spermatocytes during the mid- to late pachytene stage.

b) H3-K9 Methylation at Meiotic Heterochromatin

Figure 15B:
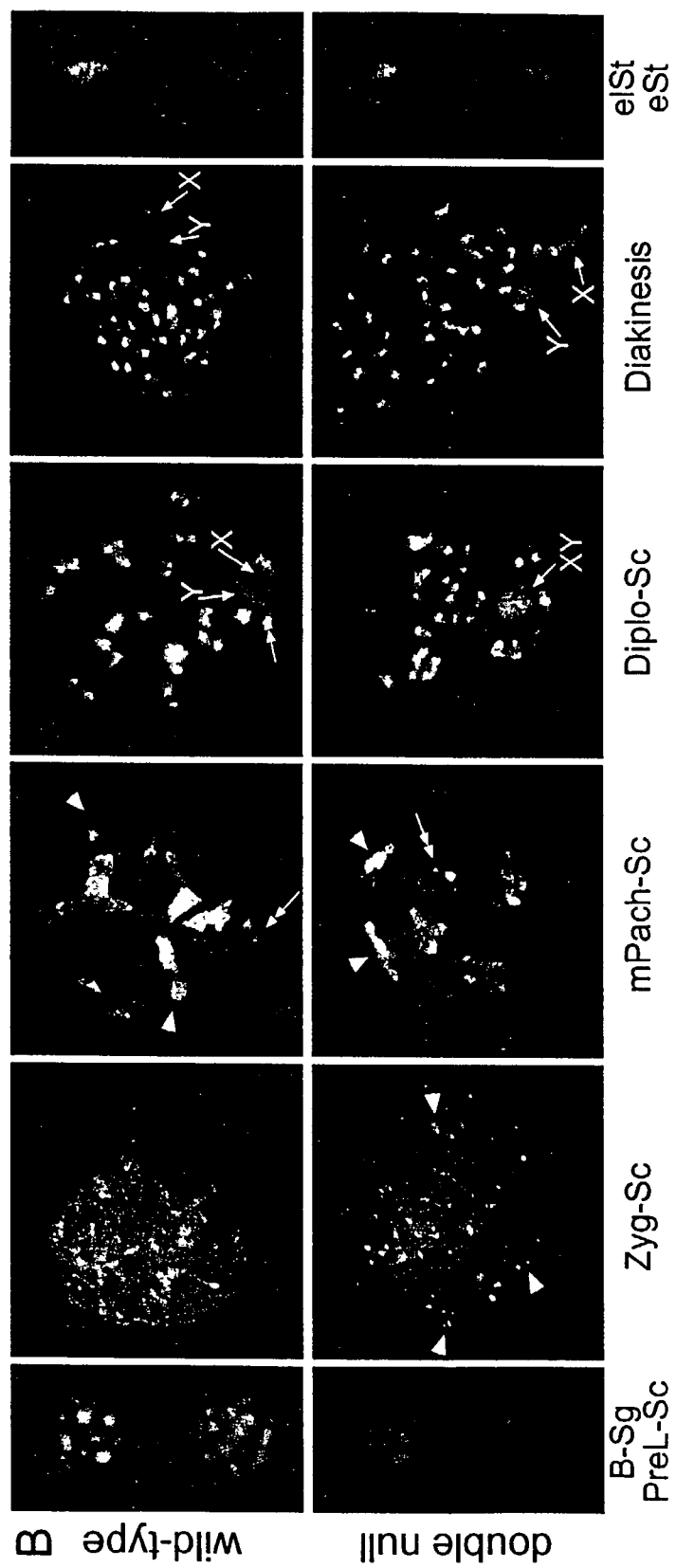

To investigate whether the Suv39h-dependent spermatogenic failure could be correlated with a distinct impairment of meiotic heterochromatin, testis spread preparations and cryosections were analyzed with the α-methH3-K9 antibodies. In wt preparations, the α-methH3-K9 antibodies decorate heterochromatic foci in spermatogonia (B-Sg) and in pre-leptotene spermatocytes (preL-Sc) (FIG. 15B, left images, top panel). In early meiotic prophase (Zyg-Sc) and early pachytene, the α-methH3-K9 staining was not exclusive for heterochromatin but also extended into euchromatin. From mid-pachytene through diplotene and in diakinesis, the α-methH3-K9 staining was restricted to heterochromatic clusters which condense into one block of heterochromatin in elongating spermatids (FIG. 15B, top panels). MethH3-K9 signals in elongated spermatids and mature spermatozoa, in which histones are replaced by protamines, were not detect. The authenticity of this staining pattern had been confirmed in co-localisation analyses with antibodies that recognize the synaptonemal complex (Offenberg et al., 1991; Lammers et al., 1995), HP1β (Motzkus et al., 1999) and phosH3 (Cobb et al., 1999). Thus, in analogy to the somatic stainings shown above for PMEFs, these results indicate that methylation of H3-K9 is also a specific marker for meiotic heterochromatin in differentiating male germ cells.

c) Impaired H3-K9 Methylation and Aneuploidies in Suv39h dn Spermatogonia

In preparations from Suv39h dn testis spreads, H3-K9 methylation was absent in spermatogonia and pre-leptotene spermatocytes (FIG. 15B, left images, bottom panel). Further, the pronounced euchromatic staining that characterizes early spermatocytes (Zyg-Sc) at the onset of meiotic prophase was not observed. The impairment of H3-K9 methylation was accompanied by a dispersed distribution of phosH3 in ≈60% of Suv39h dn spermatogonia. By contrast, HP1β was largely undetectable in both wt and Suv39h dn spermatogonia.

Surprisingly, from mid-pachytene onwards, wild-type staining for methH3-K9 at pericentric heterochromatin was observed (FIG. 15B, bottom panel). HP1β localisation and phosH3 signals at autosomes ocurred normally in Suv39h dn late spermatocytes. Thus, these results demonstrate that the Suv39h HMTases selectively regulate H3-K9 methylation in spermatogonia and at the very early stages of meiotic prophase. Similar to the analysis with PMEFs (see above), an ≈5-fold increased rate for complete chromosome mis-segregation in Suv39h dn spermatogonia that results in the occurence of tetraploid spermatocytes ws observed (see FIG. 16C, below). In summary, these data define an early and stage-specific meiotic role for the Suv39h HMTases, and further suggest the existence of a novel H3-K9 HMTase(s) which can methylate heterochromatin during meiotic prophase, diakinesis and in spermatids.

FIG. 15 shows the spermatogenic failure and H3-K9 methylation in germ cells of Suv39h dn mice as follows: (A) Overall size and histology of wild-type and Suv39h dn testes at ≈5 months of age. The Suv39h dn testis section reveals many seminiferous tubules that lack spermatocytes (Sc) and spermatids (St). In particular, although a few seminiferous tubules (1) contain zygotene spermatocytes (Zyg-Sc), more advanced differentiation stages (2) display apoptotic spermatocytes (arrows) at pachytene. At even later differntiation stages (3), pachytene spermatocytes are almost completely absent. Some tubules (4) harbor only Sertoli cells (SeC). Abbreviations: Intermediate (In-Sg) and B-type spermatogonia (B-Sg); pre-leptotene (PreL-Sc), zygotene (Zyg-Sc), mid-pachytene (mPach-Sc), late-pachytene (lPach-Sc), diplotene (Diplo-Sc) and diakinesis/M-I (M-I-Sc) spermatocytes; round (rSt), elongating (elSt) and elongated (eSt) spermatids; Sertoli cells (SeC).

(FIG. 15B) Double-labelling immunofluorescence of wt (top panel) and Suv39h dn (bottom panel) germ cells with α-methH3-K9 (pink) and α-Scp3 (green) antibodies. DNA was counterstained with DAPI (blue). In Suv39h dn germ cells, H3-K9 methylation is absent in proliferating spermatogonia (B-Sg) and in pre-leptotene spermatocytes (PreL-Sc), and is highly reduced in zygotene spermatocytes (Zyg-Sc) where only residual signals are detected at pericentric heterochromatin (arrowheads). At later stages, H3-K9 methylation appears in a wild-type staining (compare top and bottom panels), although Suv39h dn sex chromosomes (arrows) remain more intensely labeled at diplotene and diakinesis. The double arrow indicates the pseudo-autosomal region (PAR).

EXAMPLE 16 a) Non-homologous Interactions and Delayed Synapsis in Suv39h dn Spermatocytes

The absence of pericentric H3-K9 methylation in spermatogonia and early spermatocytes is suggestive for a role of the Suv39h HMTases in defining a higher-order structure that may be required for the initial alignments and clustering of meiotic chromosomes. Therefore chromosome synapsis was analyzed by immunofluorescence of pachytene spreads with antibodies that are specific for the axial/lateral and central elements of the synaptonemal complex (SC) (FIGS. 16A,B). Intriguingly, in ≈15% (n=90) of Suv39h dn spermatocytes, non-homologous interactions between autosomes were observed (FIG. 16J). Non-homologous interactions were even more frequent (≈35%) between sex chromosomes and autosomes (X/Y-A). Interestingly, these illegitimate associations occurred predominantly between the acrocentric ends (cen-cen) of non-homologous chromosomes, to a lesser extent between centromeres and telomeres (cen-tel) and only very rarely between telomeres (tel-tel) (FIG. 16J). In addition, Suv39h dn spermatocytes contained unsynapsed sex chromosomes (see below) and autosomal bivalents that were delayed in synapsis. Delayed synapsis of autosomes (A-del) almost invariably was correlated with engagement in non-homologous associations (FIG. 16A), suggesting that both processes may be functionally related.

The illegitimate associations were further confirmed by transmission electron microscopy (FIGS. 16D–16G). These ultrastructural analyses revealed the presence of physical connections and bridge-like structures between the ends of non-homologous chromosomes (double arrow in FIGS. 16D, 16C, 16F). The incidence of partner exchange (FIG. 16G) and non-homologous alignments were also observed. None of these aberrant chromosomal interactions were detected in EM preparations from wt spermatocytes.

b) Bivalent Mis-segregation at Meiosis I in Suv39h dn Spermatocytes p To determine whether the absence of methH3-K9 in early prophase may affect chromosome dynamics and segregation during the meiotic divisions, testis spread preparations were next analyzed for diakinesis/metaphase I (M-I) and metaphase II (M-II) cells. At diakinesis/M-I, most Suv39h dn spermatocytes revealed bivalents with wt-like morphology, indicating that chromosome condensation and chiasmata formation was unperturbed (but see FIGS. 17B–D, below). However, at M-II, ≈14% of secondary spermatocytes were tetraploid, indicating segregation failure of all bivalents during the first meiotic division (FIGS. 16I and 16K). Therefore, the Suv39h-induced defects at pericentric heterochromatin persist throughout the first meiotic division and do not appear to be 'rescued' by the additional H3-K9 methylation that occurs during mid- to late meiotic prophase (see FIG. 15B).

FIG. 16A–16K shows the illegitimate associations and delayed synapsis of Suv39h dn meiotic chromosomes as follows: (16A–16C) Double-labelling immunofluorescence of Suv39h dn pachytene spermatocytes with antibodies that are specific for the axial/lateral elements α-Scp3 (in green) and central elements α-Scp1 (in red) of the synaptonemal complex (SC). This co-labelling reveals unsynapsed chromosomes in a green-like staining and synapsed chromosomes in an orange-red colour. DNA was counterstained with DAPI (blue) which highlights pericentric heterochromatin in a more intense blue contrast. (FIG. 16A) Two mid-pachytene spermatocytes (mPach-Sc) showing multiple illegitimate associations (arrowheads) between non-homologous autosomes (A) and between autosomes and sex chromomes (X, Y). Several autosomes are also delayed in synapsis ($A_{del}$). (FIG. 16B) Late pachytene (1Pach-Sc) spermatocyte containing two autosomes which are engaged in non-homologous interaction through their pericentric regions (arrowhead). In addition, the sex chromosomes failed to pair. (FIG. 16C) Tetraploid spermatocyte resulting from complete mis-segregation of all chromosomes in the preceding mitotic division of a Suv39h dn spermatogonium.

(16D–16G) Transmission electron microscopy of Suv39h dn pachytene chromosomes, confirming that non-homologous chromosome associations mainly occur through pericentric heterochromatin which is visulised by the more granular silver staining (arrowhead and double arrows). The chromosomes displayed in panel G show multiple engagements of partner exchange.

(FIG. 16H–16I) Giemsa-stained metaphase II chromosomes of wt and Suv39h dn secondary spermatocytes illustrating complete mis-segregation in the preceeding meiosis I division of Suv39h dn cells.

(FIG. 16J) Histogram for the frequency of non-homologous chromosome associations and delayed synapsis in wt (n=80) and Suv39h dn (n=90) pachytene spermatocytes. (FIG. 16K) Histogram for the frequency of meiosis I mis-segregation of chromosome bivalents in wt (n=40) and Suv39h dn (n=30) secondary spermatocytes.

EXAMPLE 17

Suv39h Deficiency Interferes with Sex Chromosome Segregation

Spermatogenesis in male mammals is specialised by the presence of the heteromorphic sex chromosomes which form a unique chromatin region known as the sex vesicle or XY body (Solari, 1974). Moreover, the Y chromosome is the most heterochromatic chromosome in the mouse (Pardue and Gall, 1970). Homolog pairing and cross-over between sex chromosomes is dependent upon the presence of a small, pseudo-autosomal region called PAR (Burgoyne, 1982). The absence of Suv39h function interferes with the chromatin organization and segregation of the sex chromosomes in several ways.

First, although methH3-K9 signals at the XY body (arrows in FIG. 15B) were detected at comparable levels in wt and mutant pachytene spermatocytes, Suv39h dn sex chromosomes remain more heavily methylated in diplotene and diakinesis (see FIG. 15B, bottom panels). Correspondingly, prolonged HP1β binding to the XY body during diplotene was observed. Second, at diakinesis/M-I, the proximal region of the long arm of the Y chromosome appears hypo-condensed in 10% of Suv39h dn cells (FIGS. 17B, E). Moreover, the mutant Y chromosomes display premature separation of their arms or even complete separation of the two sister chromatids (FIGS. 17D, E). Third, H3-K9 methylation is present at the PAR (double arrows in FIG. 15B) in both wt and Suv39h dn sex chromosomes, and the PAR is also decorated with HP1β. Despite these similar staining patterns, the sex chromosomes failed to synapse in ≈15% of Suv39h dn pachytene spermatocytes (FIGS. 16A, B). At diakinesis/M-I (FIGS. 17B, C), the presence of XY univalents was 4-fold increased as compared to wt cells (FIG. 17F). Together, these data indicate a role for the Suv39h HMTases in co-regulating the specialised chromatin structure of the sex chromosomes, in particular of the highly heterochromatic Y chromosome.

FIG. 17 shows the aberrant function of the Y chromosome during meiosis of Suv39h dn spermatocytes as follows: Giemsa-stained diakinesis/metaphase-I chromosomes of wt (FIG. 17A) and Suv39h dn (FIG. 17B–17D) primary spermatocytes illustrating univalency (FIG. 17B, 17C), impaired condensation (FIG. 17B, 17C) and premature sisterchromatid separation of the Y chromosome (FIG. 17C, 17D). (FIG. 17E) Histogram for the frequency of diakinesis/M-I cells with abnormal condensation or premature sisterchromatid separation of the Y chromosome (wt: n=190; Suv39h dn: n=170). (FIG. 17F) Histogram for the frequency of XY univalency at pachytene (wt: n=80; Suv39h dn: n=80) or diakinesis/M-I (wt: n=190; Suv39h dn: n=170).

EXAMPLE 18

Screening for Moduators of Suv39h2 MTase Activity

All steps are automated and the position of the different compounds being tested are registered on computer for later reference. Compounds being tested for modulating activity are aliquoted into 384 well plates in duplicate. 20–200 nmol of recombinant GST tagged human SUV39H2 in MAB buffer, is then added to the reaction. 20 nmol of branched peptide ([TARKST]$_4$-K$_2$-K-cys) which has been labelled with europium is then added, followed by 100 nmol of S-adenosyl methionine. This reaction is left at room temperature for 40 mins, then transferred onto a second plate to which the α-methH3-K9 antibody has been coated. This reaction is then left at room temperature for 40 mins to allow the antibody to bind methylated substrate. Following capture of methylated substrate, unbound non-methylated substrate is washed off in 50 mM tris pH 8.5. The europium label is then cleaved from the peptide in 50 μl pH 4.5 enhancement solution for 25 mins. The chelated europium molecules are then excited at 360 nm and the level of emitted fluorescence at 620nm is then calculated using time-resolved fluorescence in a PolarStar plate reader. The results are then automatically graphed.

The level of fluorescence is directly related to the level of MTase activity. The effect of the different compounds on the MTase activity can be clearly seen on the graph when compared to control reactions with no componds added or with no enzyme added.

Figure 19:
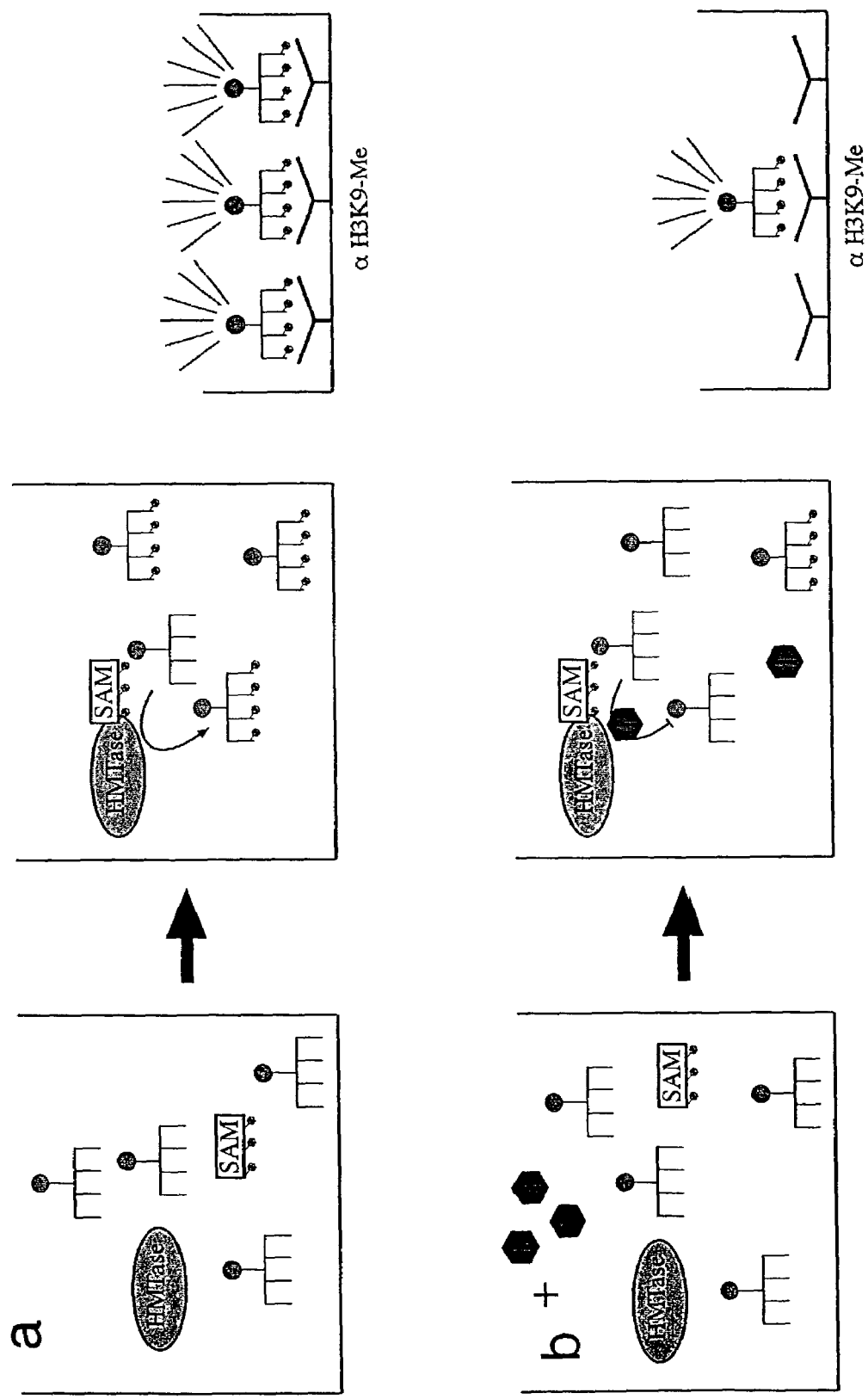
FIG. 19A–19B: Schematic illustration of a screening method for identifying Suv39h2 modulators

FIG. 19A–19B illustrates the principle of the screening method as follows: FIG. 19A: Suv39h2 is incubated with S-Adenosyl Methionine (SAM) and a chromogenically labelled unmodified peptide substrate (e.g. branched peptide [TARKST]4-K2-K-cys). Following methylation of this substrate the substrate becomes an epitope for a Lys9-methyl specific antibody which has been immobilised on a microtiter plate. The level of bound peptide can then be quantified by the level of fluorescence of from the chromogenic label.

FIG. 19B: In the presence of a modulator (e.g. an inhibitor, I) the transfer of methyl groups by the MTase will be affected (decreased), this in turn will affect the amount of substrate captured by the immobilised antibody, which is quantified by the level of fluorescence. A compound with inhibitory effects will result in a decrease in fluorescent signal, whereas a compound with inhibitory effects will result in a decrease in fluorescent signal, whereas a compound with enhancing effects will result in an increase in fluorescent signal.

TABLE I

Viability of Suv39h double null mice.

| cross dn mice expected | N1H2 × H1H2[a] 1:8 | N1H2 × N1H2 1:4 | N1H2 × H1N2 1:4 | total |
|---|---|---|---|---|
| total # mice born | 81 | 89 | 27 | 197 |
| # dn mice expected[b] | 11 | 27 | 8 | 46 |
| # dn mice observed | 4 | 8 | 3 | 15 |
| % dn mice viable | 36.4 | 29.6 | 37.5 | 32.6 |

[a] i.e.: N1H2 × H1H2: ♂♂ Suv39h1−/−, Suv39h2+/− × ♀♀ Suv39h1+/−, Suv39h2+/−
[b] Based on number of mice born with other Suv39h1 and Suv39h2 allelic combinations which show no reduced prenatal viability.

TABLE II

Incidence of B-cell lymphomas in mice with reduced Suv39h gene dosage

| Genotype | Suv39h gene dosage | # of mice with tumor | total # of mice | % of mice with tumor |
|---|---|---|---|---|
| W1W2 | 3 | 0 | 57 | 0 |
| W1H2, W1N2, H1N2 | 0–2 | 1 | 22 | 4.6 |
| H1W2, N1W2 | 2–3 | 8 | 26 | 30.8 |
| H1H2, N1H2* | 1–2 | 20 | 72 | 27.8 |
| N1N2 | 0 | 2 | 6 | 33.3 |

*i.e.: N1H2: Suv39h1−/−, Suv39h2+/−

REFERENCES

Aagaard, L., Laible, G., Selenko, P., Schmid, M., Dorn, R., Schotta, G., Kuhfittig, S., Wolf, A., Lebersorger, A., Singh, P. B., Reuter, G. and Jenuwein, T. (1999) Functional mammalian homologues of the Drosophila PEV-modifier Su(var)3-9 encode centromere-associated proteins which complex with the heterochromatin component M31. Embo J, 18, 1923–38.

Aagaard, L., Schmid, M., Warburton, P. and Jenuwein, T. (2000) Mitotic phosphorylation of SUV39H1, a novel component of active centromeres, coincides with transient accumulation at mammalian centromeres. J Cell Sci, 113, 817–829.

Aasland, R. and Stewart, A. F. (1995) The chromo shadow domain, a second chromo domain in heterochromatin-binding protein 1, HP1. Nucleic Acids Res, 23, 3168–74.

Adams, R. R., Wheatleya, S. P., Gouldsworthy, A. M., Kandels-Lewis, S. E., Carmena, M., Smythe, C., Gerloff, D. L., and Earnshaw, W. C. (2000). INCENP binds the Aurora-related kinase AIRK2 and is required to target it to chromosomes, the central spindle and cleavage furrow. Curr Biol, 10, 1075–1078.

Ainsztein, A. M., Kandels-Lewis, S. E., Mackay, A. M., and Eamshaw, W. C. (1998). INCENP centromere and spindle targeting: identification of essential conserved motifs and involvement of heterochromatin protein HP1. J Cell Biol, 143, 1763–1774.

Allshire, R. C., Nimmo, E. R., Ekwall, K., Javerzat, J. P. and Cranston, G. (1995) Mutations derepressing silent centromeric domains in fission yeast disrupt chromosome segregation. Genes Dev, 9, 218–33.

Altschul, S. F., Madden, T. L., Schaffer, A. A., Zhang, J., Zhang, Z., Miller, W. and Lipman, D. J. (1997) Gapped BLAST and PSI-BLAST: a new generation of protein database search programs. Nucleic Acids Res, 25, 3389–402.

Ball, L. J., Murzina, N. V., Broadhurst, R. W., Raine, A. R. C., Archer, S. J., Stott, F. J., Murzin, A. G., Singh, P. B., Domaille, P. J. and Laue, E. D. (1997) Structure of the chromatin binding (chromo) domain from mouse modifier protein 1. EMBO J, 16, 2473–2481.

Bannister, A. J., Zegerman, P., Partridge, J. F., Miska, E. A., Thomas, J. O., Allshire, R. C., and Kouzarides, T. (2001). Selective recognition of methylated lysine 9 on histone H3 by the HP1 chromo domain. Nature, 410, 120–124.

Baudat, F., Manova, K., Yuen, J. P., Jasin, M., and Keeney, S. (2000). Chromosome synapsis defects and sexually dimorphic meiotic progression in mice lacking spo11. Mol Cell, 6, 989–998.

Bassett, D. E., Jr., Boguski, M. S., Spencer, F., Reeves, R., Goebl, M. and Hieter, P. (1995) Comparative genomics, genome cross-referencing and XREFdb. Trends Genet, 11, 372–3.

Bernard, P., Hardwick, K., and Javerzat, J. P. (1998). Fission yeast Bub1 is a mitotic centromere protein essential for the spindle checkpoint and the preservation of correct ploidy through mitosis. J Cell Biol, 143, 1775–1787.

Boulianne, G. L., et al., (1984), Nature 312: 643–646

Bunick, D., Johnson, P. A., Johnson, T. R. and Hecht, N. B. (1990) Transcription of the testis-specific mouse protamine 2 gene in a homologous in vitro transcription system. Proc Natl Acad Sci U S A, 87, 891–5.

Burgoyne, P. S. (1982). Genetic homology and crossing over in the X and Y chromosomes of mammals. Hum Genet, 61, 85–90.

Calenda, A., Allenet, B., Escalier, D., Bach, J. F. and Garchon, H. J. (1994) The meiosis-specific Xmr gene product is homologous to the lymphocyte Xlr protein and is a component of the XY body. Embo J, 13, 100–9.

Cobb, J., Miyaike, M., Kikuchi, A., and Handel, M. A. (1999). Meiotic events at the centromeric heterochromatin: histone H3 phosphorylation, topoisomerase II alpha localization and chromosome condensation. Chromosoma, 108,412–425.

Cortez, D. and Elledge, S. J. (2000). Conducting the mitotic symphony. Nature, 406, 354–356.

Csink, A. and Henikoff, S. (1996). Genetic modification of heterochromatic association and nuclear organization in Drosophila. Nature, 381, 529–531.

Cutts, S. M., Fowler, K. J., Kile, B. T., Hii, L. L., O'Dowd, R. A., Hudson, D. F., Saffery, R., Kalitsis, P., Earle, E., and Choo, K. H. (1999). Defective chromosome segregation, microtubule bundling and nuclear bridging in inner centromere protein gene (Incenp)-disrupted mice. Hum Mol Genet, 8, 1145–1155.

Czvitkovich, S., Sauer, S., Peters, A. H. F. M., Deiner, E., Wolf, A., Laible, G., Opravil, S., Beug, H., and Jenuwein, T. (2001). Modulation of higher-order chromatin by the SUV39H1 histone methyltransferase induces altered proliferation and differentiation in transgenic mice. *Mech Dev*, in press.

Dernburg, A. F., Broman, K. W., Fung, J. C., Marshall, W. F., Philips, J., Agard, D. A., and Sedat, J. W. (1996a). Perturbation of nuclear architecture by long-distance chromosome interactions. *Cell*, 85, 745–759.

Dernburg, A. F., Sedat, J. W. and Hawley, R. S. (1996b) Direct evidence for a role of heterochromatin in meiotic chromosome segregation. *Cell*, 86, 135–146.

de Vries, S. S., Baart, E. B., Dekker, M., Siezen, A., de Rooij, D. G., de Boer, P., and te Riele, H. (1999). Mouse MutS-like protein Msh5 is required for proper chromosome synapsis in male and female meiosis. *Genes Dev*, 13, 523–531.

Dugaiczyk, A., Haron, J. A., Stone, E. M., Dennison, O. E., Rothblum, K. N. and Schwartz, R. J. (1983) Cloning and sequencing of a deoxyribonucleic acid copy of glyceraldehyde-3-phosphate dehydrogenase messenger ribonucleic acid isolated from chicken muscle. *Biochemistry*, 22, 1605–13.

Ekwall, K., Olsson, T., Turner, B. M., Cranston, G., and Allshire, R. C. (1997). Transient inhibition of histone deacetylation alters the structural and functional imprint at fission yeast centromeres. *Cell*, 91, 1021–1032.

Foon, K. A., and Gale, R. P. (1995). Chronic Lymphoid Leukemias. In *Blood: Principles and Practise of Hematology*, R. I. Handin, T. P. Stossel and S. E. Lux, eds. (J.B. Lippincott Company, Philadelphia), pp783–811.

Gentz et al., *Proc. Natl. Acad. Sci. USA* 86:821–824 (1989), hexa-histidine provides for convenient purification of the fusion protein.

Graziano, R. F., et al., (1995), J. Immunol. 155: 4996–5002

Handel, M. A. and Hunt, P. A. (1992) Sex-chromosome pairing and activity during mammalian meiosis. *Bioessays*, 14, 817–22.

Hawley, R. S., Irick, H., Zitron, A. E., Haddox, D. A., Lohe, A., New, C., Whitley, M. D., Arbel, T., Jang, J., McKim, K., and et al. (1992). There are two mechanisms of achiasmate segregation in *Drosophila* females, one of which requires heterochromatic homology. *Dev Genet*, 13, 440–467.

Heitz, E. (1928). Das Heterochromatin der Moose. *Jhrb. Wiss. Botanik*, 69, 762–818.

Henikoff, S. (1997) Position effect variegation in *Drosophila*: recent progress. *Epigenetic mechanisms of gene regulation*. CSHL press.

Hsu, J. Y., Sun, Z. W., Li, X., Reuben, M., Tatchell, K., Bishop, D. K., Grushcow, J. M., Brame, C. J., Caldwell, J. A., Hunt, D. F., Lin, R., Smith, M. M., and Allis, C. D. (2000). Mitotic phosphorylation of histone H3 is governed by Ipl1/aurora kinase and Glc7/PP1 phosphatase in budding yeast and nematodes. *Cell*, 102, 279–291.

Ivanova, A. V., Bonaduce, M. J., Ivanov, S. V. and Klar, A. J. (1998) The chromo and SET domains of the Clr4 protein are essential for silencing in fission yeast. *Nat Genet*, 19, 192–5.

Jenuwein, T., Laible, G., Dorn, R. and Reuter, G. (1998) SET domain proteins modulate chromatin domains in eu- and heterochromatin. *Cell Mol Life Sci*, 54, 80–93.

Jenuwein, T. (2001). Re-SET-ting heterochromatin by histone methyltransferases. *Trends Cell Biol*, 11, 266–273.

Jones, D. A., Cowell, F. G., and Singh, P. B. (2000). Mammalian chromodomain proteins: their role in genome organisation and expression. *Bioessays*, 22, 124

Kaitna, S., Mendoza, M., Jantsch-Plunger, V., and Glotzer, M. (2000). Incenp and an aurora-like kinase form a complex essential for chromosome segregation and efficient completion of cytokinesis. *Curr Biol*, 10, 1172–1181.

Karpen, G. H., Le, M. H., and Le, H. (1996). Centric heterochromatin and the efficiency of achiasmate disjunction in *Drosophila* female meiosis. *Science*, 273, 118–122.

Karpen, G. H. and Allshire, R. C. (1997) The case for epigenetic effects on centromere identity and function. *Trends Genet*, 13, 489–496.

Köhler, G. und Milstein, C. (1975), *Nature* 265, 495–497.

Koonin, E. V., Zhou, S. and Lucchesi, J. C. (1995) The chromo superfamily: new members, duplication of the chromo domain and possible role in delivering transcription regulators to chromatin. *Nucleic Acids Res*, 23, 4229–33.

Kot, M. C. and Handel, M. A. (1990) Spermatogenesis in XO,Sxr mice: role of the Y chromosome. *J Exp Zool*, 256, 92–105.

Lachner, M., O'Carroll, D., Rea, S., Mechtler, K., and Jenuwein, T. (2001). Methylation of histone H3 lysine 9 creates a binding site for HP1 proteins. *Nature*, 410, 116–120.

Laible, G., Wolf, A., Dorn, R., Reuter, G., Nislow, C., Lebersorger, A., Popkin, D., Pillus, L. and Jenuwein, T. (1997) Mammalian homologues of the Polycomb-group gene Enhancer of zeste mediate gene silencing in *Drosophila* heterochromatin and at *S. cerevisiae* telomeres. *Embo J*, 16, 3219–32.

Lamb D J, Niederberger C S. (1994) Animal models that mimic human male reproductive defects. Urol Clin North Am August;21(3):377–87.

Lammers, J. H., Offenberg, H. H., van Aalderen, M., Vink, A. C., Dietrich, A. J. and Heyting, C. (1994) The gene encoding a major component of the lateral elements of synaptonemal complexes of the rat is related to X-linked lymphocyte-regulated genes. *Mol Cell Biol*, 14, 1137–46.

Lammers, J. H., van Aalderen, M., Peters, A. H. F. M., van Pelt, A. A., de Rooij, D. G., de Boer, P., Offenberg, H. H., Dietrich, A. J., and Heyting, C. (1995). A change in the phosphorylation pattern of the 30,000–33,000 Mr synaptonemal complex proteins of the rat between early and mid-pachytene. *Chromosoma*, 104, 154–163.

Matsuda, Y., Hirobe, T. and Chapman, V. M. (1991) Genetic basis of X-Y chromosome dissociation and male sterility in interspecific hybrids. *Proc Natl Acad Sci U S A*, 88, 4850–4.

Meistrich, M. L. a. B., W. A. (1987) Proteins of the meiotic cell nucleus. In Moens, P. B. (ed.) *Meiosis*. Academic Press, New York, N.Y.

Melcher, M., Schmid, M., Aagaard, L., Selenko, P., Laible, G. and Jenuwein, T. (2000) Structure-function analysis of SUV39H1 reveals a dominant role in heterochromatin organization, chromosome segregation, and mitotic progression. *Mol Cell Biol*, 20, 3728–41.

Messmer, S., Franke, A. and Paro, R. (1992) Analysis of the functional role of the Polycomb chromo domain in *Drosophila melanogaster*. *Genes Dev,* 6, 1241–54.

Moens, P. B. (1995) Histones H1 and H4 of surface-spread meiotic chromosomes. *Chromosoma,* 104, 169–74.

Motzkus, D., Singh, P. B. and Hoyer-Fender, S. (1999) M31, a murine homolog of *Drosophila* HP1, is concentrated in the XY body during spermatogenesis. *Cytogenet Cell Genet,* 86, 83–8.

Nakayama, J., Rice, J. C., Strahl, B. D., Allis, C. D., and Grewal, S. I. (2001). Role of histone H3 lysine 9 methylation in epigenetic control of heterochromatin assembly. *Science,* 292, 110–113.

Neuberger, M. S., et al., (1984), Nature 312: 604–608

O'Carroll, D., Scherthan, H., Peters, A. H. F. M., Opravil, S., Haynes, A. R., Laible, G., Rea, S., Schmid, M., Lebersorger, A., Jerratsch, M., Sattler, L., Mattei, M. G., Denny, P., Brown, S. D., Schweizer, D., and Jenuwein, T. (2000). Isolation and characterization of Suv39h2, a second histone H3 methyltransferase gene that displays testis-specific expression. *Mol Cell Biol,* 20, 9423–9433.

Offenberg, H. H., Dietrich, A. J., and Heyting, C. (1991). Tissue distribution of two major components of synaptonemal complexes of the rat. *Chromosoma,* 101, 83–91.

Pandita, T. K., Westphal, C. H., Anger, M., Sawant, S. G., Geard, C. R., Pandita, R. K. and Scherthan, H. (1999) Atm inactivation results in aberrant telomere clustering during meiotic prophase. *Mol Cell Biol,* 19, 5096–105.

Pardue, M. L., and Gall, J. G. (1970). Chromosomal localization of mouse satellite DNA. *Science,* 168, 1356–1358.

Paro, R. and Harte, P. J. (1996) *The role of Polycomb group and thrithorax group complexes in the maintenance of determined cell states.* Coldspring Harbour Laboratory Press, New York, N.Y.

Paro, R. and Hogness, D. S. (1991) The Polycomb protein shares a homologous domain with a heterochromatin-associated protein of *Drosophila*. *Proc Natl Acad Sci U S A,* 88, 263–7.

Peters, A. H. F. M., Plug, A. W., van Vugt, M. J., and de Boer, P. (1997a). A drying-down technique for the spreading of mammalian meiocytes from the male and female germline. *Chromosome Res,* 5, 66–68.

Peters, A. H. F. M., Plug, A. W., and de Boer, P. (1997b). Meiosis in carriers of heteromorphic bivalents: sex differences and implications for male fertility. *Chromosome Res,* 5, 313–324.

Platero, J. S., Hartnett, T. and Eissenberg, J. C. (1995) Functional analysis of the chromo domain of HP1. *Embo J,* 14, 3977–86.

Rea, S., Eisenhaber, F., O'Carroll, D., Strahl, B. D., Sun, Z., Schmid, M., Opravil, S., Mechtler, K., Ponting, C. P., Allis, C. D. and Jenuwein, T. (2000) Regulation of chromatin structure by site-specific histone H3 methyltransferases. *Nature,* 406, 593–599.

Reuter, G. and Spierer, P. (1992) Position effect variegation and chromatin proteins. *BioEssays,* 14, 605–612.

Rice, J. C. and Allis, C. D. (2001) Histone methylation versus acetylation: new insights into epigenetic regulation. *Curr Opin Cell Biol,* 13, 263–273.

Riechmann, L., et al., (1988), Nature 332: 323–327.

Sambrook, J., Fritsch, E. F. and Maniatis, T. (1989) *Molecular cloning: A laboratory manual*. Cold Spring Harbour Laboratory Press, New York.

Scherthan, H., Weich, S., Schwegler, H., Heyting, C., Harle, M. and Cremer, T. (1996) Centromere and telomere movements during early meiotic prophase of mouse and man are associated with the onset of chromosome pairing. *J Cell Biol,* 134, 1109–25.

Solari, A. J. (1974) The behavior of the XY pair in mammals. *Int Rev Cytol,* 38, 273–317.

Stassen, M. J., Bailey, D., Nelson, S., Chinwalla, V. and Harte, P. J. (1995) The *Drosophila* trithorax proteins contain a novel variant of the nuclear receptor type DNA binding domain and an ancient conserved motif found in other chromosomal proteins. *Mech Dev,* 52, 209–23.

Strahl, B. D., Ohba, R., Cook, R. G. and Allis, C. D. (1999) Methylation of histone H3 at lysine 4 is highly conserved and correlates with transcriptionally active nuclei in Tetrahymena. *Proc Natl Acad Sci U S A,* 96, 14967–72.

Tkachuk, D. C., Kohler, S. and Cleary, M. L. (1992) Involvement of a homolog of *Drosophila* trithorax by 11q23 chromosomal translocations in acute leukemias. *Cell,* 71, 691–700.

Tschiersch, B., Hofmann, A., Krauss, V., Dorn, R., Korge, G. and Reuter, G. (1994) The protein encoded by the *Drosophila* position-effect variegation suppressor gene Su(var) 3-9 combines domains of antagonistic regulators of homeotic gene complexes. *Embo J,* 13, 3822–31.

Turner, J. M., Mahadevaiah, S. K., Benavente, R., Offenberg, H. H., Heyting, C., and Burgoyne, P. S. (2000). Analysis of male meiotic "sex body" proteins during XY female meiosis provides new insights into their functions. *Chromosoma,* 109,426–432.

Wallrath, L. L. (1998) Unfolding the mysteries of heterochromatin. *Curr Opin Genet Dev,* 8, 147–53.

Weinbauer G F, Aslam H, Krishnamurthy H, Brinkworth M H, Einspanier A, Hodges J K. (2001). Quantitative analysis of spermatogenesis and apoptosis in the common marmoset (Callithrix jacchus) reveals high rates of spermatogonial turnover and high spermatogenic efficiency. Biol Reprod. 2001 January;64(1):120–6.

Wilson et al., *Cell* 37: 767 (1984).

Wreggett, K. A., Hill, F., James, P. S., Hutchings, A., Butcher, G. W. and Singh, P. B. (1994) A mammalian homologue of *Drosophila heterochromatin* protein 1 (HP1) is a component of constitutive heterochromatin. *Cytogenet Cell Genet,* 66, 99–103.

Xu, Y., Ashley, T., Brainerd, E. E., Bronson, R. T., Meyn, M. S., and Baltimore, D. (1996). Targeted disruption of ATM leads to growth retardation, chromosomal fragmentation during meiosis, immune defects, and thymic lymphoma. *Genes Dev,* 10, 2411–2422.

Yoshida, K., Kandoh, G., Matsuda, Y., Habu, T., Nishimune, Y., and Morita, T. (1998). The mouse RecA-like gene Dmc1 is required for homologous chromosome synapsis during meiosis. *Mol Cell,* 1, 707–718.

Yuan, L., Liu, J. G., Zhao, J., Brundell, E., Daneholt, B., and Hoog, C. (2000). The murine Scp3 gene is required for synaptonemal complex assembly, chromosome synapsis, and male fertility. *Mol. Cell,* 5, 73–83.

What is claimed is:

1. An isolated nucleic acid molecule comprising a first polynucleotide, wherein said first polynueleotide is capable of hybridizing under stringent hybridization conditions to a second polynucleotide having a nucleotide sequence selected from the group consisting of:
   (a) a nucleotide sequence having the nucleotide sequence in SEQ ID NO:1 encoding a polypeptide having the amino acid sequence in SEQ ID NO:2; and
   (b) a nucleotide sequence complementary to the nucleotide sequence in (a),
   wherein said first polynucleotide encodes a polypeptide which has histone methyltransferase activity and localizes to sex chromosomes.

2. The nucleic acid molecule of claim 1, which is (a).

3. The nucleic acid molecule of claim 1, which is (b).

4. The nucleic acid molecule of claim 1, which is double stranded.

5. The nucleic acid molecule of claim 1, which is single stranded.

6. The nucleic acid molecule of claim 1, which is DNA.

7. The nucleic acid molecule of claim 1, which is RNA.

8. The nucleic acid molecule of claim 1, further comprising a heterologous polynucleotide.

9. The nucleic acid molecule of claim 8, wherein said heterologous polynucleotide encodes a heterologous polypeptide.

10. The nucleic acid molecule of claim 1, further comprising a non-coding sequence.

11. The nucleic acid molecule of claim 1, further comprising a regulatory sequence.

12. The nucleic acid molecule of claim 11, wherein said regulatory sequence encodes a promoter.

13. The nucleic acid molecule of claim 11, wherein said regulatory sequence encodes an enhancer.

14. A recombinant vector comprising the nucleic acid molecule of claim 1.

15. The recombinant vector of claim 14, wherein said nucleic acid molecule is DNA.

16. A method of making a recombinant vector comprising inserting the nucleic acid of claim 1 into a vector.

17. A recombinant vector produced by the method of claim 16.

18. A method of making a recombinant host cell comprising introducing the recombinant vector of claim 17 into a host cell.

19. An isolated recombinant host cell produced by the method of claim 18.

20. A recombinant method for producing a polypeptide, comprising culturing the recombinant host cell of claim 19 under conditions such that said polypeptide is expressed and recovering said polypeptide.

* * * * *

SEQUENCE LISTING

<160> NUMBER OF SEQ ID NOS: 21

<210> SEQ ID NO 1
<211> LENGTH: 1452
<212> TYPE: DNA
<213> ORGANISM: Mus musculus
<220> FEATURE:
<221> NAME/KEY: 3'UTR
<222> LOCATION: (1)..(18)
<220> FEATURE:
<221> NAME/KEY: CDS
<222> LOCATION: (19)..(1452)

<400> SEQUENCE: 1

```
gaatgaaagc tccgcaag atg gcg acg gcc agg gcc aag gca cgg ggc agt        51
                    Met Ala Thr Ala Arg Ala Lys Ala Arg Gly Ser
                    1               5                  10 gag gca gga gcg cgg tgt cac cgg gct cca ggt ccg ccc ccg agg ccc         99
Glu Ala Gly Ala Arg Cys His Arg Ala Pro Gly Pro Pro Pro Arg Pro
               15                  20                  25 aag gcc agg cga acg gcg aga cgc cgc cgc gcg gag acc ctg acg gcg        147
Lys Ala Arg Arg Thr Ala Arg Arg Arg Ala Glu Thr Leu Thr Ala
           30                  35                  40 cga cgc tcg cgg ccg tct gcg ggc gag agg cgc gcc ggc tcc cag cga        195
Arg Arg Ser Arg Pro Ser Ala Gly Glu Arg Arg Ala Gly Ser Gln Arg
       45                  50                  55 gcg tgg tcc gga gct ccg cgg gcc gcg gtc ttt ggc gac gag tgt gca        243
Ala Trp Ser Gly Ala Pro Arg Ala Ala Val Phe Gly Asp Glu Cys Ala
60                  65                  70                  75 cga ggt gcc tta ttc aag gcc tgg tgt gtg cct tgc cta gtt tca ctt        291
Arg Gly Ala Leu Phe Lys Ala Trp Cys Val Pro Cys Leu Val Ser Leu
                80                  85                  90 gat act ctc cag gaa tta tgt aga aaa gaa aag ctc aca tgt aaa tcg        339
Asp Thr Leu Gln Glu Leu Cys Arg Lys Glu Lys Leu Thr Cys Lys Ser
            95                 100                 105 att gga atc acc aaa agg aat cta aac aat tat gag gtg gag tac ttg        387
Ile Gly Ile Thr Lys Arg Asn Leu Asn Asn Tyr Glu Val Glu Tyr Leu
        110                 115                 120 tgt gac tac aag gta gca aag ggt gtg gaa tat tat ctt gta aaa tgg        435
Cys Asp Tyr Lys Val Ala Lys Gly Val Glu Tyr Tyr Leu Val Lys Trp
    125                 130                 135 aaa gga tgg cca gat tct aca aac acc tgg gag ccc ttg aga aac ctc        483
Lys Gly Trp Pro Asp Ser Thr Asn Thr Trp Glu Pro Leu Arg Asn Leu
140                 145                 150                 155 agg tgt cca cag ctc ctg cgg cag ttc tct gat gac aag aag act tac        531
Arg Cys Pro Gln Leu Leu Arg Gln Phe Ser Asp Asp Lys Lys Thr Tyr
                160                 165                 170 tta gct cag gaa agg aaa tgc aag gct gtc aat tca aaa tcc ttg caa        579
Leu Ala Gln Glu Arg Lys Cys Lys Ala Val Asn Ser Lys Ser Leu Gln
            175                 180                 185 cct gca att gct gag tat att gta cag aaa gct aag caa aga ata gct        627
Pro Ala Ile Ala Glu Tyr Ile Val Gln Lys Ala Lys Gln Arg Ile Ala
        190                 195                 200 ctg cag aga tgg caa gat tac ctc aac aga aga aag aac cat aag ggg        675
Leu Gln Arg Trp Gln Asp Tyr Leu Asn Arg Arg Lys Asn His Lys Gly
    205                 210                 215 atg ata ttt gtt gaa aac act gtt gac ttg gag ggc cca cct tta gac        723
Met Ile Phe Val Glu Asn Thr Val Asp Leu Glu Gly Pro Pro Leu Asp
220                 225                 230                 235 ttc tac tac att aac gag tac agg cca gct ccc ggg atc agc ata aac        771
```

```
                                                                             819
agt gaa gcc acc ttt gga tgt tca tgt aca gac tgc ttc ttt gac aag
Ser Glu Ala Thr Phe Gly Cys Ser Cys Thr Asp Cys Phe Phe Asp Lys
            255                 260                 265

867
tgt tgt cct gct gaa gct gga gtt gtg ttg gct tat aat aag aag caa
Cys Cys Pro Ala Glu Ala Gly Val Val Leu Ala Tyr Asn Lys Lys Gln
        270                 275                 280

915
caa att aaa atc caa cca ggc act ccc atc tac gaa tgc aac tca agg
Gln Ile Lys Ile Gln Pro Gly Thr Pro Ile Tyr Glu Cys Asn Ser Arg
    285                 290                 295

963
tgt cga tgt gga cct gaa tgt ccc aat agg att gta caa aaa ggc aca
Cys Arg Cys Gly Pro Glu Cys Pro Asn Arg Ile Val Gln Lys Gly Thr
300                 305                 310                 315

1011
caa tat tca ctg tgc atc ttt aaa act agc aat ggc tgt ggt tgg ggt
Gln Tyr Ser Leu Cys Ile Phe Lys Thr Ser Asn Gly Cys Gly Trp Gly
                320                 325                 330

1059
gta aaa acc ctt gtg aag att aaa aga atg agt ttt gtc atg gaa tat
Val Lys Thr Leu Val Lys Ile Lys Arg Met Ser Phe Val Met Glu Tyr
            335                 340                 345

1107
gtt gga gag gtg atc aca agt gaa gag gcc gag aga cgg gga cag ttc
Val Gly Glu Val Ile Thr Ser Glu Glu Ala Glu Arg Arg Gly Gln Phe
        350                 355                 360

1155
tat gac aac aaa ggg atc acc tac ctc ttt gac ctg gac tac gag tct
Tyr Asp Asn Lys Gly Ile Thr Tyr Leu Phe Asp Leu Asp Tyr Glu Ser
    365                 370                 375

1203
gat gag ttc aca gtg gat gca gct cga tat gga aac gta tcc cat ttt
Asp Glu Phe Thr Val Asp Ala Ala Arg Tyr Gly Asn Val Ser His Phe
380                 385                 390                 395

1251
gtg aat cat agt tgt gac cca aat ctt cag gtg ttt agt gtt ttc atc
Val Asn His Ser Cys Asp Pro Asn Leu Gln Val Phe Ser Val Phe Ile
                400                 405                 410

1299
gat aac ctt gat act cgg ctg ccc agg ata gca ttg ttc tct aca aga
Asp Asn Leu Asp Thr Arg Leu Pro Arg Ile Ala Leu Phe Ser Thr Arg
            415                 420                 425

1347
acc ata aac gct gga gaa gag ctg act ttt gac tat caa atg aaa ggt
Thr Ile Asn Ala Gly Glu Glu Leu Thr Phe Asp Tyr Gln Met Lys Gly
        430                 435                 440

1395
tct gga gaa gca tct tca gac tcc att gac cac agc cct gcc aaa aaa
Ser Gly Glu Ala Ser Ser Asp Ser Ile Asp His Ser Pro Ala Lys Lys
    445                 450                 455

1443
agg gtc aga acc caa tgt aaa tgt gga gcc gag act tgc aga ggt tac
Arg Val Arg Thr Gln Cys Lys Cys Gly Ala Glu Thr Cys Arg Gly Tyr
460                 465                 470                 475 ctc aac tga                                                                 1452
Leu Asn <210> SEQ ID NO 2
<211> LENGTH: 477
<212> TYPE: PRT
<213> ORGANISM: Mus musculus

<400> SEQUENCE: 2

Met Ala Thr Ala Arg Ala Lys Ala Arg Gly Ser Glu Ala Gly Ala Arg
1               5                   10                  15

Cys His Arg Ala Pro Gly Pro Pro Arg Pro Lys Ala Arg Arg Thr
                20                  25                  30

Ala Arg Arg Arg Arg Ala Glu Thr Leu Thr Ala Arg Arg Ser Arg Pro
            35                  40                  45
```

-continued

```
Ser Ala Gly Glu Arg Arg Ala Gly Ser Gln Arg Ala Trp Ser Gly Ala
         50                  55                  60

Pro Arg Ala Ala Val Phe Gly Asp Glu Cys Ala Arg Gly Ala Leu Phe
 65                  70                  75                  80

Lys Ala Trp Cys Val Pro Cys Leu Val Ser Leu Asp Thr Leu Gln Glu
                 85                  90                  95

Leu Cys Arg Lys Glu Lys Leu Thr Cys Lys Ser Ile Gly Ile Thr Lys
                100                 105                 110

Arg Asn Leu Asn Asn Tyr Glu Val Glu Tyr Leu Cys Asp Tyr Lys Val
            115                 120                 125

Ala Lys Gly Val Glu Tyr Tyr Leu Val Lys Trp Lys Gly Trp Pro Asp
        130                 135                 140

Ser Thr Asn Thr Trp Glu Pro Leu Arg Asn Leu Arg Cys Pro Gln Leu
145                 150                 155                 160

Leu Arg Gln Phe Ser Asp Asp Lys Lys Thr Tyr Leu Ala Gln Glu Arg
                165                 170                 175

Lys Cys Lys Ala Val Asn Ser Lys Ser Leu Gln Pro Ala Ile Ala Glu
            180                 185                 190

Tyr Ile Val Gln Lys Ala Lys Gln Arg Ile Ala Leu Gln Arg Trp Gln
        195                 200                 205

Asp Tyr Leu Asn Arg Arg Lys Asn His Lys Gly Met Ile Phe Val Glu
    210                 215                 220

Asn Thr Val Asp Leu Glu Gly Pro Pro Leu Asp Phe Tyr Tyr Ile Asn
225                 230                 235                 240

Glu Tyr Arg Pro Ala Pro Gly Ile Ser Ile Asn Ser Glu Ala Thr Phe
                245                 250                 255

Gly Cys Ser Cys Thr Asp Cys Phe Phe Asp Lys Cys Cys Pro Ala Glu
            260                 265                 270

Ala Gly Val Val Leu Ala Tyr Asn Lys Lys Gln Gln Ile Lys Ile Gln
        275                 280                 285

Pro Gly Thr Pro Ile Tyr Glu Cys Asn Ser Arg Cys Arg Cys Gly Pro
    290                 295                 300

Glu Cys Pro Asn Arg Ile Val Gln Lys Gly Thr Gln Tyr Ser Leu Cys
305                 310                 315                 320

Ile Phe Lys Thr Ser Asn Gly Cys Gly Trp Gly Val Lys Thr Leu Val
                325                 330                 335

Lys Ile Lys Arg Met Ser Phe Val Met Glu Tyr Val Gly Glu Val Ile
            340                 345                 350

Thr Ser Glu Glu Ala Glu Arg Arg Gly Gln Phe Tyr Asp Asn Lys Gly
        355                 360                 365

Ile Thr Tyr Leu Phe Asp Leu Asp Tyr Glu Ser Asp Glu Phe Thr Val
    370                 375                 380

Asp Ala Ala Arg Tyr Gly Asn Val Ser His Phe Val Asn His Ser Cys
385                 390                 395                 400

Asp Pro Asn Leu Gln Val Phe Ser Val Phe Ile Asp Asn Leu Asp Thr
                405                 410                 415

Arg Leu Pro Arg Ile Ala Leu Phe Ser Thr Arg Thr Ile Asn Ala Gly
            420                 425                 430

Glu Glu Leu Thr Phe Asp Tyr Gln Met Lys Gly Ser Gly Glu Ala Ser
        435                 440                 445

Ser Asp Ser Ile Asp His Ser Pro Ala Lys Lys Arg Val Arg Thr Gln
    450                 455                 460

Cys Lys Cys Gly Ala Glu Thr Cys Arg Gly Tyr Leu Asn
```

```
                465             470             475
```

<210> SEQ ID NO 3
<211> LENGTH: 543
<212> TYPE: DNA
<213> ORGANISM: Homo sapiens
<220> FEATURE:
<221> NAME/KEY: misc_feature
<222> LOCATION: (1)..(543)
<223> OTHER INFORMATION: EST Acc. No.173625
<220> FEATURE:
<221> NAME/KEY: unsure
<222> LOCATION: (15)
<223> OTHER INFORMATION: May be any nucleic acid.
<220> FEATURE:
<221> NAME/KEY: unsure
<222> LOCATION: (23)
<223> OTHER INFORMATION: May be any nucleic acid.
<220> FEATURE:
<221> NAME/KEY: unsure
<222> LOCATION: (30)
<223> OTHER INFORMATION: May be any nucleic acid.
<220> FEATURE:
<221> NAME/KEY: unsure
<222> LOCATION: (31)..(32)
<223> OTHER INFORMATION: May be any nucleic acid.
<220> FEATURE:
<221> NAME/KEY: unsure
<222> LOCATION: (35)
<223> OTHER INFORMATION: May be any nucleic acid.
<220> FEATURE:
<221> NAME/KEY: unsure
<222> LOCATION: (39)..(40)
<223> OTHER INFORMATION: May be any nucleic acid.
<220> FEATURE:
<221> NAME/KEY: unsure
<222> LOCATION: (43)..(44)
<223> OTHER INFORMATION: May be any nucleic acid.
<220> FEATURE:
<221> NAME/KEY: unsure
<222> LOCATION: (49)..(50)
<223> OTHER INFORMATION: May be any nucleic acid.
<220> FEATURE:
<221> NAME/KEY: unsure
<222> LOCATION: (505)
<223> OTHER INFORMATION: May be any nucleic acid.

<400> SEQUENCE: 3

```
ggccatgtgg ttgancccct ggntttaccn nnccntggnn ggnnttgann cccctttagat      60 tatagtccag aatcattgtt gtcatataac tgccctcatc tttcagcttc gtcacttgtg     120
attacctttc caacttattc catgacaaaa cttattcttt taatcttcac atgggttttt     180 acccccagc catggtcatt gatactgtga aagatgcaaa gtgaattact gtgtgccttt      240
ttgtacaatc ctattggtac agtgaggtcc acattgacag attgagatgc atttatagat     300
gggagtaaca ggtgggattt taatttgttg gttttttacta taagccaaaa gaattccagc    360
ttcaccaaga caacattttt catagaagca atctgtgcat gaacaacaaa aggtagcttc     420
atttactaag ctgattccag gagctggttt gtattcatca atatagcaga agtctgaagg     480
tgggccttct aagtgaaccc tattntcaac aaatatcact cctttattat tctgtcttct    540
gcg                                                                   543
```

<210> SEQ ID NO 4
<211> LENGTH: 579
<212> TYPE: DNA
<213> ORGANISM: Homo sapiens
<220> FEATURE:
<221> NAME/KEY: misc_feature
<222> LOCATION: (1)..(579)
<223> OTHER INFORMATION: EST Acc. No. AQ494637

```
<220> FEATURE:
<221> NAME/KEY: unsure
<222> LOCATION: (25)
<223> OTHER INFORMATION: May be any nucleic acid.
<220> FEATURE:
<221> NAME/KEY: unsure
<222> LOCATION: (32)..(33)
<223> OTHER INFORMATION: May be any nucleic acid.
<220> FEATURE:
<221> NAME/KEY: unsure
<222> LOCATION: (36)
<223> OTHER INFORMATION: May be any nucleic acid.
<220> FEATURE:
<221> NAME/KEY: unsure
<222> LOCATION: (38)
<223> OTHER INFORMATION: May be any nucleic acid.
<220> FEATURE:
<221> NAME/KEY: unsure
<222> LOCATION: (39)
<223> OTHER INFORMATION: May be any nucleic acid.
<220> FEATURE:
<221> NAME/KEY: unsure
<222> LOCATION: (45)
<223> OTHER INFORMATION: May be any nucleic acid.
<220> FEATURE:
<221> NAME/KEY: unsure
<222> LOCATION: (51)
<223> OTHER INFORMATION: May be any nucleic acid.
<220> FEATURE:
<221> NAME/KEY: unsure
<222> LOCATION: (58)
<223> OTHER INFORMATION: May be any nucleic acid.
<220> FEATURE:
<221> NAME/KEY: unsure
<222> LOCATION: (66)
<223> OTHER INFORMATION: May be any nucleic acid.
<220> FEATURE:
<221> NAME/KEY: unsure
<222> LOCATION: (71)
<223> OTHER INFORMATION: May be any nucleic acid.
<220> FEATURE:
<221> NAME/KEY: unsure
<222> LOCATION: (73)
<223> OTHER INFORMATION: May be any nucleic acid.
<220> FEATURE:
<221> NAME/KEY: unsure
<222> LOCATION: (75)
<223> OTHER INFORMATION: May be any nucleic acid.
<220> FEATURE:
<221> NAME/KEY: unsure
<222> LOCATION: (126)
<223> OTHER INFORMATION: May be any nucleic acid.
<220> FEATURE:
<221> NAME/KEY: unsure
<222> LOCATION: (168)
<223> OTHER INFORMATION: May be any nucleic acid.
<220> FEATURE:
<221> NAME/KEY: unsure
<222> LOCATION: (170)
<223> OTHER INFORMATION: May be any nucleic acid.
<220> FEATURE:
<221> NAME/KEY: unsure
<222> LOCATION: (502)
<223> OTHER INFORMATION: May be any nucleic acid.
<220> FEATURE:
<221> NAME/KEY: unsure
<222> LOCATION: (524)
<223> OTHER INFORMATION: May be any nucleic acid.

<400> SEQUENCE: 4
gcttctcata catgatacgt gttcngctct gnngtntnng tttangaata cntaaaanaa      60
aaggnagggg ngncntttga ttcgtgtgat tccatagatg cactcatatg gaactgtatt     120
tcattntgtg aatcatagta gtgacccaaa tcttcatatg ttctatgntn tcactgataa     180
cttgacactg gccttcccta tatagctctg tgttccatga gaactataaa tgctggagaa     240
```

```
gagttgattt  ttgacaatca  aacaaaaagt  tctggggata  tatcttcaga  gtttattgac    300
cacagctcag  ccaaaaagag  ggtcagaact  gtatgtaaat  gtggagctgt  gacttgcaga    360
ggttgcctca  aatgaatttt  caggaaatag  aaatgatgat  aattggtagt  tgtttctttt    420
ttctaatgtt  atcattctaa  aaataagtat  ttggaactct  cttttcatat  tatcaagatt    480
attactatgt  taaattgaca  tncatggttc  aaggcattta  ccanatgcat  tactgatgcc    540
tcttgagaga  gggccactgt  gttgcataga  ctgatctga                             579
```

<210> SEQ ID NO 5
<211> LENGTH: 565
<212> TYPE: DNA
<213> ORGANISM: Homo sapiens
<220> FEATURE:
<221> NAME/KEY: misc_feature
<222> LOCATION: (1)..(565)
<223> OTHER INFORMATION: EST Acc. No. AQ691972
<220> FEATURE:
<221> NAME/KEY: unsure
<222> LOCATION: (19)
<223> OTHER INFORMATION: May be any nucleic acid.
<220> FEATURE:
<221> NAME/KEY: unsure
<222> LOCATION: (38)
<223> OTHER INFORMATION: May be any nucleic acid.
<220> FEATURE:
<221> NAME/KEY: unsure
<222> LOCATION: (42)
<223> OTHER INFORMATION: May be any nucleic acid.
<220> FEATURE:
<221> NAME/KEY: unsure
<222> LOCATION: (353)
<223> OTHER INFORMATION: May be any nucleic acid.
<220> FEATURE:
<221> NAME/KEY: unsure
<222> LOCATION: (397)
<223> OTHER INFORMATION: May be any nucleic acid.

<400> SEQUENCE: 5

```
agaggatgag  catggatcnt  cgctatagca  aaccacanat  anaatcccac  ctgttactcc     60
catctataaa  tgcatctcaa  tctgtcaatg  tggaccttac  tgtaccaata  ggattgtaca    120
aaaaggcaca  cagtaattca  ctttgcatct  ttcacagtat  caatgaccat  ggctggggtg    180
taaaaaccca  tgtgaagatt  aaaagaataa  gttttgtcat  ggaataagtt  ggaaaggtaa    240
tcacaagtga  cgaagctgaa  agatgagggc  agttatatga  caacaaatga  tctggactat    300
gaatctgatg  aattcacaga  ggatgcagct  caatatggaa  ctgtatttca  ttntgtgaat    360
cataagtagt  gacccaaact  tcatatgttc  aatgttntca  ttgataactt  gacactggcc    420
tttccttaat  agctctgtgt  tccatgagaa  ctataaatgc  tggagaagaa  gtgattttg     480 acatcaacaa  aagttctggg  attatcttca  aagttattgc  cacagttacc  aaaagaaggc    540
aaactgttgt  aatgtgagct  gtact                                             565
```

<210> SEQ ID NO 6
<211> LENGTH: 535
<212> TYPE: DNA
<213> ORGANISM: Homo sapiens
<220> FEATURE:
<221> NAME/KEY: misc_feature
<222> LOCATION: (1)..(535)
<223> OTHER INFORMATION: EST Acc. No. AQ554070

<400> SEQUENCE: 6

```
tcagactcat  agtccagatc  aaagagattc  tgtgattccc  ttgttgtcat  agaactgtcc     60 tcgtcttttca  gcttcttcac  ttgtgattac  ctaaacagaa  aaaactgtaa  gtatattacg    120
```

```
tagctactga accaaagaag cattcatcta cctatctact aatatgcgaa tacctacaaa      180
tatttaaaaa gtaagaaatt caggtgtcat caaagcaaac attcacacaa actaagactc      240
agatgcaaag aggtgggaaa atgaggggaa gaaaaatgat aatgcaaaag actgatgacc      300 ttttttttt  aaacagggtc tcactctgtc actcaggcta gaatgcggtg gtgccatcat      360
gactccctgt atcctttaac tcctgggatc aagcgatctt cctgcctcag cctcctgact      420
agctggatca caggtgcata ccgccatgcc cagctaatga tttagttttt atagagatgt      480
ggggtctcac tatgttgccc acactggtct ggaactcctg ggctcaagtg agcct           535
```

```
<210> SEQ ID NO 7
<211> LENGTH: 20
<212> TYPE: PRT
<213> ORGANISM: Homo sapiens

<400> SEQUENCE: 7

Ala Arg Thr Lys Gln Thr Ala Arg Lys Ser Thr Gly Gly Lys Ala Pro
 1               5                  10                  15

Arg Lys Gln Leu
            20

<210> SEQ ID NO 8
<211> LENGTH: 24
<212> TYPE: DNA
<213> ORGANISM: Artificial sequence
<220> FEATURE:
<223> OTHER INFORMATION: Primer

<400> SEQUENCE: 8
ggggatgata tttgttgaaa acac                                              24

<210> SEQ ID NO 9
<211> LENGTH: 24
<212> TYPE: DNA
<213> ORGANISM: Artificial sequence
<220> FEATURE:
<223> OTHER INFORMATION: Primer

<400> SEQUENCE: 9
ggttggattt taatttgttg cttc                                              24

<210> SEQ ID NO 10
<211> LENGTH: 19
<212> TYPE: DNA
<213> ORGANISM: Artificial sequence
<220> FEATURE:
<223> OTHER INFORMATION: Primer

<400> SEQUENCE: 10
gccctccaag tcaacagtg                                                    19

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
gtgttgaggt aatcttgcca tc                                                22

<210> SEQ ID NO 12
```

```
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 12
atgggggcag ggttttcggg tagac                                    25

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 13
aaatggtatt tgcaggccac ttcttg                                   26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 14
aaatggtatt tgcaggccac ttcttg                                   26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 15
ggatgggatg gtggaatggt ttttat                                   26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 16
aaatggtatt tgcaggccac ttcttg                                   26

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 17
aaatggtatt tgcaggccac ttcttg                                   26

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
```

```
gactgcctag tctggcactg aact                                              24

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
gatcactgcg tacatataca ctgat                                             25

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 20
tagacttcta ctacattaac g                                                 21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
gatgtcagtg gctatgaatg                                                   20
```